(12) United States Patent
Yin et al.

(10) Patent No.: US 9,796,749 B2
(45) Date of Patent: Oct. 24, 2017

(54) COMPOSITIONS AND METHODS RELATING TO NUCLEIC ACID NANO- AND MICRO-TECHNOLOGY

(75) Inventors: Peng Yin, Brookline, MA (US); Diming Wei, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/237,001

(22) PCT Filed: Aug. 2, 2012

(86) PCT No.: PCT/US2012/049306
§ 371 (c)(1),
(2), (4) Date: Mar. 31, 2014

(87) PCT Pub. No.: WO2013/022694
PCT Pub. Date: Feb. 14, 2013

(65) Prior Publication Data
US 2014/0213778 A1    Jul. 31, 2014

Related U.S. Application Data

(60) Provisional application No. 61/612,018, filed on Mar. 16, 2012, provisional application No. 61/515,435, filed on Aug. 5, 2011.

(51) Int. Cl.
| | | |
|---|---|---|
| *C07H 21/04* | (2006.01) | |
| *C12Q 1/68* | (2006.01) | |
| *B65D 5/20* | (2006.01) | |
| *B65D 5/24* | (2006.01) | |
| *C07H 21/00* | (2006.01) | |

(52) U.S. Cl.
CPC .............. *C07H 21/04* (2013.01); *C12Q 1/68* (2013.01)

(58) Field of Classification Search
CPC ................ C12Q 1/68; C12Q 2525/161; C12Q 2525/185; C12Q 2525/197; C12Q 2527/101; C12Q 2563/157; C12Q 2565/631; C07H 21/04
USPC ................................................ 536/23.1, 25.3
See application file for complete search history.

(56) References Cited

U.S. PATENT DOCUMENTS

| | | | |
|---|---|---|---|
| 6,255,469 | B1 | 7/2001 | Seeman et al. |
| 6,444,650 | B1 | 9/2002 | Cech et al. |
| 6,444,661 | B1 | 9/2002 | Barton et al. |
| 7,745,594 | B2 | 6/2010 | Seelig et al. |
| 7,842,793 | B2 | 11/2010 | Rothemund |
| 8,877,438 | B2 | 11/2014 | Yin |
| 2003/0219790 | A1 | 11/2003 | Seeman et al. |
| 2006/0078910 | A1 | 4/2006 | Seeman et al. |
| 2007/0117109 | A1 | 5/2007 | Rothemund |
| 2007/0238096 | A1 | 10/2007 | Reich et al. |
| 2008/0221315 | A1 | 9/2008 | Garibotti et al. |
| 2010/0216978 | A1 | 8/2010 | Shih |
| 2010/0291485 | A1 | 11/2010 | Lapsys et al. |
| 2012/0022244 | A1 | 1/2012 | Yin et al. |
| 2012/0251583 | A1 | 10/2012 | Rothemund |
| 2013/0065777 | A1 | 3/2013 | Altug et al. |
| 2013/0316358 | A1 | 11/2013 | Navon et al. |
| 2015/0218204 | A1 | 8/2015 | Yin et al. |
| 2015/0329584 | A1 | 11/2015 | Yin et al. |
| 2017/0015698 | A1 | 1/2017 | Iinuma et al. |

FOREIGN PATENT DOCUMENTS

| | | |
|---|---|---|
| CN | 1390253 A | 1/2003 |
| JP | 2004-510780 A | 4/2004 |
| JP | 2008-504846 A | 2/2008 |
| WO | WO 01/36624 A1 | 5/2001 |
| WO | WO 2005/024018 A1 | 3/2005 |
| WO | WO 2006/017432 A2 | 2/2006 |
| WO | WO 2007/012807 A2 | 2/2007 |
| WO | WO 2009/093558 A1 | 7/2009 |
| WO | WO 2012/058638 A2 | 5/2012 |
| WO | WO 2013/022694 A1 | 2/2013 |
| WO | WO 2013/088098 A2 | 6/2013 |
| WO | WO 2014/018675 A1 | 1/2014 |
| WO | WO 2014/074597 A1 | 5/2014 |

OTHER PUBLICATIONS

Yin et al. Science 321, 824 (2008).*
Acuna et al., Fluorescence enhancement at docking sites of DNA-directed self-assembled nanoantennas. Science. Oct. 26, 2012;338(6106):506-10. doi:10.1126/science.1228638.
Aldaye et al., Assembling materials with DNA as the guide. Science. Sep. 26, 2008;321(5897):1795-9. doi: 10.1126/science.1154533.
Aldaye et al., Modular access to structurally switchable 3D discrete DNA assemblies. J Am Chem Soc. Nov. 7, 2007;129(44):13376-7. Epub Oct. 16, 2007.
Aldaye et al., Sequential self-assembly of a DNA hexagon as a template for the organization of gold nanoparticles. Angew Chem Int Ed Engl. Mar. 27, 2006;45(14):2204-9.
Andersen et al., Self-assembly of a nanoscale DNA box with a controllable lid. Nature. May 7, 2009;459(7243):73-6. doi:10.1038/nature07971.
Barish et al., An information-bearing seed for nucleating algorithmic self-assembly. Proc Natl Acad Sci U S A. Apr. 14, 2009;106(15):6054-9. doi: 10.1073/pnas.0808736106. Epub Mar. 24, 2009.
Bath et al., DNA nanomachines. Nat Nanotechnol. May 2007;2(5):275-84. doi:10.1038/nnano 2007.104.

(Continued)

*Primary Examiner* — Janet Epps-Smith
(74) *Attorney, Agent, or Firm* — Wolf, Greenfield & Sacks, P.C.

(57) ABSTRACT

The invention provides nucleic acid structures of controlled size and shape, comprised of a plurality of oligonucleotides, and methods for their synthesis. The structures are formed, at least in part, by the self-assembly of single stranded oligonucleotides. The location of each oligonucleotide in the resultant structure is known. Accordingly, the structures may be modified with specificity.

23 Claims, 54 Drawing Sheets

(56) References Cited

OTHER PUBLICATIONS

Berardi et al., Mitochondrial uncoupling protein 2 structure determined by NMR molecular fragment searching. Nature. Jul. 24, 2011;476(7358):109-13. doi: 10.1038/nature10257.

Bhatia et al., Icosahedral DNA nanocapsules by modular assembly. Angew Chem Int Ed Engl. 2009;48(23):4134-7.doi:10.1002/anie.200806000.

Chen et al., DNA-directed assembly of single-wall carbon nanotubes. J Am Chem Soc. Jul. 18, 2007;129(28):8696-7. Epub Jun. 23, 2007.

Chen et al., Invadable self-assembly: combining robustness with efficiency. Proceeding SODA '04 Proceedings of the fifteenth annual ACM-SIAM symposium on Discrete algorithms. 2004:890-9.

Chen et al., Synthesis from DNA of a molecule with the connectivity of a cube. Nature. Apr. 18, 1991;350(6319):631-3.

Choi et al., Programmable in situ amplification for multiplexed imaging of mRNA expression. Nat Biotechnol. Nov. 2010;28(11):1208-12. doi: 10.1038/nbt.1692. Epub Oct. 31, 2010.

Chworos et al., Building programmable jigsaw puzzles with RNA. Science. Dec. 17, 2004;306(5704):2068-72.

Delebecque et al., Organization of intracellular reactions with rationally designed RNA assemblies. Science. Jul. 22, 2011;333(6041):470-4. doi: 10.1126/science.1206938. Epub Jun. 23, 2011.

Dietz et al., Folding DNA into twisted and curved nanoscale shapes. Science. Aug. 7, 2009;325(5941):725-30. doi: 10.1126/science.1174251.

Douglas et al., A logic-gated nanorobot for targeted transport of molecular payloads. Science. Feb. 17, 2012;335(6070):831-4. doi:10.1126/science.1214081.

Douglas et al., DNA-nanotube-induced alignment of membrane proteins for NMR structure determination. Proc Natl Acad Sci U S A. Apr. 17, 2007;104(16):6644-8. Epub Apr. 2, 2007.

Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.

Douglas et al., Self-assembly of DNA into nanoscale three-dimensional shapes. Nature. May 21, 2009;459(7245):414-8.doi: 10.1038/nature08016.

Erben et al., A self-assembled DNA bipyramid. J Am Chem Soc. Jun. 6, 2007;129(22):6992-3. Epub May 15, 2007.

Feldkamp et al., Rational design of DNA nanoarchitectures. Angew Chem Int Ed Engl. Mar. 13, 2006;45(12):1856-76.

Fu et al., DNA double-crossover molecules. Biochemistry. Apr. 6, 1993;32(13):3211-20.

Fu et al., Interenzyme substrate diffusion for an enzyme cascade organized on spatially addressable DNA nanostructures. J Am Chem Soc. Mar. 28, 2012;134(12):5516-9. doi:10.1021/ja300897h. Epub Mar. 16, 2012.

Geary et al., A single-stranded architecture for cotranscriptional folding of RNA nanostructures. Science. Aug. 15, 2014;345(6198):799-804. doi: 10.1126/science.1253920.

Goodman et al., Rapid chiral assembly of rigid DNA building blocks for molecular nanofabrication. Science. Dec. 9, 2005;310(5754):1661-5.

Goodman et al., Reconfigurable, braced, three-dimensional DNA nanostructures. Nat Nanotechnol. Feb. 2008;3(2):93-6. doi: 10.1038/nnano.2008.3. Epub Feb. 3, 2008.

Han et al., DNA gridiron nanostructures based on four-arm junctions. Science. Mar. 22, 2013;339(6126):1412-5. doi: 10.1126/science.1232252.

Han et al., DNA origami with complex curvatures in three-dimensional space. Science. Apr. 15, 2011;332(6027):342-6. doi:10.1126/science.1202998.

Han et al., Folding and cutting DNA into reconfigurable topological nanostructures. Nat Nanotechnol. Oct. 2010;5(10):712-7. doi:10.1038/nnano.2010.193. Epub Oct. 3, 2010.

Hansma et al., DNA binding to mica correlates with cationic radius:assay by atomic force microscopy. Biophys J. Apr. 1996;70(4):1933-9.

He et al., Hierarchical self-assembly of DNA into symmetric supramolecular polyhedra. Nature. Mar. 13, 2008;452(7184):198-201. doi: 10.1038/nature06597.

Hell, Far-field optical nanoscopy. Science. May 25, 2007;316(5828):1153-8.

Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.

Iinuma et al., Polyhedra self-assembled from DNA tripods and characterized with 3D DNA-PAINT. Science. Apr. 4, 2014;344(6179):65-9. doi: 10.1126/science.1250944. Epub Mar. 13, 2014.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Jungmann et al., Single-molecule kinetics and super-resolution microscopy by fluorescence imaging of transient binding on DNA origami. Nano Lett. Nov. 10, 2010;10(11):4756-61. doi:10.1021/nl103427w.

Kao et al., Tracking of single fluorescent particles in three dimensions: use of cylindrical optics to encode particle position. Biophys J. Sep. 1994;67(3):1291-300.

Ke et al., Multilayer DNA origami packed on a square lattice. J Am Chem Soc. Nov. 4, 2009;131(43):15903-8. doi:10.1021/ja906381y.

Ke et al., Multilayer DNA origami packed on hexagonal and hybrid lattices. J Am Chem Soc. Jan. 25, 2012;134(3):1770-4. doi:10.1021/ja209719k. Epub Jan. 13, 2012.

Ke et al., Scaffolded DNA origami of a DNA tetrahedron molecular container. Nano Lett. Jun. 2009;9(6):2445-7. doi:10.1021/nl901165f.

Ke et al., Three-dimensional structures self-assembled from DNA bricks. Science. Nov. 30, 2012;338(6111):1177-83. doi: 10.1126/science.1227268.

Killops et al., Robust, efficient, and orthogonal synthesis of dendrimers via thiol-ene "click" chemistry. J Am Chem Soc. Apr. 16, 2008;130(15):5062-4. doi: 10.1021/ja8006325. Epub Mar. 20, 2008.

Kuzuya et al., DNA origami: fold, stick, and beyond. Nanoscale. Mar. 2010;2(3):310-22. doi: 10.1039/b9nr00246d. Epub Nov. 24, 2009.

Kuzuya et al., Six-helix and eight-helix DNA nanotubes assembled from half-tubes. Nano Lett. Jun. 2007;7(6):1757-63. Epub May 15, 2007.

Kuzyk et al., DNA-based self-assembly of chiral plasmonic nanostructures with tailored optical response. Nature. Mar. 14, 2012;483(7389):311-4. doi:10.1038/nature10889.

Langecker et al., Synthetic lipid membrane channels formed by designed DNA nanostructures. Science. Nov. 16, 2012;338(6109):932-6. doi: 10.1126/science.1225624.

Le et al., DNA-Templated Self-Assembly of Metallic Nanocomponent Arrays on a Surface. Nano Lett. 2004;4(12):2343-7.

Leontis et al., Self-assembled RNA nanostructures. Science. Aug. 15, 2014;345(6198):732-3. doi:10.1126/science.1257989.

Li et al., Nucleic acid-based nanoengineering: novel structures for biomedical applications. Interface Focus. Oct. 6, 2011;1(5):702-24. doi: 10.1098/rsfs.2011.0040. Epub Jun. 28, 2011.

Li et al., Single-chain antibodies against DNA aptamers for use as adapter molecules on DNA tile arrays in nanoscale materials organization. Org Biomol Chem. Sep. 21, 2006;4(18):3420-6. Epub Jul. 28, 2006.

Liedl et al., Self-assembly of three-dimensional prestressed tensegrity structures from DNA. Nat Nanotechnol. Jul. 2010;5(7):520-4. doi: 10.1038/nnano.2010.107. Epub Jun. 20, 2010.

Lin et al., DNA tile based self-assembly: building complex nanoarchitectures. Chemphyschem. Aug. 11, 2006;7(8):1641-7.

(56) References Cited

OTHER PUBLICATIONS

Lin et al., Mirror image DNA nanostructures for chiral supramolecular assemblies. Nano Lett. Jan. 2009;9(1):433-6. doi:10.1021/nl803328v.
Lin et al., Submicrometre geometrically encoded fluorescent barcodes self-assembled from DNA. Nat Chem. 2012;4:832-9.
Linko et al., The enabled state of DNA nanotechnology. Curr Opin Biotechnol. Aug. 2013;24(4):555-61. doi: 10.1016/j.copbio.2013.02.001. Epub Apr. 6, 2013.
Liu et al., Approaching the limit: can one DNA oligonucleotide assemble into large nanostructures? Angew Chem Int Ed Engl. Mar. 13, 2006;45(12):1942-5.
Liu et al., Crystalline two-dimensional DNA-origami arrays. Angew Chem Int Ed Engl. Jan. 3, 2011;50(1):278-81. doi:10.1002/anie.201005911.
Liu et al., DNA nanotubes self-assembled from triple-crossover tiles as templates for conductive nanowires. Proc Natl Acad Sci U S A. Jan. 20, 2004;101(3):717-22. Epub Jan. 6, 2004.
Liu et al., Tensegrity: construction of rigid DNA triangles with flexible four-arm DNA junctions. J Am Chem Soc. Mar. 3, 2004;126(8):2324-5.
Liu et al., Three-dimensional plasmon rulers. Science. Jun. 17, 2011;332(6036):1407-10. doi:10.1126/science.1199958.
Mathieu et al., Six-helix bundles designed from DNA. Nano Lett. Apr. 2005;5(4):661-5.
Melosh et al., Ultrahigh-density nanowire lattices and circuits. Science. Apr. 4, 2003;300(5616):112-5. Epub Mar. 13, 2003.
Mitchell et al., Self-assembly of chiral DNA nanotubes. J Am Chem Soc. Dec. 22, 2004;126(50):16342-3.
Nie et al., Self-assembly of DNA nanoprisms with only two component strands. Chem Commun (Camb). Apr. 7, 2013;49(27):2807-9. doi:10.1039/c3cc39177a.
O'Neill et al., Sturdier DNA nanotubes via ligation. Nano Lett. Jul. 2006;6(7):1379-83.
Park et al., Finite-size, fully addressable DNA tile lattices formed by hierarchical assembly procedures. Angew Chem Int Ed Engl. Jan. 23, 2006;45(5):735-9. Erratum in: Angew Chem Int Ed Engl. Oct. 13, 2006;45(40):6607.
Park et al., Programmable DNA self-assemblies for nanoscale organization of ligands and proteins. Nano Lett. Apr. 2005;5(4):729-33.
Park et al., Three-helix bundle DNA tiles self-assemble into 2D lattice or 1D templates for silver nanowires. Nano Lett. Apr. 2005;5(4):693-6.
Pieles et al., Psoralen covalently linked to oligodeoxyribonucleotides: synthesis, sequence specific recognition of DNA and photo-cross-linking to pyrimidine residues of DNA. Nucleic Acids Res. Jan. 11, 1989;17(1):285-99.
Qi et al., A three-dimensional optical photonic crystal with designed point defects. Nature. Jun. 3, 2004;429(6991):538-42.
Qian et al., Scaling up digital circuit computation with DNA strand displacement cascades. Science. Jun. 3, 2011;332(6034):1196-201. doi:10.1126/science.1200520.
Rajendran et al., Photo-cross-linking-assisted thermal stability of DNA origami structures and its application for higher-temperature self-assembly. J Am Chem Soc. Sep. 21, 2011;133(37):14488-91. doi:10.1021/ja204546h. Epub Aug. 29, 2011.
Reif et al., Compact error-resilient computational DNA tiling assemblies. Proceeding DNA'04 Proceedings of the 10th international conference on DNA computing. 2004:293-307.
Reif et al., Complexity of graph self-assembly in accretive systems and self-destructible systems. Journal Theoretical Computer Science. 2011;412(17):1592-605.
Rothemund et al., Algorithmic Self-Assembly of DNA Sierpinski Triangles. PLoS Biology. 2004. 2004;2(12):e424. doi:10.1371/journal.pbio.0020424.
Rothemund et al., Design and characterization of programmable DNA nanotubes. J Am Chem. Soc. Dec. 22, 2004;126(50):16344-52. Erratum in: J Am Chem Soc. Feb. 20, 2013;135(7):2864.
Rothemund et al., The program-size complexity of self-assembled squares. Extended Abstract. Proceeding STOC '00 Proceedings of the thirty-second annual ACM symposium on Theory of computing. ACM 2000:459-68.
Rothemund, Folding DNA to create nanoscale shapes and patterns. Nature. Mar. 16, 2006;440(7082):297-302.
Sahu et al., A self-assembly model of time-dependent glue strength. DNA'05 Proceedings of the 11th international conference on DNA Computing. 2005:290-304.
Schmied et al., DNA origami nanopillars as standards for three-dimensional superresolution microscopy. Nano Lett. Feb. 13, 2013;13(2):781-5. doi: 10.1021/nl304492y. Epub Feb. 5, 2013.
Schulman et al., Synthesis of crystals with a programmable kinetic barrier to nucleation. Proc. Natl Acad Sci U S A. Sep. 25, 2007;104(39):15236-41. Epub Sep. 19, 2007.
Schweller et al., Multiplexed in situ immunofluorescence using dynamic DNA complexes. Angew Chem Int Ed Engl. Sep. 10, 2012;51(37):9292-6. doi: 10.1002/anie.201204304. Epub Aug. 15, 2012.
Seelig et al., Enzyme-free nucleic acid logic circuits. Science. Dec. 8, 2006;314(5805):1585-8.
Seeman et al., Nucleic acid nanostructures: Bottom-up control of geometry on the nanoscale. Rep. Prog. Phys, 2005, 68: 237-70.
Seeman, De novo design of sequences for nucleic acid structural engineering. J Biomol Struct Dyn. Dec. 1990;8(3):573-81.
Seeman, DNA in a material world. Nature. Jan. 23, 2003;421(6921):427-31.
Seeman, Nanomaterials based on DNA. Annu Rev Biochem. 2010;79:65-87. doi:10.1146/annurev-biochem-060308-102244.
Seeman, Nucleic acid junctions and lattices. J Theor Biol. Nov. 21, 1982;99(2):237-47.
Sekulić et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.
Sharma et al., Control of self-assembly of DNA tubules through integration of gold nanoparticles. Science. Jan. 2, 2009;323(5910):112-6. doi: 10.1126/science.1165831.
Sharma et al., DNA-tile-directed self-assembly of quantum dots into two-dimensional nanopatterns. Angew Chem Int Ed Engl. 2008;47(28):5157-9. doi:10.1002/anie.200801485.
Sharma et al., Toward reliable gold nanoparticle patterning on self-assembled DNA nanoscaffold. J Am Chem Soc. Jun. 25, 2008;130(25):7820-1. doi: 10.1021/ja802853r. Epub May 30, 2008.
Sharonov et al., Wide-field subdiffraction imaging by accumulated binding of diffusing probes. Proc Natl Acad Sci U S A. Dec. 12, 2006;103(50):18911-6. Epub Dec. 1, 2006.
Sherman et al., A Precisely Controlled DNA Biped Walking Device. Nano Letters. 2004;4(7):1203-7.
Shih et al., A 1.7-kilobase single-stranded DNA that folds into a nanoscale octahedron. Nature. Feb. 12, 2004;427(6975):618-21.
Shih et al., Knitting complex weaves with DNA origami. Curr Opin Struct Biol. Jun. 2010;20(3):276-82. doi: 10.1016/j.sbi.2010.03.009. Epub Apr. 22, 2010.
Shtengel et al., Interferometric fluorescent super-resolution microscopy resolves 3D cellular ultrastructure. Proc Natl Acad Sci U S A. Mar. 3, 2009;106(9):3125-30. doi:10.1073/pnas.0813131106. Epub Feb. 6, 2009.
Smith et al., A structurally variable hinged tetrahedron framework from DNA origami. J Nucleic Acids. 2011;2011:360954. doi: 10.4061/2011/360954. Epub Sep. 18, 2011.
Tang et al., Evolution of block copolymer lithography to highly ordered square arrays. Science. Oct. 17, 2008;322(5900):429-32. doi: 10.1126/science.1162950. Epub Sep. 25, 2008.
Tavakkoli et al., Templating three-dimensional self-assembled structures in bilayer block copolymer films. Science. Jun. 8, 2012;336(6086):1294-8. doi: 10.1126/science.1218437.
Tørring et al., DNA origami: a quantum leap for self-assembly of complex structures. Chem Soc Rev. Dec. 2011;40(12):5636-46. doi: 10.1039/c1cs15057j. Epub May 19, 2011.
Venkataraman et al., Selective cell death mediated by small conditional RNAs. Proc Natl Acad Sci U S A. Sep. 28, 2010;107(39):16777-82. doi: 10.1073/pnas.1006377107. Epub Sep.

(56) References Cited

OTHER PUBLICATIONS 7, 2010. Retraction in: Dirks RM, Ueda CT, Pierce NA. Proc Natl Acad Sci U S A. Jan. 2, 2013;110(1):384.
Wei et al., Complex shapes self-assembled from single-stranded DNA tiles. Nature. May 30, 2012;485(7400):623-6. doi: 10.1038/nature11075.
Wei et al., Uniquimer: Software of De Novo DNA Sequence Generation for DNA Self-Assembly—An Introduction and the Related Applications in DNA Self-Assembly. J Comput Theor Nanosci. 2007;4(1):133-41.
Winfree et al., Design and self-assembly of two-dimensional DNA crystals. Nature. Aug. 6, 1998;394(6693):539-44.
Winfree, Algorithmic Self-Assembly of DNA. Doctoral Thesis. California Institute of Technology. Mar. 1998.
Woo et al., Programmable molecular recognition based on the geometry of DNA nanostructures. Nat Chem. Jul. 10, 2011;3(8):620-7. doi: 10.1038/nchem.1070. Erratum in: Nat Chem. Oct. 2011;3(10):829. Nat Chem. 2011;3(8):following 627.
Yan et al., A robust DNA mechanical device controlled by hybridization topology. Nature. Jan. 3, 2002;415(6867):62-5.
Yan et al., Directed nucleation assembly of DNA tile complexes for barcode-patterned lattices. Proc Natl Acad Sci U S A. Jul. 8, 2003;100(14):8103-8. Epub Jun. 23, 2003.
Yan et al., DNA-templated self-assembly of protein arrays and highly conductive nanowires. Science. Sep. 26, 2003;301(5641):1882-4.
Yang et al., Artificially expanded genetic information system: a new base pair with an alternative hydrogen bonding pattern. Nucleic Acids Res. 2006;34(21):6095-101. Epub Oct. 29, 2006.
Yang et al., Metal-nucleic acid cages. Nat Chem. Aug. 2009;1(5):390-6. doi: 10.1038/nchem.290.
Yevdokimov et al., Nanoconstructions based on double-stranded nucleic acids. Int J Biol Macromol. Jul. 2005;36(1-2):103-15.
Yin et al., A unidirectional DNA walker that moves autonomously along a track. Angew Chem Int Ed Engl. Sep. 20, 2004;43(37):4906-11.
Yin et al., Designs of autonomous unidirectional walking DNA devices. Proceeding DNA'04 Proceedings of the 10th international conference on DNA computing. 2004:410-25.
Yin et al., Programming biomolecular self-assembly pathways. Nature. Jan. 17, 2008;451(7176):318-22. doi: 10.1038/nature06451.
Yin et al., Programming DNA tube circumferences. Science. Aug. 8, 2008;321(5890):824-6.
Yin et al., Theoretical and practical advances in genome halving. Bioinformatics. Apr. 1, 2005;21(7):869-79. Epub Oct. 28, 2004.
Yurke et al., A DNA-fuelled molecular machine made of DNA. Nature. Aug. 10, 2000;406(6796):605-8.
Zhang et al., Conformational flexibility facilitates self-assembly of complex DNA nanostructures. Proc Natl Acad Sci U S A. Aug. 5, 2008;105(31):10665-9. doi:10.1073/pnas.0803841105. Epub Jul. 30, 2008.
Zhang et al., Construction of a DNA-Truncated Octahedron. J Am Chem Soc 1994;116(5):1661-9.
Zhang et al., Symmetry controls the face geometry of DNA polyhedra. J Am Chem Soc. Feb. 4, 2009;131(4):1413-5. doi:10.1021/ja809666h.
Zhao et al., Organizing DNA origami tiles into larger structures using preformed scaffold frames. Nano Lett. Jul. 13, 2011;11(7):2997-3002. doi:10.1021/nl201603a. Epub Jun. 23, 2011.
Zheng et al., From molecular to macroscopic via the rational design of a self-assembled 3D DNA crystal. Nature. Sep. 3, 2009;461(7260):74-7. doi:10.1038/nature08274.
Zimmermann et al., Self-assembly of a DNA dodecahedron from 20 trisoligonucleotides with C(3h) linkers. Angew Chem Int Ed Engl. 2008;47(19):3626-30. doi: 10.1002/anie.200702682.
Jones et al., Nanomaterials. Programmable materials and the nature of the DNA bond. Science. Feb. 20, 2015;347(6224):1260901. doi:10.1126/science.1260901.
Ke et al., DNA brick crystals with prescribed depths. Nat Chem. Nov. 2014;6(11):994-1002. doi: 10.1038/nchem.2083. Epub Oct. 19, 2014.
Ke, Designer three-dimensional DNA architectures. Curr Opin Struct Biol. Aug. 2014;27:122-8. doi: 10.1016/j.sbi.2014.07.010. Epub Aug. 11, 2014.
Li et al., A replicable tetrahedral nanostructure self-assembled from a single DNA strand. J Am Chem Soc. Sep. 16, 2009;131(36):13093-8. doi: 10.1021/ja903768f.
Ma et al., Biotemplated nanostructures: directed assembly of electronic and optical materials using nanoscale complementarity. Journal of Materials Chemistry. 2008;18(9):954-64.
Monson et al., DNA-Templated Constructed of Copper Nanowires. Nano Letters. 2003;3(2):359-63. Epub Feb. 14, 2003.
Pinheiro et al., Challenges and opportunities for structural DNA nanotechnology. Nat Nanotechnol. Nov. 6, 2011;6(12):763-72. doi:10.1038/nnano.2011.187.
Xiao et al., Selfassembly of Metallic Nanoparticle Arrays by DNA Scaffolding. Journal of Nanoparticle Research. Aug. 1, 2002;4:313-7.
Zhang et al., Structural DNA nanotechnology: state of the art and future perspective. J Am Chem Soc. Aug. 13, 2014;136(32):11198-211. doi:10.1021/ja505101a. Epub Jul. 28, 2014.
Alexander et al., On Types of Knotted Curves. Annals of Mathematics 1926-1927, 28(1/4): 562-586.
Alexander, Topical Invariants of Knots and Links. Transactions of the American Mathematical Society 1928, 30(2): 275-306.
Anthony, MIT and Harvard engineers create graphene electronics with DNA based lithography. Extremetech.com. Apr. 10, 2013. http://www.extremetech.com/computing/153046-mit-and-harvard-engineers-create-graphene-electronics-with-dna-based-lithography.
Cataldo et al., DNA degradation with ozone. Int J Biol Macromol. May 30, 2006;38(3-5):248-54. Epub Apr. 17, 2006.
Dimitrakakis et al., Top-down patterning of zeolitic imidazolate framework composite thin films by deep X-ray lithography. Chem Commun (Camb). Aug. 4, 2012;48(60):7483-5. doi: 10.1039/c2cc33292b. Epub Jun. 22, 2012.
Han et al., Unidirectional scaffold-strand arrangement in DNA origami. Angew Chem Int Ed Engl. Aug. 19, 2013;52(34):9031-4. doi: 10.1002/anie.201302177. Epub Jul. 14, 2013.
Horiya et al., RNA LEGO: magnesium-dependent formation of specific RNA assemblies through kissing interactions. Chem Biol. Jul. 2003;10(7):645-54.
Jin et al., Metallized DNA nanolithography for encoding and transferring spatial information for graphene patterning. Nat Commun. 2013;4:1663. doi: 10.1038/ncomms2690.
Jungmann et al., DNA origami-based nanoribbons: assembly, length distribution, and twist. Nanotechnology. Jul. 8, 2011;22(27):275301. doi: 10.1088/0957-4484/22/27/275301. Epub May 20, 2011.
Ke et al., A study of DNA tube formation mechanisms using 4-, 8-, and 12-helix DNA nanostructures. J Am Chem Soc. Apr. 5, 2006;128(13):4414-21.
Lee et al., Rate and molecular spectrum of spontaneous mutations in the bacterium *Escherichia coli* as determined by whole-genome sequencing. Proc Natl Acad Sci U S A. Oct. 9, 2012;109(41):E2774-83. doi: 10.1073/pnas.1210309109. Epub Sep. 18, 2012.
Lin et al., In vivo cloning of artificial DNA nanostructures. Proc Natl Acad Sci U S A. Nov. 18, 2008;105(46):17626-31. doi: 10.1073/pnas.0805416105. Epub Oct. 16, 2008.
Mansfield, Are there knots in proteins? Nat Struct Biol. Apr. 1994;1(4):213-4.
Mao et al, Designed Two-Dimensional DNA Holliday Junction Arrays Visualized by Atomic Force Microscopy. J. Am. Chem. Soc., 1999, 121 (23), pp. 5437-5443.
Marchi et al, Toward larger DNA origami. Nano Lett. Oct. 8, 2014;14(10):5740-7. doi: 10.1021/nl502626s. Epub Sep. 8, 2014.
Matsui et al., Focused ion beam applications to solid state devices. Nanotechnology 1996, 7(3):247.
Petty et al., DNA-templated Ag nanocluster formation. J Am Chem Soc. Apr. 28, 2004;126(16):5207-12.
Piner et al,. "Dip-Pen" nanolithography. Science. Jan. 29, 1999;283(5402):661-3.

(56) References Cited

OTHER PUBLICATIONS

Rajesh et al,. Carbon Nanotubes Generated from Template Carbonization of Polyphenyl Acetylene as the Support for Electrooxidation of Methanol. J. Phys. Chem. B, 2003, 107 (12), pp. 2701-2708.
Randolph et al., Focused, Nanoscale Electron-Beam-Induced Deposition and Etching. Critical Reviews in Solid State and Material Sciences, 2006, 31(3):55-89.
Ravanat et al., Direct and indirect effects of UV radiation on DNA and its components. J Photochem Photobiol B. Oct. 2001;63(1-3):88-102.
Scheible et al., A Compact DNA Cube with Side Length 10 nm. Small. Oct. 21, 2015;11(39):5200-5. doi: 10.1002/smll. 201501370. Epub Aug. 21, 2015.
Seeman et al., The design and engineering of nucleic acid nanoscale assemblies. Curr Opin Struct Biol. Aug. 1996;6(4):519-26.
Surwade et al., Molecular lithography through DNA-mediated etching and masking of SiO2. J Am Chem Soc. Aug. 10, 2011;133(31):11868-71. doi: 10.1021/ja2038886. Epub Jul. 19, 2011.
Surwade et al., Nanoscale growth and patterning of inorganic oxides using DNA nanostructure templates. J Am Chem Soc. May 8, 2013;135(18):6778-81. doi: 10.1021/ja401785h. Epub Apr. 25, 2013.
Takusagawa et al., A Real Knot in Protein. J. Am. Chem. Soc., 1996, 118 (37), pp. 8945-8946.
Taylor, A deeply knotted protein structure and how it might fold. Nature. Aug. 24, 2000;406(6798):916-9.
Wagner et al., A light-sensing knot revealed by the structure of the chromophore-binding domain of phytochrome. Nature. Nov. 17, 2005;438(7066):325-31.
Williams et al,. Tiamat: A Three-Dimensional Editing Tool for Complex DNA Structures. DNA Computing 2009, 90-101.
Winters et al., Surface science aspects of etching reactions. Surface Science Reports. 1992, 14(4-6): 162-269.
Wu et al., High aspect ratio silicon etch: A review. Journal of Applied Physics, 2010, 108(5): 051101-051101-20.
Yang et al., DNA Origami with Double-Stranded DNA As a Unified Scaffold. ACS Nano, 2012, 6(9): 8209-8215.
Bertrand et al., Flexibility of the B-DNA backbone: effects of local and neighbouring sequences on pyrimidine-purine steps. Nucleic Acids Res. Mar. 1, 1998;26(5):1261-7.
Fratini et al., Reversible bending and helix geometry in a B-DNA dodecamer: CGCGAATTBrCGCG. J Biol Chem. Dec. 25, 1982;257(24):14686-707.
PCT/US2015/032198, dated Dec. 11, 2015, International Search Report and Written Opinion.
PCT/US2016/020893, dated May 31, 2016, International Search Report and Written Opinion.
Pending U.S. Appl. No. 14/417,390, filed Jan. 26, 2015.
EP 12821431.9, dated Mar. 5, 2015, Extended European Search Report.
PCT/US2012/049306, dated Nov. 22, 2012, International Search Report and Written Opinion.
PCT/US2012/049306, dated Feb. 20, 2014, International Preliminary Report on Patentability.
PCT/US2013/051891, dated Oct. 25, 2013, International Search Report and Written Opinion.
PCT/US2013/051891, dated Feb. 5, 2015, International Preliminary Report on Patentability.
PCT/US2013/068741, dated Feb. 20, 2014, International Search Report and Written Opinion.
Pending U.S. Appl. No. 15/312,854, filed Nov. 21, 2016.
PCT/US2015/032198, dated Dec. 1, 2016, International Preliminary Report on Patentability.

* cited by examiner a
four double helices square b
eight double helices square

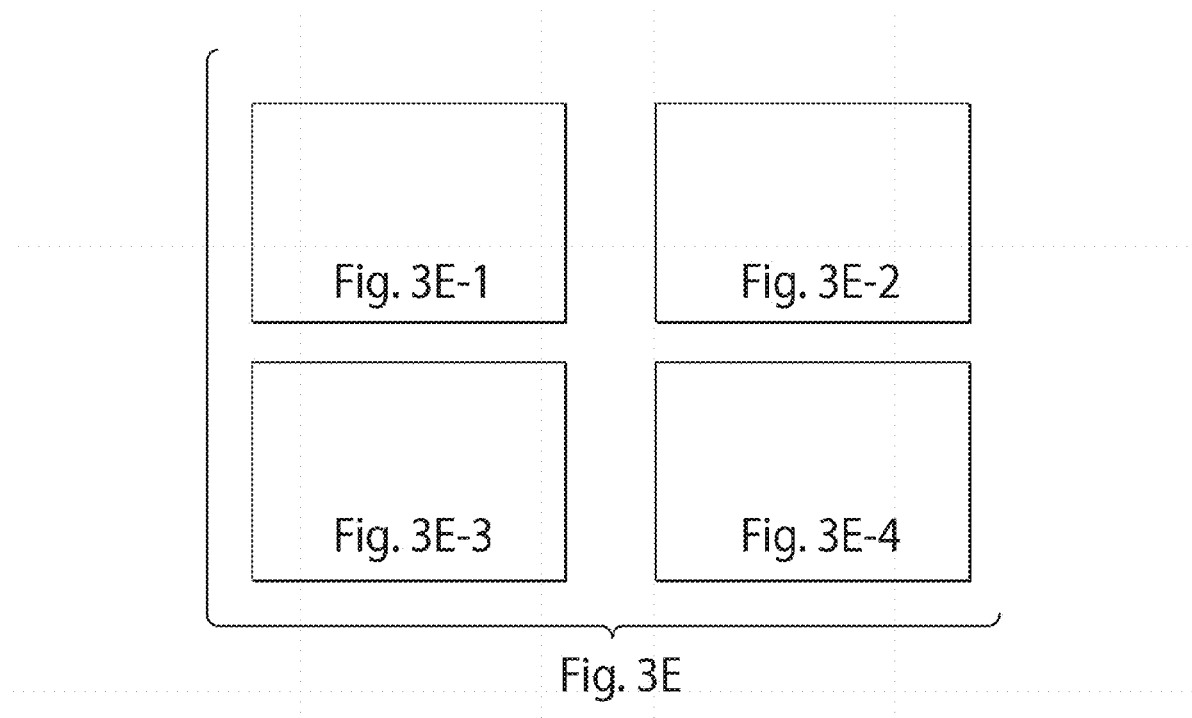

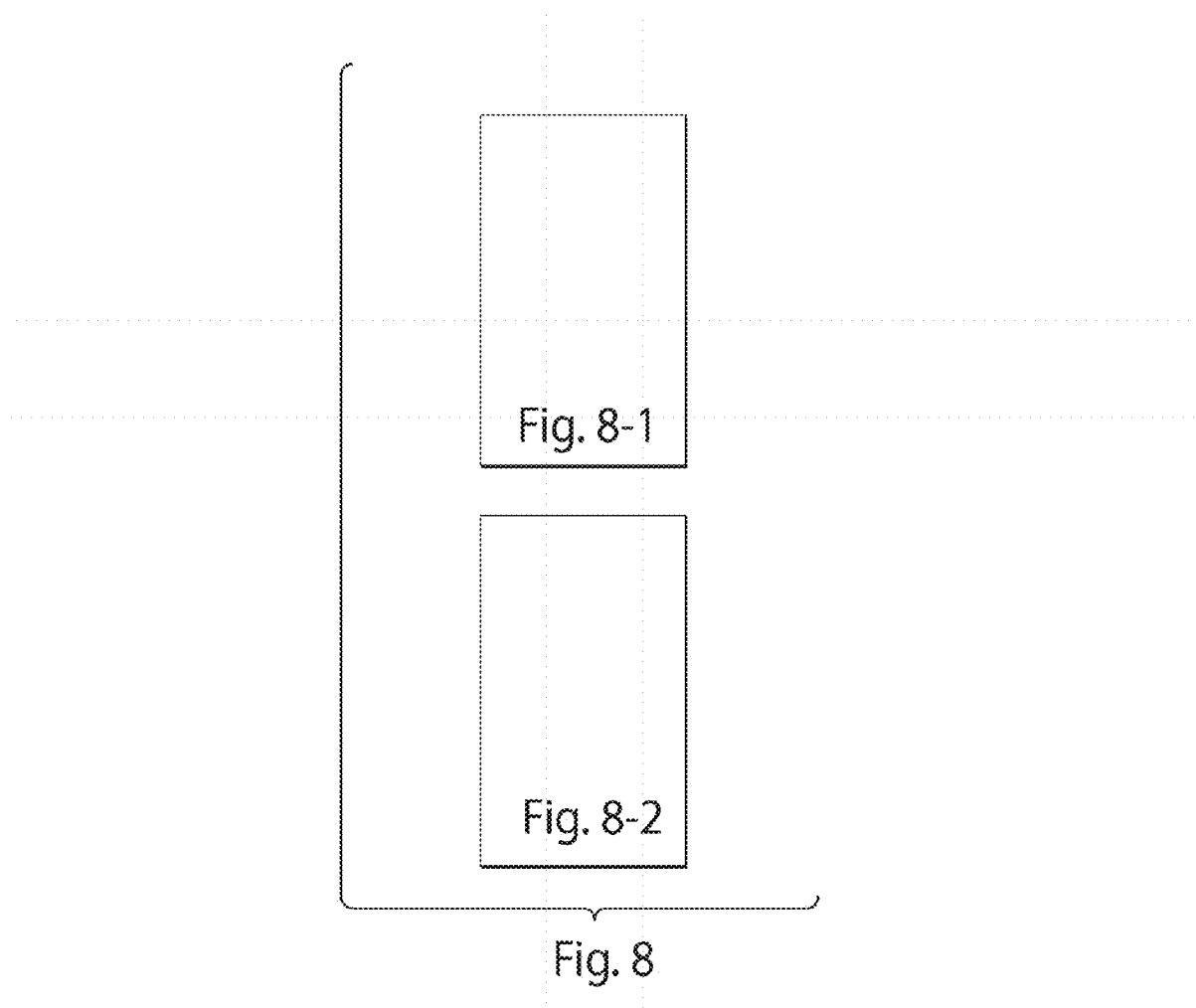

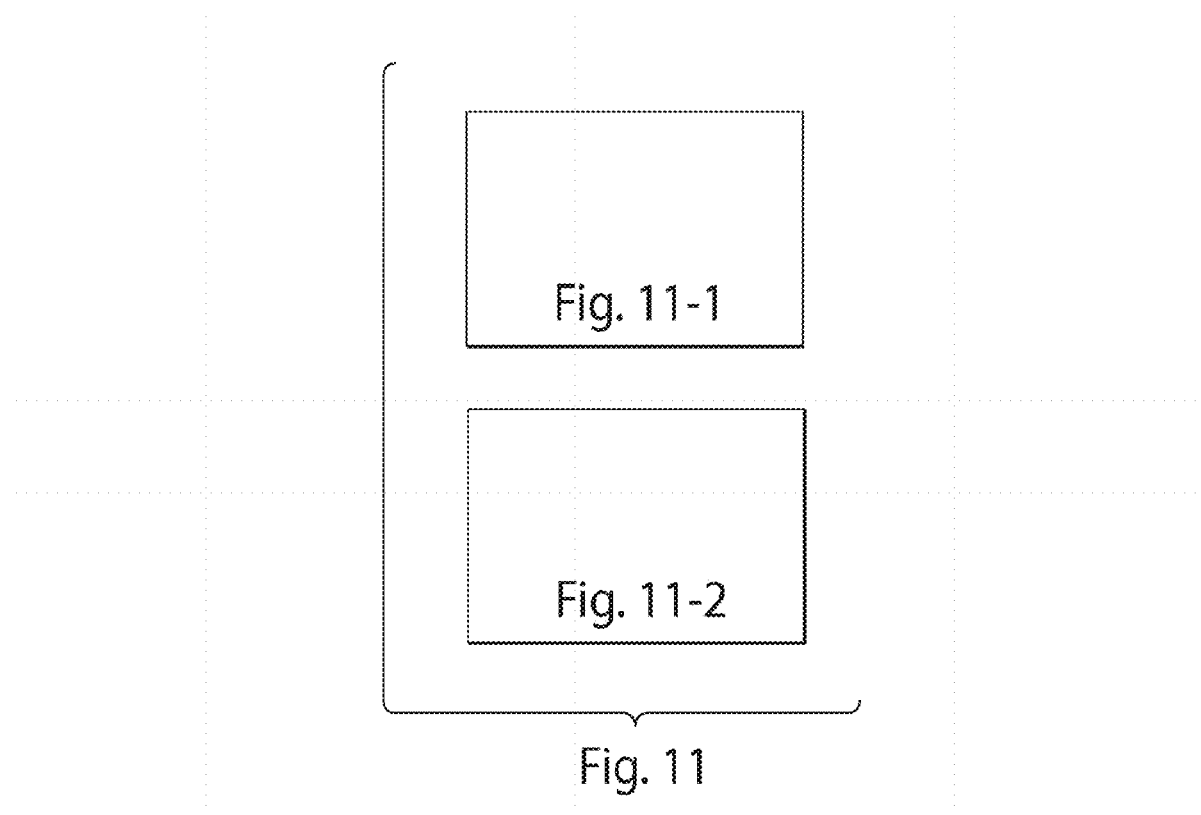

SEQUENCE LISTING

```
<160> NUMBER OF SEQ ID NOS: 364

<210> SEQ ID NO 1
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 1
cagggtggta ctatttatcg t                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
cctccgggca ctcagcttac t                                              21

<210> SEQ ID NO 3
<211> LENGTH: 21
<212> TYPE: DNA
<213> ORGANISM: Artificial Sequence
<220> FEATURE:
<223> OTHER INFORMATION: synthetic oligonucleotide
```

-continued

```
<400> SEQUENCE: 3
caaccgatct ctggataata t                                              21

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
cccgtcaaag cttatatttc t                                              21

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
ctatttagaa ctccaggaag t                                              21

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
ccaggcccac ctatatggat t                                              21

<210> SEQ ID NO 7
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 7
cttaaaggct ctggttgaag t                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 8
cagatcacga ctaacacacc t                                              21

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
cgcctctatc ctgtgaacac t                                              21

<210> SEQ ID NO 10
<211> LENGTH: 21
```

```
<212> TYPE: DNA
<213> ORGANISM: Artificial Sequence
<220> FEATURE:
<223> OTHER INFORMATION: synthetic oligonucleotide

<400> SEQUENCE: 10
cggctgagaa cttaagtttc t                                              21

<210> SEQ ID NO 11
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 11
cggtctcgcc cttagaatga t                                              21

<210> SEQ ID NO 12
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 12
cgggcgccaa ctgaagccct t                                              21

<210> SEQ ID NO 13
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 13
cgggacatcc ctttagtcga t                                              21

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 14
cggagatgcg ctcagatgta t                                              21

<210> SEQ ID NO 15
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 15
tttttttttt tgggtgccca tgtaccaccc tgttttttttt tt                       42

<210> SEQ ID NO 16
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 16
```

```
cgggctggtc tccgaaggac tgtgcccgga ggacgataaa ta                              42
```

<210> SEQ ID NO 17
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 17

```
cgaagtttcc tgcattatga tgagatcggt tgagtaagct ga                              42
```

<210> SEQ ID NO 18
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 18

```
cttcaagtgc tccctgcagc tgctttgacg ggatattatc ca                              42
```

<210> SEQ ID NO 19
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 19

```
cgatttcagc taaagttgtg tgttctaaat agagaaatat aa                              42
```

<210> SEQ ID NO 20
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 20

```
ccaatgcgcc tgcacctgta tggtgggcct ggacttcctg ga                              42
```

<210> SEQ ID NO 21
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 21

```
catcacatcc tcgttcgtac tgagccttta agaatccata ta                              42
```

<210> SEQ ID NO 22
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 22

```
cacagtctgc tactgcagat tgtcgtgatc tgacttcaac ca                              42
```

<210> SEQ ID NO 23
<211> LENGTH: 42
<212> TYPE: DNA
<213> ORGANISM: Artificial Sequence

```
<220> FEATURE:
<223> OTHER INFORMATION: synthetic oligonucleotide

<400> SEQUENCE: 23
cttggatacc tcagtctgac tggatagagg cgaggtgtgt ta              42

<210> SEQ ID NO 24
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 24
caactctagc tcctccgcac tgttctcagc cgagtgttca ca              42

<210> SEQ ID NO 25
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 25
ctcacataac ttccctcttc tgggcgagac cgagaaactt aa              42

<210> SEQ ID NO 26
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 26
cttgcgaggc taaagaatgc tgttggcgcc cgatcattct aa              42

<210> SEQ ID NO 27
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 27
cagcggactc tagtgggcta tgggatgtcc cgaagggctt ca              42

<210> SEQ ID NO 28
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 28
catcgtgtgc ttattcctct tgcgcatctc cgatcgacta aa              42

<210> SEQ ID NO 29
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 29
cctatttgtc tttttttttt tttttttttt ttatacatct ga              42
```

```
<210> SEQ ID NO 30
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 30
cgccgcgtgt ctatcgtggt tgaccagccc gatgggcacc ca                          42

<210> SEQ ID NO 31
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 31
ccattagggc ctaagcagcc tggaaacttc gagtccttcg ga                          42

<210> SEQ ID NO 32
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 32
catatatcga ctcgtcaagg tgcacttgaa gatcataatg ca                          42

<210> SEQ ID NO 33
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 33
cgaaagttgg ctaaacgaca tgctgaaatc gagctgcagg ga                          42

<210> SEQ ID NO 34
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 34
catacggttt ctagaaagat tggcgcattg gacacaactt ta                          42

<210> SEQ ID NO 35
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 35
caaggctcgg cttatgcaat tggatgtgat gatacaggtg ca                          42

<210> SEQ ID NO 36
<211> LENGTH: 42
<212> TYPE: DNA
<213> ORGANISM: Artificial Sequence
<220> FEATURE:
<223> OTHER INFORMATION: synthetic oligonucleotide
```

<400> SEQUENCE: 36
caacttagct ctgaaagtcg tgcagactgt gagtacgaac ga         42

<210> SEQ ID NO 37
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 37
cacttcccat ctaaaccagg tggtatccaa gaatctgcag ta         42

<210> SEQ ID NO 38
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 38
caagtccgcg ctcgtcagat tgctagagtt gagtcagact ga         42

<210> SEQ ID NO 39
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 39
cgtgtagaat ctagagctga tgttatgtga gagtgcggag ga         42

<210> SEQ ID NO 40
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 40
cagctgagag ctttggtcgg tgcctcgcaa gagaagaggg aa         42

<210> SEQ ID NO 41
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 41
catcttaggg ctgctgtgta tgagtccgct gagcattctt ta         42

<210> SEQ ID NO 42
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 42
cctttctcga ctctgaagtg tgcacacgat gatagcccac ta         42

<210> SEQ ID NO 43

```
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 43
cgccctgttt ctgagtccct tgacaaatag gaagaggaat aa                              42

<210> SEQ ID NO 44
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 44
tttttttttt tgggagtgga tgacacgcgg cgttttttt tt                              42

<210> SEQ ID NO 45
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 45
caggctctac tgggaggata tggccctaat ggaaccacga ta                             42

<210> SEQ ID NO 46
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 46
cgcgctagac tacatttata tgtcgatata tgaggctgct ta                             42

<210> SEQ ID NO 47
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 47
ctacgctatc tttaccatta tgccaacttt cgaccttgac ga                             42

<210> SEQ ID NO 48
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 48
cggagtaaac ttgtgccttg tgaaaccgta tgatgtcgtt ta                             42

<210> SEQ ID NO 49
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 49
```
cagataaagc tactagcatt tgccgagcct tgaatctttc ta                             42

<210> SEQ ID NO 50
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 50
cgcctccttc tcaataataa tgagctaagt tgaattgcat aa                             42

<210> SEQ ID NO 51
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 51
ccaactaggc tggaccatcg tgatgggaag tgacgacttt ca                             42

<210> SEQ ID NO 52
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 52
ctaatgatgc taatgaacta tgcgcggact tgacctggtt ta                             42

<210> SEQ ID NO 53
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 53
ccgccagtac taaatacctg tgattctaca cgaatctgac ga                             42

<210> SEQ ID NO 54
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 54
cgtggcgttc taccattgtt tgctctcagc tgatcagctc ta                             42

<210> SEQ ID NO 55
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 55
cactttattc tatgagttaa tgccctaaga tgaccgacca aa                             42

<210> SEQ ID NO 56
<211> LENGTH: 42
<212> TYPE: DNA

<213> ORGANISM: Artificial Sequence
<220> FEATURE:
<223> OTHER INFORMATION: synthetic oligonucleotide

<400> SEQUENCE: 56
cccgaccgtc tgccctcgct tgtcgagaaa ggatacacag ca        42

<210> SEQ ID NO 57
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 57
cggatttgac tcacagagac tgaaacaggg cgacacttca ga        42

<210> SEQ ID NO 58
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 58
catgctcgcc tttttttttt tttttttttt ttaagggact ca        42

<210> SEQ ID NO 59
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 59
cggacttcat ctatggttta tgtagagcct gatccactcc ca        42

<210> SEQ ID NO 60
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 60
ccgttgatga ctgggcggat tgtctagcgc gatatcctcc ca        42

<210> SEQ ID NO 61
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 61
ctaatgggac ctctggtccc tgatagcgta gatataaatg ta        42

<210> SEQ ID NO 62
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 62
ccacttcctt cttggttgcg tgtttactcc gataatggta aa        42

<210> SEQ ID NO 63
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 63
cagtacatag ctaggatgca tgctttatct gacaaggcac aa        42

<210> SEQ ID NO 64
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 64
cgaagggagc ctggcatttg tgaaggaggc gaaatgctag ta        42

<210> SEQ ID NO 65
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 65
cgccaagtag ctagtccgca tgcctagttg gattattatt ga        42

<210> SEQ ID NO 66
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 66
ctagcagcat ctaatccatt tgcatcatta gacgatggtc ca        42

<210> SEQ ID NO 67
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 67
caagcgcgta cttacctgac tgtactggcg gatagttcat ta        42

<210> SEQ ID NO 68
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 68
ccctgcgcac cttcgccacg tgaacgccac gacaggtatt ta        42

<210> SEQ ID NO 69
<211> LENGTH: 42
<212> TYPE: DNA
<213> ORGANISM: Artificial Sequence
<220> FEATURE:

<223> OTHER INFORMATION: synthetic oligonucleotide

<400> SEQUENCE: 69
ccctaaccct ctttaggtac tgaataaagt gaaacaatgg ta                              42

<210> SEQ ID NO 70
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 70
ctgcaaacat cttactgacc tgacggtcgg gattaactca ta                              42

<210> SEQ ID NO 71
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 71
catggtacgg ctaacatatc tgtcaaatcc gaagcgaggg ca                              42

<210> SEQ ID NO 72
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 72
catgcggctg ctaccgggca tggcgagcat gagtctctgt ga                              42

<210> SEQ ID NO 73
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 73
tttttttttt tggaggattc tgatgaagtc cgtttttttt tt                              42

<210> SEQ ID NO 74
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 74
cccgtggtcc tcgcccgaaa tgtcatcaac ggataaacca ta                              42

<210> SEQ ID NO 75
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 75
ctttattggc ttctcagtta tggtcccatt agaatccgcc ca                              42

<210> SEQ ID NO 76
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 76
cactagaagc ttaagggtaa tgaaggaagt ggagggacca ga                42

<210> SEQ ID NO 77
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 77
cgcgagagcc ttcctgttat tgctatgtac tgacgcaacc aa                42

<210> SEQ ID NO 78
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 78
cgcgtccttc tacggcgaga tggctccctt cgatgcatcc ta                42

<210> SEQ ID NO 79
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 79
ccagttagtc tcaatgcagt tgctacttgg cgacaaatgc ca                42

<210> SEQ ID NO 80
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 80
ccaatactcc tcggaggcag tgatgctgct agatgcggac ta                42

<210> SEQ ID NO 81
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 81
ccaatcggcc tgcaggctgt tgtacgcgct tgaaatggat ta                42

<210> SEQ ID NO 82
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 82
ccctatattc tcttgggcaa tggtgcgcag ggagtcaggt aa           42

<210> SEQ ID NO 83
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 83
cggtggccgc tacaaccaat tgagggttag ggacgtggcg aa           42

<210> SEQ ID NO 84
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 84
ctgttgcttc tttagttctt tgatgtttgc agagtaccta aa           42

<210> SEQ ID NO 85
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 85
cagcgttggc tgaaactcgc tgccgtacca tgaggtcagt aa           42

<210> SEQ ID NO 86
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 86
cgtggtcagc ttgctctagt tgcagccgca tgagatatgt ta           42

<210> SEQ ID NO 87
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 87
ccctgacgcc tttttttttt ttttttttt ttatgcccgg ta            42

<210> SEQ ID NO 88
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 88
cgattggtct ctgagactta tggaccacgg gagaatcctc ca           42

<210> SEQ ID NO 89
<211> LENGTH: 42

```
<212> TYPE: DNA
<213> ORGANISM: Artificial Sequence
<220> FEATURE:
<223> OTHER INFORMATION: synthetic oligonucleotide

<400> SEQUENCE: 89
cgggccggct ctattgacaa tgccaataaa gatttcgggc ga                              42

<210> SEQ ID NO 90
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 90
cagaggatgg ctttccgatg tgcttctagt gataactgag aa                              42

<210> SEQ ID NO 91
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 91
caccaaaggg ctcaacaact tggctctcgc gattacccTt aa                              42

<210> SEQ ID NO 92
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 92
cttgttcaga ctcgaattcc tgaaggacgc gaataacagg aa                              42

<210> SEQ ID NO 93
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 93
cagagcatcc ctacagatgc tgactaactg gatctcgccg ta                              42

<210> SEQ ID NO 94
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 94
cgtactggtt ctgacaggtc tggagtattg gaactgcatt ga                              42

<210> SEQ ID NO 95
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 95
```
cctcggacgc ctaacttctg tggccgattg gactgcctcc ga         42

<210> SEQ ID NO 96
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 96
ccaccaaact ctatagcccg tgaatatagg aacagcctg ca         42

<210> SEQ ID NO 97
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 97
catgagtgaa ctgttaggtc tgcggccacc gattgcccaa ga         42

<210> SEQ ID NO 98
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 98
ctagagtaca ctacccgcat tgaagcaaca gaattggttg ta         42

<210> SEQ ID NO 99
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 99
cgagaagtat ctatgcaccc tgccaacgct gaaagaacta aa         42

<210> SEQ ID NO 100
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 100
ctattgagga ctatccaatc tgctgaccac gagcgagttt ca         42

<210> SEQ ID NO 101
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 101
ccgactgctg ctgcgaatag tggcgtcagg gaactagagc aa         42

<210> SEQ ID NO 102
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 102
tttttttttt ttgcttgggt tgagaccaat cgttttttt tt                              42

<210> SEQ ID NO 103
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 103
ccgcacagcc tcatccctc tgagccggcc cgataagtct ca                              42

<210> SEQ ID NO 104
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 104
ctaggttccc ttccttataa tgccatcctc tgattgtcaa ta                             42

<210> SEQ ID NO 105
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 105
ctatggctac tcacaaccgt tgccctttgg tgacatcgga aa                             42

<210> SEQ ID NO 106
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 106
cgtgttgtcc tatatcacgc tgtctgaaca agaagttgtt ga                             42

<210> SEQ ID NO 107
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 107
cgagcgtctc ttgttgtctt tgggatgctc tgaggaattc ga                             42

<210> SEQ ID NO 108
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 108
ctgacgctcc tctggaccta tgaaccagta cgagcatctg ta                             42

```
<210> SEQ ID NO 109
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 109
cacatttaac taacttatcc tggcgtccga ggagacctgt ca                          42

<210> SEQ ID NO 110
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 110
caacatacgc ttcgagccag tgagtttggt ggacagaagt ta                          42

<210> SEQ ID NO 111
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 111
caatacttcc tacacctatc tgttcactca tgacgggcta ta                          42

<210> SEQ ID NO 112
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 112
cttccagccc ttaaagcgga tgtgtactct agagacctaa ca                          42

<210> SEQ ID NO 113
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 113
ccctatccac ttagttcgac tgatacttct cgaatgcggg ta                          42

<210> SEQ ID NO 114
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 114
ctccaagccc tcacgaaaca tgtcctcaat agagggtgca ta                          42

<210> SEQ ID NO 115
<211> LENGTH: 42
<212> TYPE: DNA
<213> ORGANISM: Artificial Sequence
<220> FEATURE:
<223> OTHER INFORMATION: synthetic oligonucleotide
```

<400> SEQUENCE: 115
cctacggatc tgatgcacat tgcagcagtc ggagattgga ta          42

<210> SEQ ID NO 116
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 116
ccagcaacgc tttttttttt tttttttttt ttactattcg ca          42

<210> SEQ ID NO 117
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 117
ccttaccgga ctttccgtaa tggctgtgcg gaacccaagc aa          42

<210> SEQ ID NO 118
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 118
cttaccgcgg ctagtgctca tgggaaccta gagagggtat ga          42

<210> SEQ ID NO 119
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 119
cttgatcgaa cttgtcatat tgtagccata gattataagg aa          42

<210> SEQ ID NO 120
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 120
ctggtttgat ctcgtaccaa tggacaacac gaacggttgt ga          42

<210> SEQ ID NO 121
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 121
cccgtgttga ctgcatagta tgagacgctc gagcgtgata ta          42

<210> SEQ ID NO 122

```
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 122
ccgctagatc tccttgtgc tggagcgtca gaaagacaac aa                               42

<210> SEQ ID NO 123
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 123
cgcaggctag cttacgttag tgttaaatgt gataggtcca ga                              42

<210> SEQ ID NO 124
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 124
ctccggtcaa ctagttagta tgcgtatgtt gaggataagt ta                              42

<210> SEQ ID NO 125
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 125
cggtctttaa ctgggattac tggaagtatt gactggctcg aa                              42

<210> SEQ ID NO 126
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 126
cagttcgtca ctggctacct tgggctggaa gagataggtg ta                              42

<210> SEQ ID NO 127
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 127
catactgtct ctaactgcaa tgtggatagg gatccgcttt aa                              42

<210> SEQ ID NO 128
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 128
```

-continued cttggcttta cttatcggcg tgggcttgga gagtcgaact aa  42

<210> SEQ ID NO 129
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 129
cgtaagggca ctatcgttta tgatccgtag gatgtttcgt ga  42

<210> SEQ ID NO 130
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 130
ctcgctttag ctggagaccg tgcgttgctg gaatgtgcat ca  42

<210> SEQ ID NO 131
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 131
tttttttttt tagtgcagaa tgtccggtaa ggttttttttt tt  42

<210> SEQ ID NO 132
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 132
catacctctc ttaggtcaat tgccgcggta agattacgga aa  42

<210> SEQ ID NO 133
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 133
cacaccacac tcagtaggtt tgttcgatca agatgagcac ta  42

<210> SEQ ID NO 134
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 134
ccacgcagtc tggtcatcac tgatcaaacc agaatatgac aa  42

<210> SEQ ID NO 135
<211> LENGTH: 42
<212> TYPE: DNA

<213> ORGANISM: Artificial Sequence
<220> FEATURE:
<223> OTHER INFORMATION: synthetic oligonucleotide

<400> SEQUENCE: 135
caacgcaagc tttctgatta tgtcaacacg ggattggtac ga    42

<210> SEQ ID NO 136
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 136
cgtagtggcc ttactagggt tggatctagc ggatactatg ca    42

<210> SEQ ID NO 137
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 137
ctcgtggaac tcagggctcg tgctagcctg cgagcacaag ga    42

<210> SEQ ID NO 138
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 138
caccgccctc ttacgcccac tgttgaccgg agactaacgt aa    42

<210> SEQ ID NO 139
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 139
cgaattaaac tagacgagta tgttaaagac cgatactaac ta    42

<210> SEQ ID NO 140
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 140
cataagcgac tttgatcggc tgtgacgaac tgagtaatcc ca    42

<210> SEQ ID NO 141
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 141
catgcaaccc tgtaagcaaa tgagacagta tgaaggtagc ca    42

<210> SEQ ID NO 142
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 142
cactactggc ttgtaagcgc tgtaaagcca agattgcagt ta        42

<210> SEQ ID NO 143
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 143
ctgtaaggtc tcgagatgtg tgtgcccttviewed cgacgccgat aa        42

<210> SEQ ID NO 144
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 144
ccgtctaacc tataatattg tgctaaagcg agataaacga ta        42

<210> SEQ ID NO 145
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 145
cggcaacgtc ttttttttttt tttttttttt ttacggtctc ca        42

<210> SEQ ID NO 146
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 146
cctttgcttc cttgaccaag tgagaggtat gattctgcac ta        42

<210> SEQ ID NO 147
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 147
cgtggaggcg ctcaccctcc tgtgtggtgt gaattgacct aa        42

<210> SEQ ID NO 148
<211> LENGTH: 42
<212> TYPE: DNA
<213> ORGANISM: Artificial Sequence
<220> FEATURE:

<223> OTHER INFORMATION: synthetic oligonucleotide

<400> SEQUENCE: 148
ctcgccaacc cttgtccagg tgactgcgtg gaaacctact ga　　　　　　　　　　42

<210> SEQ ID NO 149
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 149
cgcttcttca ctgcatgcga tgcttgcgtt gagtgatgac ca　　　　　　　　　　42

<210> SEQ ID NO 150
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 150
cagatatagc ctagccctcg tggccactac gataatcaga aa　　　　　　　　　　42

<210> SEQ ID NO 151
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 151
catccgcagc cttacactaa tgttccacga gaaccctagt aa　　　　　　　　　　42

<210> SEQ ID NO 152
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 152
cgatgcagat cttctgcctt tgagggcggt gacgagccct ga　　　　　　　　　　42

<210> SEQ ID NO 153
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 153
caatagccat ctcacttgat tgtttaattc gagtgggcgt aa　　　　　　　　　　42

<210> SEQ ID NO 154
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 154
cgtccttgga ctcaacgtcc tgtcgcttat gatactcgtc ta　　　　　　　　　　42

<210> SEQ ID NO 155
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 155
ctgcgaaggc ctacaggcac tgggttgcat gagccgatca aa         42

<210> SEQ ID NO 156
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 156
cttcttcgaa ctggacatct tgccagtagt gatttgctta ca         42

<210> SEQ ID NO 157
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 157
cagtcgtgtc cttatgacta tgaccttaca gagcgcttac aa         42

<210> SEQ ID NO 158
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 158
cattacatgg ctaatgctga tggttagacg gacacatctc ga         42

<210> SEQ ID NO 159
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 159
ccagcatcca ctgcggtaac tgacgttgcc gacaatatta ta         42

<210> SEQ ID NO 160
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 160
tttttttttt tctgtgcata tggaagcaaa ggttttttttt tt         42

<210> SEQ ID NO 161
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 161
ctggcgacgc tctgaccgtg tgcgcctcca cgacttggtc aa        42

<210> SEQ ID NO 162
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 162
cttggtctac tgtttataga tgggttggcg agaggagggt ga        42

<210> SEQ ID NO 163
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 163
cgcgcgccac tcattaggag tgtgaagaag cgacctggac aa        42

<210> SEQ ID NO 164
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 164
ccagatttac ttgtacccag tggctatatc tgatcgcatg ca        42

<210> SEQ ID NO 165
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 165
cggcgcgctc tgctagctgg tggctgcgga tgacgagggc ta        42

<210> SEQ ID NO 166
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 166
cgcgctccgc tcactcggaa tgatctgcat cgattagtgt aa        42

<210> SEQ ID NO 167
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 167
catcggtacc tttgggcggg tgatggctat tgaaaggcag aa        42

<210> SEQ ID NO 168
<211> LENGTH: 42

```
<212> TYPE: DNA
<213> ORGANISM: Artificial Sequence
<220> FEATURE:
<223> OTHER INFORMATION: synthetic oligonucleotide

<400> SEQUENCE: 168
caaattgatc ttataactac tgtccaagga cgaatcaagt ga                              42

<210> SEQ ID NO 169
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 169
cttcacggac tccggattca tggccttcgc agaggacgtt ga                              42

<210> SEQ ID NO 170
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 170
cgcgcctgac tctggctgta tgttcgaaga agagtgcctg ta                              42

<210> SEQ ID NO 171
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 171
ctcaaacctc tcgtcgagtg tggacacgac tgaagatgtc ca                              42

<210> SEQ ID NO 172
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 172
catacatcac tcgagaatcg tgccatgtaa tgatagtcat aa                              42

<210> SEQ ID NO 173
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 173
ccacgggtgc tgatcgtccg tgtggatgct ggatcagcat ta                              42

<210> SEQ ID NO 174
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 174
```
ccacctcctc tttttttttt tttttttttt ttagttaccg ca          42

<210> SEQ ID NO 175
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 175
cccgaagtac ctctgcagga tgcgtcgcca gatatgcaca ga          42

<210> SEQ ID NO 176
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 176
cgttaccagg ctacgatgag tgtagaccaa gacacggtca ga          42

<210> SEQ ID NO 177
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 177
ctgtcccact ctccttcaaa tgtggcgcgc gatctataaa ca          42

<210> SEQ ID NO 178
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 178
cattatattg ctcctgaggg tgtaaatctg gactcctaat ga          42

<210> SEQ ID NO 179
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 179
cgtgcatgcc ctcccaaact tgagcgcgcc gactgggtac aa          42

<210> SEQ ID NO 180
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 180
cattgcactg ctctaccctt tgcggagcgc gaccagctag ca          42

<210> SEQ ID NO 181
<211> LENGTH: 42
<212> TYPE: DNA
<213> ORGANISM: Artificial Sequence

```
<220> FEATURE:
<223> OTHER INFORMATION: synthetic oligonucleotide

<400> SEQUENCE: 181
cttcatcgac ctgtttaggt tggtaccgat gattccgagt ga                          42

<210> SEQ ID NO 182
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 182
ctaccggcgt ctggacacca tgatcaattt gacccgccca aa                          42

<210> SEQ ID NO 183
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 183
ccgcggtgtg ctgcattcgc tgtccgtgaa gagtagttat aa                          42

<210> SEQ ID NO 184
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 184
cccgaggttc ctgatctcca tgtcaggcgc gatgaatccg ga                          42

<210> SEQ ID NO 185
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 185
catgagcgtg ctacccgtta tgaggtttga gatacagcca ga                          42

<210> SEQ ID NO 186
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 186
ctctggaata ctaagaatgt tgtgatgtat gacactcgac ga                          42

<210> SEQ ID NO 187
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 187
ctattcgttg ctctgtcctg tgcacccgtg gacgattctc ga                          42
```

<210> SEQ ID NO 188
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 188
ccctcgcaga ctcccgacag tgaggaggtg gacggacgat ca                    42

<210> SEQ ID NO 189
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 189
tttttttttt tgttacttga tggtacttcg ggttttttttt tt                   42

<210> SEQ ID NO 190
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 190
ccgatgcgac ttgatatgtc tgcctggtaa cgatcctgca ga                    42

<210> SEQ ID NO 191
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 191
cgctgccagc ttcagggcct tgagtgggac agactcatcg ta                    42

<210> SEQ ID NO 192
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 192
cagaagggtc tgtgtaactg tgcaatataa tgatttgaag ga                    42

<210> SEQ ID NO 193
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 193
cgagcgccgc tgcggctatt tgggcatgca cgaccctcag ga                    42

<210> SEQ ID NO 194
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 194
caggaggctc tccaaccgct tgcagtgcaa tgaagtttgg ga                          42

<210> SEQ ID NO 195
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 195
ctgggacgac tggcacgtca tggtcgatga agaaagggta ga                          42

<210> SEQ ID NO 196
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 196
ctgcaccagc tgcgtcgttg tgacgccggt agaacctaaa ca                          42

<210> SEQ ID NO 197
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 197
caaaggaaac taacagtgtc tgcacaccgc ggatggtgtc ca                          42

<210> SEQ ID NO 198
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 198
ctctgctctc tttactggtg tggaacctcg ggagcgaatg ca                          42

<210> SEQ ID NO 199
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 199
catgtaagac tacgaatcgc tgcacgctca tgatggagat ca                          42

<210> SEQ ID NO 200
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 200
ctttaggaac taatctttgt tgtattccag agataacggg ta                          42

<210> SEQ ID NO 201

<210> SEQ ID NO 201
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 201
cccagcgatc tgttgcatcg tgcaacgaat agaacattct ta                42

<210> SEQ ID NO 202
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 202
cacgaacagc taaccttaac tgtctgcgag ggacaggaca ga                42

<210> SEQ ID NO 203
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 203
ctatagtaac tttttttttt tttttttttt ttactgtcgg ga                42

<210> SEQ ID NO 204
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 204
ctgggcaagc cttattgcga tgtcgcatcg gatcaagtaa ca                42

<210> SEQ ID NO 205
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 205
cgtgcggtcc ctacgcgcag tgctggcagc gagacatatc aa                42

<210> SEQ ID NO 206
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 206
cgcgggccgc ctttcaatta tgacccttct gaaggccctg aa                42

<210> SEQ ID NO 207
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 207

```
ctatcttgta ctgcaccggt tgcggcgctc gacagttaca ca          42
```

<210> SEQ ID NO 208
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 208

```
ccaaaccgtc ctcctacgtt tgagcctcct gaaatagccg ca          42
```

<210> SEQ ID NO 209
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 209

```
catgtcccaa ctggagtctt tgtcgtccca gaagcggttg ga          42
```

<210> SEQ ID NO 210
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 210

```
ccagcgcgtt ctgtgtctta tgctggtgca gatgacgtgc ca          42
```

<210> SEQ ID NO 211
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 211

```
cttgaccgct ctggagattc tgtttccttt gacaacgacg ca          42
```

<210> SEQ ID NO 212
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 212

```
ctgcgggcca ctcgcgccat tgagagcaga gagacactgt ta          42
```

<210> SEQ ID NO 213
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 213

```
ctaccttagt ctaaagtaat tgtcttacat gacaccagta aa          42
```

<210> SEQ ID NO 214
<211> LENGTH: 42
<212> TYPE: DNA

<213> ORGANISM: Artificial Sequence
<220> FEATURE:
<223> OTHER INFORMATION: synthetic oligonucleotide

<400> SEQUENCE: 214
ctacttgctg ctcgttcctc tgttcctaaa gagcgattcg ta                              42

<210> SEQ ID NO 215
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 215
cagtatctgc ctaatttgcg tgatcgctgg gaacaaagat ta                              42

<210> SEQ ID NO 216
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 216
cgctttggca ctagtagcgg tgctgttcgt gacgatgcaa ca                              42

<210> SEQ ID NO 217
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 217
cggtgttgca cttaacagct tgttactata gagttaaggt ta                              42

<210> SEQ ID NO 218
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 218
tttttttttt tggcccatca tggcttgccc agttttttttt tt                             42

<210> SEQ ID NO 219
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 219
caagacatac tattctgtat tgggaccgca cgatcgcaat aa                              42

<210> SEQ ID NO 220
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 220
ctagaccacc tctttctttta tggcggcccg cgactgcgcg ta                             42

<210> SEQ ID NO 221
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 221
cccttgtggc taaggaggtc tgtacaagat agataattga aa          42

<210> SEQ ID NO 222
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 222
caccgaaccc ttccgctcgc tggacggttt ggaaccggtg ca          42

<210> SEQ ID NO 223
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 223
cctgaagttc ttgatcccga tgttgggaca tgaaacgtag ga          42

<210> SEQ ID NO 224
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 224
ctgagtgacc ttccatccat tgaacgcgct ggaaagactc ca          42

<210> SEQ ID NO 225
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 225
ccctcagcac tcacttctgg tgagcggtca agataagaca ca          42

<210> SEQ ID NO 226
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 226
ctggtaggac tccatccgta tgtggcccgc agagaatctc ca          42

<210> SEQ ID NO 227
<211> LENGTH: 42
<212> TYPE: DNA
<213> ORGANISM: Artificial Sequence
<220> FEATURE:

<223> OTHER INFORMATION: synthetic oligonucleotide

<400> SEQUENCE: 227
cgtgccctgc taaaccgcgt tgactaaggt agaatggcgc ga            42

<210> SEQ ID NO 228
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 228
ccaacattac ttccgcggga tgcagcaagt agaattactt ta            42

<210> SEQ ID NO 229
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 229
cgacaaacac ttgcattacg tggcagatac tgagaggaac ga            42

<210> SEQ ID NO 230
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 230
cgcccaccgc taagtgcgtc tgtgccaaag cgacgcaaat ta            42

<210> SEQ ID NO 231
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 231
cgggacgagc tcaacgcttg tgtgcaacac cgaccgctac ta            42

<210> SEQ ID NO 232
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 232
cattgtactc tttttttttt ttttttttt ttaagctgtt aa             42

<210> SEQ ID NO 233
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 233
ctttgggtac ctagacgggt tgtatgtctt gatgatgggc ca            42

<210> SEQ ID NO 234
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 234
cgcatgtccg ctccagaaag tggtggtcta gaatacagaa ta            42

<210> SEQ ID NO 235
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 235
ctaaggacgt ctccaattca tgccacaagg gataaagaaa ga            42

<210> SEQ ID NO 236
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 236
caaatgcata ctttgtttag tgggttcggt gagacctcct ta            42

<210> SEQ ID NO 237
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 237
cacttagagt ctgggcccgg tgaacttcag gagcgagcgg aa            42

<210> SEQ ID NO 238
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 238
ctctcatgta ctatgttcag tggtcactca gatcgggatc aa            42

<210> SEQ ID NO 239
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 239
ccagctgtca ctgcgccacc tgtgctgagg gaatggatgg aa            42

<210> SEQ ID NO 240
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 240
catctgatat ctcggaacga tgtcctacca gaccagaagt ga                42

<210> SEQ ID NO 241
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 241
ctactattgc ctgctcgagg tgcagggcac gatacggatg ga                42

<210> SEQ ID NO 242
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 242
ctgcagaaac ctgctcctcg tgtaatgttg gaacgcggtt ta                42

<210> SEQ ID NO 243
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 243
cttgagggat ctgtaaatta tgtgtttgtc gatcccgcgg aa                42

<210> SEQ ID NO 244
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 244
caggagtcac ctatgctcat tgcggtgggc gacgtaatgc aa                42

<210> SEQ ID NO 245
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 245
caaactacta ctcgcgtaaa tgctcgtccc gagacgcact ta                42

<210> SEQ ID NO 246
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 246
cgaatgggct ctagatgtca tgagtacaat gacaagcgtt ga                42

<210> SEQ ID NO 247
<211> LENGTH: 42

```
<212> TYPE: DNA
<213> ORGANISM: Artificial Sequence
<220> FEATURE:
<223> OTHER INFORMATION: synthetic oligonucleotide

<400> SEQUENCE: 247
tttttttttt ttccagacta tggtacccaa agtttttttt tt                    42

<210> SEQ ID NO 248
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 248
cgttcgcttc tgctgggccg tgcggacatg cgaacccgtc ta                    42

<210> SEQ ID NO 249
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 249
cacccttacc tttctgccaa tgacgtcctt agactttctg ga                    42

<210> SEQ ID NO 250
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 250
cgcctcacac tgtcagagtt tgtatgcatt tgatgaattg ga                    42

<210> SEQ ID NO 251
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 251
ctaacctgcc tgaccgatcg tgactctaag tgactaaaca aa                    42

<210> SEQ ID NO 252
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 252
cgacgatacc taaggcgtgg tgtacatgag agaccgggcc ca                    42

<210> SEQ ID NO 253
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 253
```
cttcgcctgc ttaccatgtc tgtgacagct ggactgaaca ta      42

<210> SEQ ID NO 254
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 254
ctatacggcc tggtggtaat tgatatcaga tgaggtggcg ca      42

<210> SEQ ID NO 255
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 255
cacgcacgcc tatgccttgg tggcaatagt agatcgttcc ga      42

<210> SEQ ID NO 256
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 256
cgacatgtgc tagtgttcgc tggtttctgc agacctcgag ca      42

<210> SEQ ID NO 257
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 257
cactacgttc tcgcacaaag tgatccctca agacgaggag ca      42

<210> SEQ ID NO 258
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 258
ccacagcaac taagtccata tggtgactcc tgataattta ca      42

<210> SEQ ID NO 259
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 259
cttctgcgcc ttgactgtca tgtagtagtt tgaatgagca ta      42

<210> SEQ ID NO 260
<211> LENGTH: 42
<212> TYPE: DNA
<213> ORGANISM: Artificial Sequence

```
<220> FEATURE:
<223> OTHER INFORMATION: synthetic oligonucleotide

<400> SEQUENCE: 260
cgatcaccgc tcgtaaacta tgagcccatt cgatttacgc ga            42

<210> SEQ ID NO 261
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 261
ctaaccgcac tttttttttt tttttttttt ttatgacatc ta            42

<210> SEQ ID NO 262
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 262
ctgagatgat ctcaaacgaa tgaagcgaac gatagtctgg aa            42

<210> SEQ ID NO 263
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 263
cccttcccgc cttaggcggc tggtaagggt gacggcccag ca            42

<210> SEQ ID NO 264
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 264
cctggctagt ctattgttaa tgtgtgaggc gattggcaga aa            42

<210> SEQ ID NO 265
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 265
ctacgtggag ctattaggga tggcaggtta gaaactctga ca            42

<210> SEQ ID NO 266
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 266
ctgacattac ctcacaatcc tggtatcgtc gacgatcggt ca            42
```

<210> SEQ ID NO 267
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 267
ctaggcgttt cttatgtcct tgcaggcgaa gaccacgcct ta        42

<210> SEQ ID NO 268
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 268
cttaaggtgc ctatataatt tggccgtata gagacatggt aa        42

<210> SEQ ID NO 269
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 269
caacactgga ctagaacaac tggcgtgcgt gaattaccac ca        42

<210> SEQ ID NO 270
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 270
ccctcgttta cttcttaggc tgcacatgtc gaccaaggca ta        42

<210> SEQ ID NO 271
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 271
cgacagtcgc ctgtggttag tgaacgtagt gagcgaacac ta        42

<210> SEQ ID NO 272
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 272
ccgtacatct ctaaagcaga tgttgctgtg gactttgtgc ga        42

<210> SEQ ID NO 273
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 273
cggaccaggg ctgggctcga tggcgcagaa gatatggact ta                42

<210> SEQ ID NO 274
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 274
ctcggaagct ctcctacata tgcggtgatc gatgacagtc aa                42

<210> SEQ ID NO 275
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 275
cgcccgggaa cttcggccta tgtgcggtta gatagtttac ga                42

<210> SEQ ID NO 276
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 276
tttttttttt ttaccttgct tgatcatctc agttttttt tt                42

<210> SEQ ID NO 277
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 277
cgcttaagtc ttggcgctaa tggcgggaag ggattcgttt ga                42

<210> SEQ ID NO 278
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 278
ccctaggccc tagctgcatg tgactagcca ggagccgcct aa                42

<210> SEQ ID NO 279
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 279
ctaagccttc tgttaattct tgctccacgt agattaacaa ta                42

<210> SEQ ID NO 280

```
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 280
cgggctccac tgtaagtgct tggtaatgtc agatccctaa ta                              42

<210> SEQ ID NO 281
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 281
ctctgttatc tggtagtagg tgaaacgcct agaggattgt ga                              42

<210> SEQ ID NO 282
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 282
cccgtgcgac tacaattaga tggcacctta agaaggacat aa                              42

<210> SEQ ID NO 283
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 283
caccaacggc taggcacggc tgtccagtgt tgaaattata ta                              42

<210> SEQ ID NO 284
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 284
ctgggcagtc tacgaactct tgtaaacgag ggagttgttc ta                              42

<210> SEQ ID NO 285
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 285
cgagcgatac tcacccattg tggcgactgt cgagcctaag aa                              42

<210> SEQ ID NO 286
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 286
```
cgttatgccc ttcaagatta tgagatgtac ggactaacca ca                             42

<210> SEQ ID NO 287
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 287
ctgaaggtcc tccagagtgc tgccctggtc cgatctgctt ta                             42

<210> SEQ ID NO 288
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 288
cgggctttgc tgagctgtgt tgagcttccg agatcgagcc ca                             42

<210> SEQ ID NO 289
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 289
cggctacttc tgatcttggg tgttcccggg cgatatgtag ga                             42

<210> SEQ ID NO 290
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 290
cgtcatatcc tttttttttt tttttttttt ttataggccg aa                             42

<210> SEQ ID NO 291
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 291
cttgctttgc ctcctaacga tgacttaagc gaagcaaggt aa                             42

<210> SEQ ID NO 292
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 292
caatacaccg ctgcaagacc tgggcctagg gattagcgcc aa                             42

<210> SEQ ID NO 293
<211> LENGTH: 42
<212> TYPE: DNA

```
<213> ORGANISM: Artificial Sequence
<220> FEATURE:
<223> OTHER INFORMATION: synthetic oligonucleotide

<400> SEQUENCE: 293
cttgggacgg ctttggaaat tgaaggctta gacatgcagc ta                                42

<210> SEQ ID NO 294
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 294
ccaattagga ctaatttaga tgtggagccc gaagaattaa ca                                42

<210> SEQ ID NO 295
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 295
ctttggccat cttatccaaa tgataacaga gaagcactta ca                                42

<210> SEQ ID NO 296
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 296
ccctggttat ctcctatcct tgtcgcacgg gacctactac ca                                42

<210> SEQ ID NO 297
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 297
ctattgtcct ctaagggtcc tgccgttggt gatctaattg ta                                42

<210> SEQ ID NO 298
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 298
ctttgcaata ctaccggaac tgactgccca gagccgtgcc ta                                42

<210> SEQ ID NO 299
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 299
cctacagcgt ctatggcaaa tgtatcgctc gaagagttcg ta                                42
```

<210> SEQ ID NO 300
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 300
cggatcacct ctcacaggcc tgggcataac gacaatgggt ga         42

<210> SEQ ID NO 301
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 301
cctagcatct ctctggtgtt tggaccttca gataatcttg aa         42

<210> SEQ ID NO 302
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 302
catagcggaa ctttaacaag tgcaaagccc gagcactctg ga         42

<210> SEQ ID NO 303
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 303
cgaccgccat ctatctcagg tgaagtagcc gaacacagct ca         42

<210> SEQ ID NO 304
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 304
ctgtgatgga ctacggaaca tggatatgac gacccaagat ca         42

<210> SEQ ID NO 305
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 305
tttttttttt tgttgtttgt tggcaaagca agtttttttt tt         42

<210> SEQ ID NO 306
<211> LENGTH: 42
<212> TYPE: DNA
<213> ORGANISM: Artificial Sequence
<220> FEATURE:

<223> OTHER INFORMATION: synthetic oligonucleotide

<400> SEQUENCE: 306
ctctgacggc tacattgagg tgcggtgtat tgatcgttag ga                42

<210> SEQ ID NO 307
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 307
cggaagtgcc tccatgattg tgccgtccca agaggtcttg ca                42

<210> SEQ ID NO 308
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 308
ctaccatggc tgctcacgag tgtcctaatt ggaatttcca aa                42

<210> SEQ ID NO 309
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 309
cttagtcggc tgccgatagt tgatggccaa agatctaaat ta                42

<210> SEQ ID NO 310
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 310
cgcaagcgcc tgtatcaggt tgataaccag ggatttggat aa                42

<210> SEQ ID NO 311
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 311
ctggtgacgc ttctaattcg tgaggacaat agaaggatag ga                42

<210> SEQ ID NO 312
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 312
caggagaacc tcttcaacaa tgtattgcaa agaggaccct ta                42

```
<210> SEQ ID NO 313
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 313
ccctctacac ttcggtgcta tgacgctgta ggagttccgg ta                              42

<210> SEQ ID NO 314
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 314
cggacttaac tcgagctccg tgaggtgatc cgatttgcca ta                              42

<210> SEQ ID NO 315
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 315
cctggcgatc tcacaaagcg tgagatgcta ggaggcctgt ga                              42

<210> SEQ ID NO 316
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 316
cgtgagtcgc taaagggcgc tgttccgcta tgaaacacca ga                              42

<210> SEQ ID NO 317
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 317
ccctccctac tgtatgccac tgatggcggt cgacttgtta aa                              42

<210> SEQ ID NO 318
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 318
ctagaattgc tgcctctcat tgtccatcac agacctgaga ta                              42

<210> SEQ ID NO 319
<211> LENGTH: 42
<212> TYPE: DNA
<213> ORGANISM: Artificial Sequence
<220> FEATURE:
<223> OTHER INFORMATION: synthetic oligonucleotide
```

<400> SEQUENCE: 319
cggctgggac tttttttttt tttttttttt ttatgttccg ta                42

<210> SEQ ID NO 320
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 320
catgcctgcc cttgctaact tgccgtcaga gaacaaacaa ca                42

<210> SEQ ID NO 321
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 321
caagactata ctcaggacgc tggcacttcc gacctcaatg ta                42

<210> SEQ ID NO 322
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 322
cacgcgcatc ctccgtttat tgccatggta gacaatcatg ga                42

<210> SEQ ID NO 323
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 323
cgtaaagctg ctatggtcta tgccgactaa gactcgtgag ca                42

<210> SEQ ID NO 324
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 324
cgtgaatgca ctcggtagac tggcgcttgc gaactatcgg ca                42

<210> SEQ ID NO 325
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 325
ctcggtaata ctttatgcta tgcgtcacca gaacctgata ca                42

<210> SEQ ID NO 326
<211> LENGTH: 42

```
<212> TYPE: DNA
<213> ORGANISM: Artificial Sequence
<220> FEATURE:
<223> OTHER INFORMATION: synthetic oligonucleotide

<400> SEQUENCE: 326
caagagtctc ctttagacag tggttctcct gacgaattag aa                              42

<210> SEQ ID NO 327
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 327
ccggctggcc ctgggctgcg tgtgtagagg gattgttgaa ga                              42

<210> SEQ ID NO 328
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 328
cctatggaca ctacgcacgt tgttaagtcc gatagcaccg aa                              42

<210> SEQ ID NO 329
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 329
cagagatgaa cttgactcgt tgatcgccag gacggagctc ga                              42

<210> SEQ ID NO 330
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 330
caccctagcg ctgggcactt tgcgactcac gacgctttgt ga                              42

<210> SEQ ID NO 331
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 331
cctgcccgta ctatacatag tgtagggagg gagcgcccctt ta                             42

<210> SEQ ID NO 332
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 332
```
cgaagagacc cttgatttgg tgcaattcta gagtggcata ca                              42

<210> SEQ ID NO 333
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 333
cctttgccgg cttctatact tgtcccagcc gaatgagagg ca                              42

<210> SEQ ID NO 334
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 334
tttttttttt tcagtatgta tgggcaggca tgttttttttt tt                             42

<210> SEQ ID NO 335
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 335
ctgtatcggc tttagtataa tgtatagtct tgaagttagc aa                              42

<210> SEQ ID NO 336
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 336
catctgggtc tacaagaccc tggatgcgcg tgagcgtcct ga                              42

<210> SEQ ID NO 337
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 337
cacagatgtc tatttgcgag tgcagcttta cgaataaacg ga                              42

<210> SEQ ID NO 338
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 338
cagcgtggac tcgtaacaat tgtgcattca cgatagacca ta                              42

<210> SEQ ID NO 339
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 339
ccggctcgcc tctgggtagc tgtattaccg agagtctacc ga        42

<210> SEQ ID NO 340
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 340
cgcctagctc tagcaaactg tggagactct tgatagcata aa        42

<210> SEQ ID NO 341
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 341
cccggctatc tagtgcgacg tgggccagcc ggactgtcta aa        42

<210> SEQ ID NO 342
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 342
ccagaatgac tcgacctcgg tgtgtccata ggacgcagcc ca        42

<210> SEQ ID NO 343
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 343
caaagacgac tctattccgt tgttcatctc tgaacgtgcg ta        42

<210> SEQ ID NO 344
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 344
ctgggccaac tacgggcctc tgcgctaggg tgaacgagtc aa        42

<210> SEQ ID NO 345
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 345
cgtgtgtgac tgttcggacc tgtacgggca ggaaagtgcc ca        42

<210> SEQ ID NO 346
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 346
caccgtttcc taagtagtca tgggtctctt cgactatgta ta					42

<210> SEQ ID NO 347
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 347
cccaggcttc tgtaagagta tgccggcaaa ggaccaaatc aa					42

<210> SEQ ID NO 348
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 348
cttggaagac tttttttttt tttttttttt ttaagtatag aa					42

<210> SEQ ID NO 349
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 349
gccgatacag atacatactg a					21

<210> SEQ ID NO 350
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 350
gacccagatg attatactaa a					21

<210> SEQ ID NO 351
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 351
gacatctgtg agggtcttgt a					21

<210> SEQ ID NO 352
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 352
gtccacgctg actcgcaaat a                                              21

<210> SEQ ID NO 353
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 353
ggcgagccgg aattgttacg a                                              21

<210> SEQ ID NO 354
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 354
gagctaggcg agctacccag a                                              21

<210> SEQ ID NO 355
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 355
gatagccggg acagtttgct a                                              21

<210> SEQ ID NO 356
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 356
gtcattctgg acgtcgcact a                                              21

<210> SEQ ID NO 357
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 357
gtcgtctttg accgaggtcg a                                              21

<210> SEQ ID NO 358
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 358
gttggcccag aacggaatag a                                              21

<210> SEQ ID NO 359

```
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 359
gtcacacacg agaggcccgt a                                              21

<210> SEQ ID NO 360
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 360
ggaaacggtg aggtccgaac a                                              21

<210> SEQ ID NO 361
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 361
gaagcctggg atgactactt a                                              21

<210> SEQ ID NO 362
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 362
gtcttccaag atactcttac a                                              21

<210> SEQ ID NO 363
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 363
ggaagggatg gagga                                                     15

<210> SEQ ID NO 364
<211> LENGTH: 15
<212> TYPE: DNA
<213> ORGANISM: Artificial Sequence
<220> FEATURE:
<223> OTHER INFORMATION: synthetic oligonucleotide
<220> FEATURE:
<221> NAME/KEY: Biotin
<222> LOCATION: (15)..(15)
<223> OTHER INFORMATION: C modified with biotin

<400> SEQUENCE: 364
tcctccatcc cttcc                                                     15
```

COMPOSITIONS AND METHODS RELATING TO NUCLEIC ACID NANO- AND MICRO-TECHNOLOGY

RELATED APPLICATIONS

This application is a national stage filing under 35 U.S.C. §371 of International Application No. PCT/US2012/049306 filed Aug. 2, 2012, which was published under PCT Article 21(2) in English, and which claims the benefit of U.S. Provisional Application Ser. No. 61/515,435, filed on Aug. 5, 2011, and U.S. Provisional Application Ser. No. 61/612,018, filed on Mar. 16, 2012, all entitled "COMPOSITIONS AND METHODS RELATING TO NUCLEIC ACID NANO- AND MICRO-TECHNOLOGY", the entire contents of each of which are incorporated by reference herein.

FEDERALLY SPONSORED RESEARCH

This invention was made with Government support under Contract No. N00014-10-1-0827 awarded by U.S. Department of Defense, Office of Naval Research. The Government has certain rights in the invention.

BACKGROUND OF INVENTION

Previous work relating to synthesis of nucleic acid nanostructures (or microstructures) involved a "DNA origami" approach in which a naturally occurring "scaffold" DNA several kilobases in length is folded into a structure through the use of a plurality of helper strands that each hybridize to two, three or more non-contiguous regions of the scaffold DNA. Such folding approaches are limited, in part, by the ability to obtain scaffolds other than that currently in use (i.e., M13mp18 viral genome DNA, about 7 kilobases in length). They are also limited in their versatility since each nucleic acid structure requires a specific design and set of helper strands in order to generate the necessary folding of the scaffold DNA.

Still earlier work involved the use of nucleic acid "tile" monomers, each made up of 5 single stranded oligonucleotides, having a relatively rigid core structure and flanking sequences that hybridized to other monomers in order to form nucleic acid structures. The most complex structure produced using these tile monomers was a 4 by 4 square structure.

More recent work involved the use of subsets of identical single stranded oligonucleotides to form DNA tubes of particular circumferences. This work was limited by its ability to form only a few types of structures, namely ribbons and tubes. Moreover, the end user could not exert much control over the size of such structures based on the nature of the single stranded oligonucleotides used to generate the structures.

SUMMARY OF INVENTION

The invention provides novel methods for making nucleic acid structures of known and predetermined and thus controlled size, shape and complexity, as well as the nucleic acid structures themselves. The nucleic acid structures of the invention are made by binding a plurality of single stranded oligonucleotides to each other in a sequence-specific manner. The nucleic acid structures and the single stranded oligonucleotides are designed so that the location of each oligonucleotide in each structure is known, and accordingly so that the nucleotide sequence at each location in the structure is known. The ability to know the location of each oligonucleotide and therefore the nucleotide sequence at each position in the structure facilitates modification of the structure in a defined and controlled manner. The invention also provides pluralities of the nucleic acid structures that are substantially monodisperse with respect to size, shape and/or complexity. Members of the plurality of nucleic acid structures may also be identical to each other with respect to oligonucleotide positioning within each structure, allowing for a plurality of nucleic acid structures to be modified in an identical manner. The plurality of structures thus may be characterized as monodisperse with respect to modification also. As described herein, the versatility of this approach is demonstrated, at least in part, by the ability to generate, using a "one-pot" annealing reaction, at least 107 distinctly shaped nucleic acid structures using subsets from a 310 oligonucleotide pool.

Certain nucleic structures of the invention are comprised of parallel double helices with crossovers or half crossovers, or some combination thereof. Typically, a plurality of single stranded oligonucleotides anneals to form a double helix in the structure.

Each oligonucleotide in a nucleic acid structure may be unique (i.e., it may be present only once per structure) or it may be present once, twice, three times, or even more frequently. The invention contemplates nucleic acid structures having one or more unique oligonucleotides. In some instances, at least one oligonucleotide contributing to a double helix is unique. In some instances, at least one double helix in the structure comprises an oligonucleotide that is unique from all other oligonucleotides in that helix or in the structure as a whole.

The invention also provides the single stranded oligonucleotides used to generate the nucleic acid structures. Different pluralities of single stranded oligonucleotides are provided, with the nature and composition of those pluralities depending on the design, including shape, size and complexity, of the desired structure. As explained in greater detail herein, these pluralities typically comprise 2-domain and 4-domain oligonucleotides.

The invention contemplates that the single stranded oligonucleotides and the nucleic acid structures are modular in nature. The methods of the invention allow for variously shaped nucleic acid structures to be made by inclusion and/or exclusion of a subset of known oligonucleotides. The methods also contemplate modular assembly of nucleic acid structures to each other, for example by annealing such structures to each other based on sequence specificity. In some of these embodiments, the nucleic acid structures that are annealed to each other may share a common shape (e.g., both may be tubes, or both may be lattices). The methods also contemplate composite nucleic acid structures made by linking two or more nucleic acid structures to each other using linkers that may or may not be integral to the nucleic acid structure. In these embodiments, nucleic acid structures that are linked to each other may be of the same or of different shape.

The invention further contemplates synthesis of nucleic acid structures by combining a plurality of known single stranded oligonucleotides in a single vessel and allowing the oligonucleotides to self-assemble, in a predetermined manner, under suitable conditions. Similarly, two or more nucleic acid structures may be combined in a single vessel and allowed to self-assemble based on nucleotide sequence complementarity in a predetermined manner, under suitable conditions, thereby forming a larger nucleic acid structure.

Thus, in one aspect, the invention provides a nucleic acid structure comprising a plurality of annealed oligonucleotides, each oligonucleotide comprising at least two domains, arranged into at least two parallel double helices, wherein at least one double helix comprises a unique domain.

In some embodiments, at least one double helix comprises 2 or more unique domains. In some embodiments, at least 50% of the double helices comprise one or more unique domains. In some embodiments, the structure comprises at least 5, at least 10, or at least 20 parallel double helices.

In another aspect, the invention provides a nucleic acid structure comprising a plurality of annealed oligonucleotides, each oligonucleotide comprising at least two domains, arranged into at least two parallel double helices, wherein at least one double helix is unique.

In some embodiments, the structure comprises 2 or more unique double helices. In some embodiments, at least 50% of the double helices are unique. In some embodiments, at least 50% of the double helices comprise one or more unique domains. In some embodiments, the structure comprises at least 5, at least 10, or at least 20 parallel double helices.

In another aspect, the invention provides a nucleic acid structure comprising a plurality of annealed oligonucleotides, each oligonucleotide comprising at least two domains, arranged into at least two parallel double helices, wherein at least one oligonucleotide in the structure is unique.

In some embodiments, at least 50% of the oligonucleotides in the structure are unique. In some embodiments, all of the oligonucleotides in the structure are unique. In some embodiments, the structure comprises at least 5, at least 10, or at least 20 parallel double helices.

In another aspect, the invention provides a composition comprising a plurality of nucleic acid structures of any of the foregoing claims, wherein the plurality is at least 50% homogeneous.

In another aspect, the invention provides a method comprising annealing a plurality of single stranded oligonucleotides in a single vessel to form a nucleic acid structure, wherein the single stranded oligonucleotides each comprise at least two domains, and wherein at least one single stranded oligonucleotide is present at a molar concentration that is 10-fold lower than the molar concentration of other oligonucleotides in the plurality.

In another aspect, the invention provides a method comprising annealing a plurality of single stranded oligonucleotides in a single vessel to form a nucleic acid structure, wherein the single stranded oligonucleotides each comprise at least two domains, and wherein at least one single stranded oligonucleotide is present at a molar concentration that is 100-fold lower than the molar concentration of other oligonucleotides in the plurality.

In some embodiments, annealing occurs through a temperature transition over a period of time. In some embodiments, the temperature transition is a change in temperature from an elevated temperature to about room temperature. In some embodiments, the temperature transition is a change in temperature from about 90° C. to about room temperature. In some embodiments, the annealing occurs over a period of about 12-24 hours.

In another aspect, the invention provides a nucleic acid structure prepared by any of the foregoing methods.

In another aspect, the invention provides a composite nucleic acid structure comprising at least two nucleic acid structures of any of the foregoing claims, conjugated to each other through a spacer-linker.

In some embodiments, the spacer-linker comprises nucleic acid elements and non-nucleic acid elements. In some embodiments, the spacer-linker comprises a carbon chain. In some embodiments, the spacer-linker is a homobifunctional spacer-linker.

In some embodiments of any of the foregoing aspects, a first subset of oligonucleotides comprises 2 domains and a second subset of oligonucleotides comprises 4 domains. In some embodiments, the oligonucleotides are 21-104 nucleotides in length. In some embodiments, the single stranded oligonucleotides are DNA oligonucleotides. In some embodiments, the single stranded oligonucleotides are L-DNA oligonucleotides. In some embodiments, the single stranded oligonucleotides are RNA oligonucleotides. In some embodiments, the single stranded oligonucleotides comprise modifications such as but not limited to backbone modifications, sugar modifications, base modifications. The single stranded oligonucleotides may be homogeneous or heterogeneous respecting such and other modifications.

In one aspect, the invention provides a nucleic acid structure comprising a plurality of unique oligonucleotides, wherein all the oligonucleotides are less than 1 kb in length. In some embodiments, the oligonucleotides are less than 100 bases in length. In some embodiments, some oligonucleotides in the structure are n oligonucleotides in length (where n represents an integer that is a multiple of 10.5) and some oligonucleotides are n/2 in length. In some embodiments, some oligonucleotides are about 42 nucleotides in length (e.g., the 4-domain oligonucleotides) and some oligonucleotides are about 21 nucleotides in length (e.g., the 2-domain oligonucleotides).

The invention contemplates nucleic acid structures having a variety of arrangements of oligonucleotides. In some embodiments, the nucleic acid structures comprise oligonucleotides that comprise, as an example, 5 domains, wherein 2 such domains are bound to one domain on a distinct and separate oligonucleotide in the structure. In some embodiments, the 2 domains that bind to a single domain in another oligonucleotide may not be contiguous to each other or linked to each other when bound to the other single domain. In some embodiments, the structures comprise half crossovers. In some embodiments, the structures contain crossovers. In some embodiments, the structures contain half crossovers and crossovers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

It is to be understood that the Figures are not necessarily to scale, emphasis instead being placed upon generally illustrating the various concepts discussed herein.

DETAILED DESCRIPTION OF INVENTION

The invention relates, in its broadest sense, to methods of making nucleic acid structures of predetermined, and thus controlled, shape, size and complexity. The invention is premised, in part, on the unexpected finding that select pluralities of single stranded oligonucleotides can be self-assembled to form nucleic acid structures of controlled shape, size, complexity and modification. It was considered surprising, inter alia, that stable nucleic acid structures of various predetermined shapes and controlled sizes could be formed using only a plurality of single stranded oligonucleotides.

The nucleic acid structures of the invention comprise a plurality of oligonucleotides arranged (via sequence-specific annealing) in a predetermined or known manner. As a result, the position of each oligonucleotide in the structure is known. In this way, the structure may be modified, for example through attachment of moieties, at particular positions. This may be accomplished by using a modified oligonucleotide as a starting material or by modifying a particular oligonucleotide after the structure is formed. Therefore, knowing the position of each of the starting oligonucleotides in the resultant structure provides addressability to the structure.

The nucleic acid structures of the invention may be made, in some instances, through a process of self-assembly of single stranded oligonucleotides. In these self-assembly methods, the single stranded oligonucleotides are combined in a single vessel and allowed to anneal to each other, based on sequence complementarity. In some instances, this annealing process involves placing the oligonucleotides at an elevated temperature and then reducing the temperature gradually in order to favor sequence-specific binding. As used herein, the term "self-assembly" refers to the ability of oligonucleotides (and in some instances nucleic acid structures) to anneal to each other, in a sequence-specific manner, in a predicted manner and without external control (e.g., by sequential addition of oligonucleotides or nucleic acid structures).

The invention therefore provides, inter alia, compositions comprising the single stranded oligonucleotides of the invention, methods of making nucleic acid structures of various predetermined or known size, shape, complexity and modification, nucleic acid structures of various predetermined or known size, shape, complexity and modification, pluralities of nucleic acid structures wherein such pluralities may be substantially monodisperse with respect to size, shape, complexity and modification, composition structures comprising two or more nucleic acid structures, and methods of making such composite structures. The invention also provides methods of using the nucleic acid structures and the composite structures of the invention. These aspects and embodiments of the invention will be described in greater detail herein.

Figure 1:
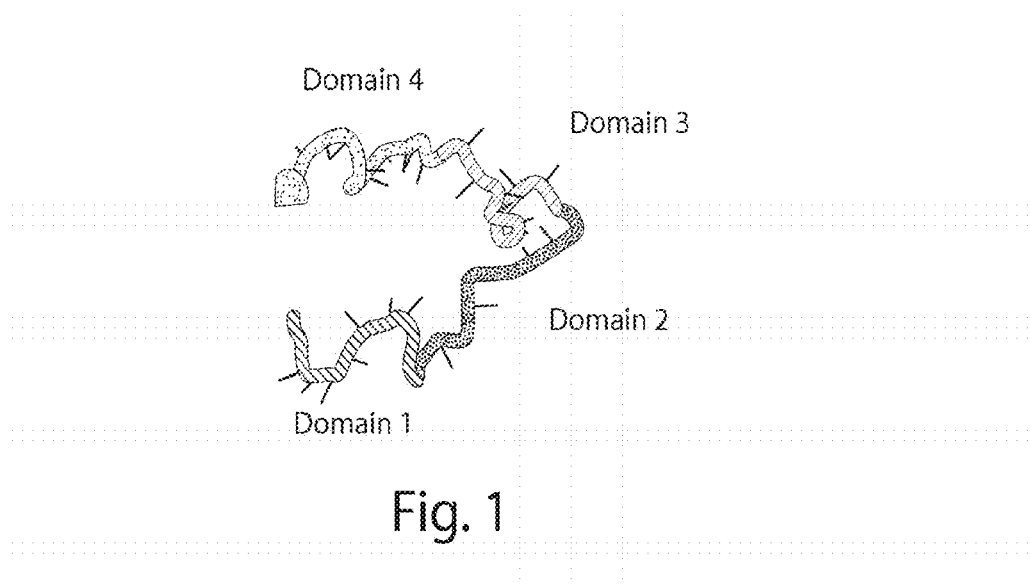
FIG. 1 is a schematic of a single stranded oligonucleotide comprising 4 domains (referred to herein as a 4-domain single stranded oligonucleotide). Each domain is of a different nucleotide sequence (as may be represented by a different color). Each domain is characterized by its sequence and its length, as discussed herein. The arrow head represents the 3' end of the oligonucleotide and the other end of the oligonucleotide is the 5' end. Certain oligonucleotides of the invention comprise only 2 domains (and these are referred to herein as 2-domain oligonucleotides). Each oligonucleotide is defined by its number of domains, by the order to such domains, and its overall nucleotide sequence.

Nucleic Acid Structures:

The nucleic acid structures of the invention are comprised of a plurality of oligonucleotides that are bound to each other in a sequence-specific manner. The oligonucleotides of the invention typically comprise two or more domains. FIG. 1 provides a schematic of a 4-domain oligonucleotide. Prior to the annealing process that forms the nucleic acid structure, the oligonucleotides are in a single stranded form.

Figure 2A:
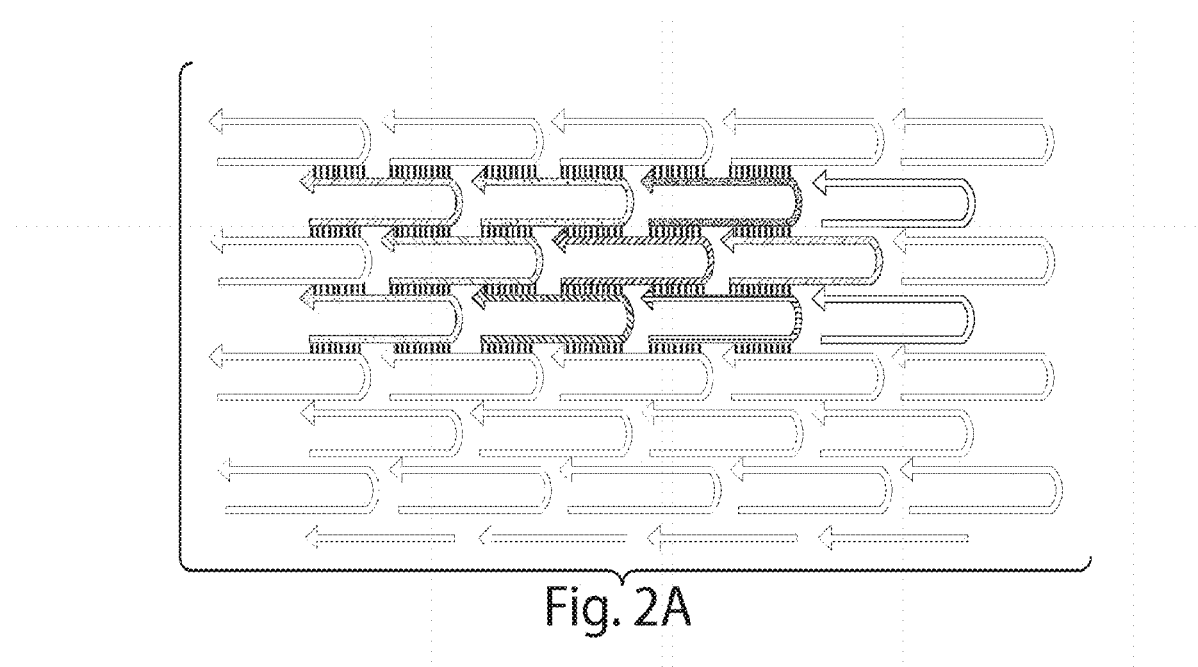
FIG. 2A is a schematic of a region of a nucleic acid structure showing 4-domain single stranded oligonucleotides (represented in this Figure by "U" shaped structures) and 2-domain single stranded oligonucleotides (represented by linear structures at the bottom, also referred to herein as boundary oligonucleotides). Illustrated are the inter-domain, inter-oligonucleotide bonds, and half crossovers between helices. The half crossovers are also illustrated, and as noted in the Figure these are comprised of phosphate backbone moieties. The half-crossovers typically do not comprise a nucleotide and thus do not contribute to sequence-specific binding and do not dictate the location or position of an oligonucleotide in the structure. For illustration purposes, nine of the 4-domain oligonucleotides are shown bonded to each other and/or other oligonucleotides. In this illustration, all nine have a unique sequence relative to each other (as may be represented by different colors).
Figure 2B:
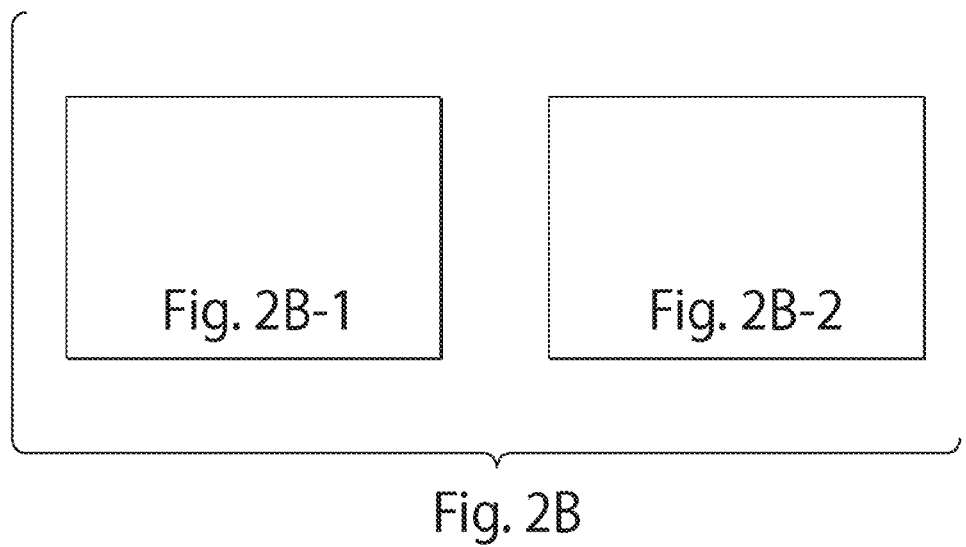
FIG. 2B is a schematic of regions of two nucleic acid structures showing the arrangement of 2- and 4-domain single stranded oligonucleotides. In the top schematic, each 4-domain oligonucleotide is configured in a "U" shape and provides only a single half crossover between the two double helices it contributes to. In the bottom schematic, one of the 4-domain oligonucleotides contributes two half crossovers between the double helices it contributes to. The structure therefore contains a crossover and multiple half crossovers. The same oligonucleotide may be characterized as having a domain order of 5' d2-a-b-c-d1 3', wherein domains d1 and d2 bind to domain d* in forming the double helix. The domains are labeled with different identifiers to indicate unique sequences relative to each other.
Figures 1, 2B:
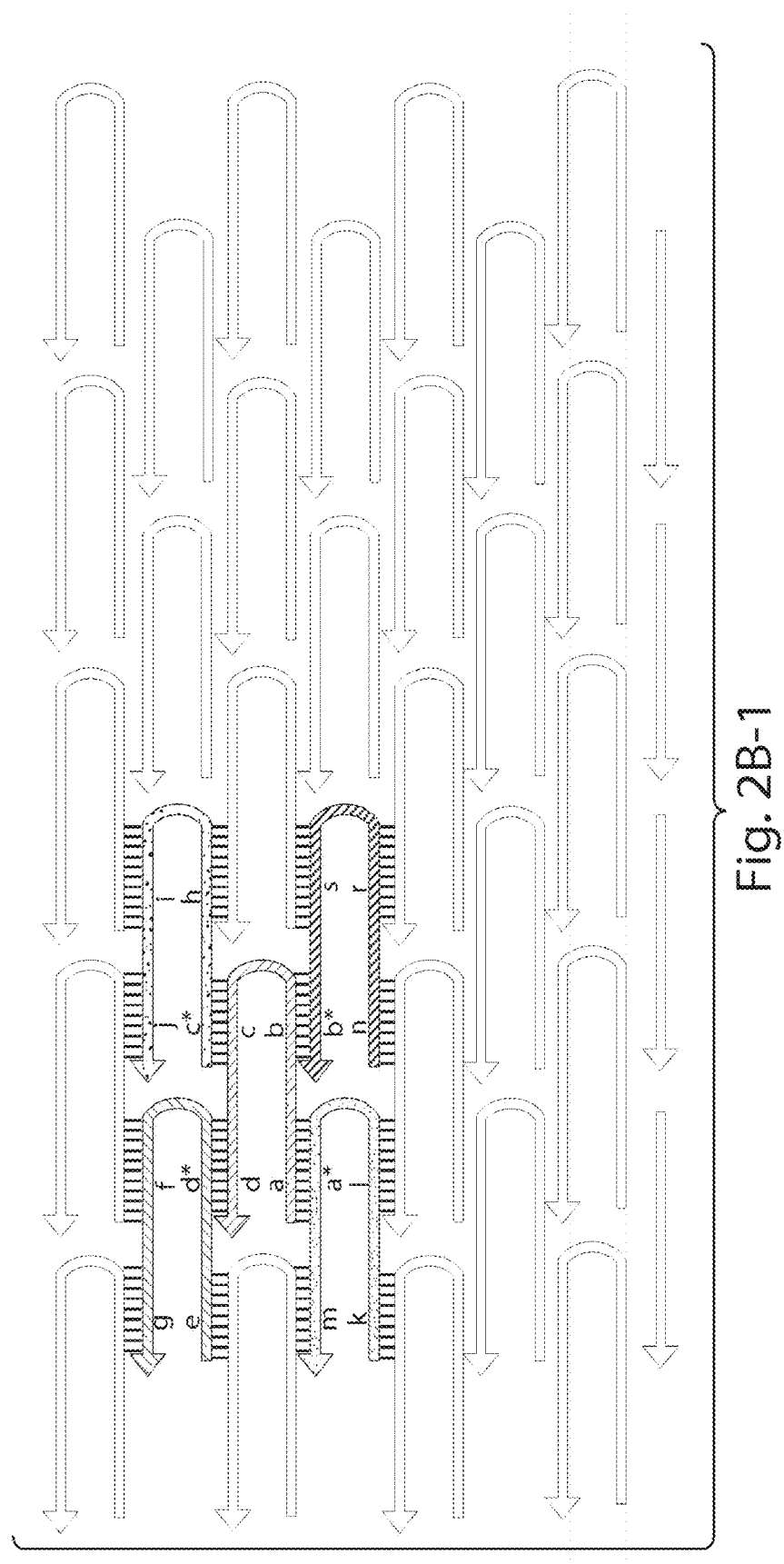
Figures 2, 2B:
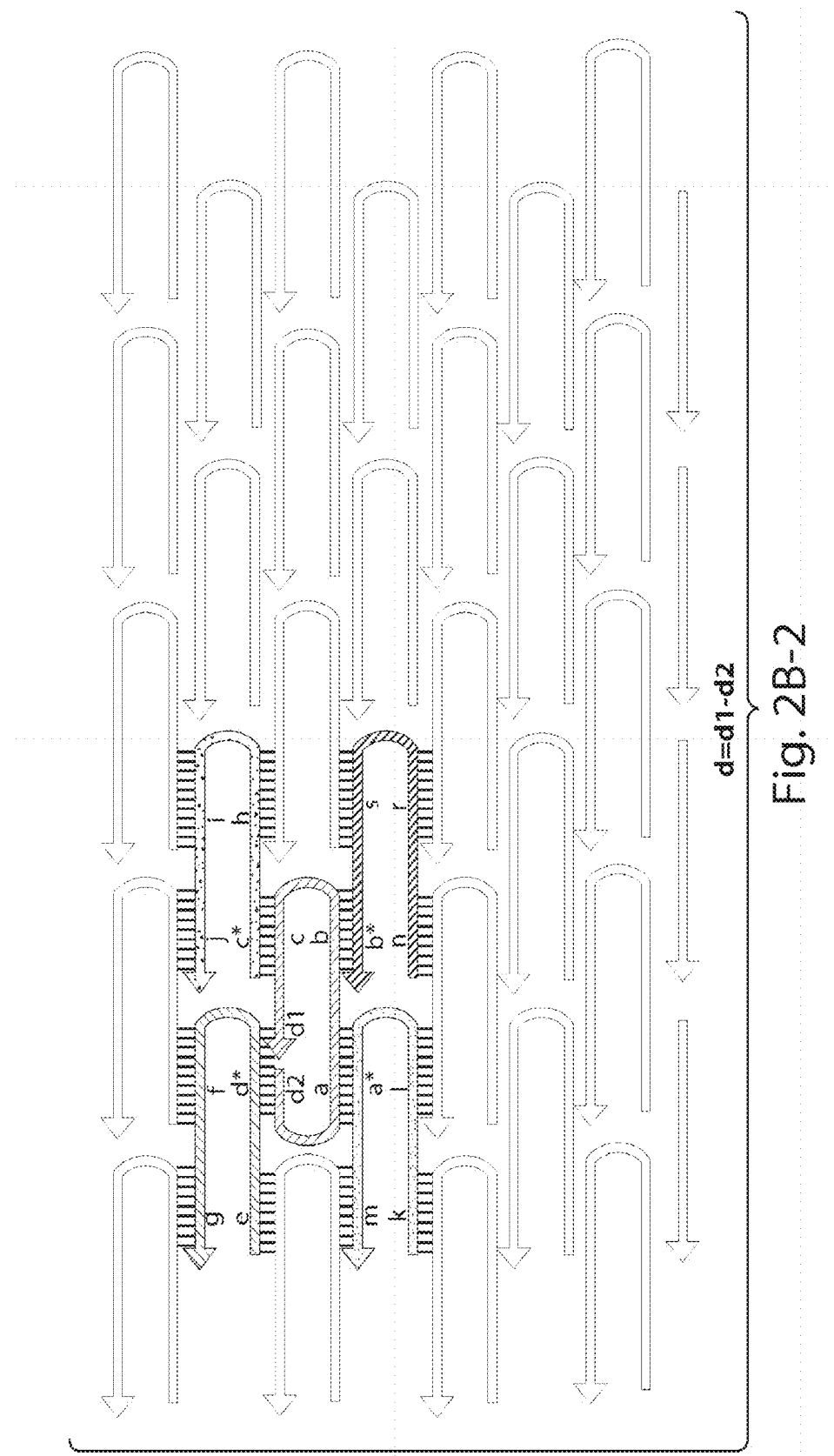
Figure 2C:
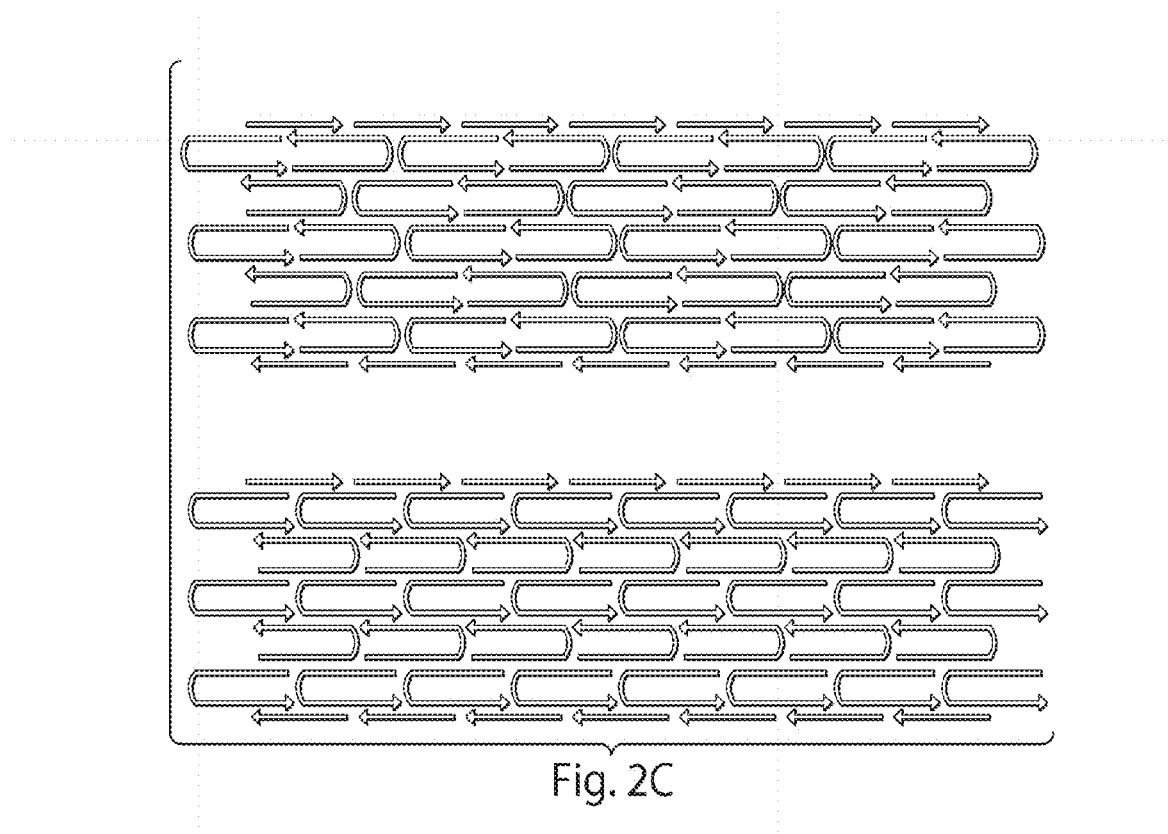
FIG. 2C is a schematic showing still other contemplated arrangements of 4-domain oligonucleotides in a nucleic acid structure. The top structure comprises a plurality of crossovers. The bottom structure comprises a plurality of half crossovers. The distance between the crossovers in the top structure is greater than the distance between the half crossovers in the bottom structure. As an example, the distance in the top structure may be 4 domains, while the distance in the bottom structure may be 2 domains. Nucleic acid structures comprising the top arrangement have been made experimentally.

Generally, every domain of an oligonucleotide binds to another domain in another oligonucleotide in the structure. FIG. 2A provides a schematic of the arrangement and binding interactions between 2- and 4-domain oligonucleotides in a region of a structure. The 2-domain oligonucleotides are shown at the bottom by straight arrows, and the 4-domain oligonucleotides are shown as U-shaped arrows. The 4-domain oligonucleotides, when present in a nucleic acid structure of the invention, have an area of about 3 nm by 7 nm. They may be referred to herein as single-stranded tiles (SST). In the context of a nucleic acid structure, each SST may be viewed as a "molecular pixel". The arrow head in each of the Figures represents the 3' end of the oligonucleotide. A similar representation is provided in FIG. 2B (top). FIG. 2B (bottom) shows an alternative embodiment in which an oligonucleotide is comprised of 5 domains, and two of those domains together bind to another domain on a physically separate oligonucleotide. When bound to the other domain, these two domains denoted d1 and d2 are not directly conjugated to each other and rather there is essentially a nick between them. The structure also then comprises a crossover based on the orientation of the 5'-d2-a-b-c-d1-3' oligonucleotide. Still other arrangements are shown in FIG. 2C. As illustrated, the oligonucleotides may be arranged such that the structure comprises crossovers (as shown in FIG. 2C top), half crossovers (as shown in FIG. 2C bottom), or a combination of these (as shown in FIG. 2B bottom). The oligonucleotides may also be arranged such that crossovers and/or half crossovers occur at different distances including but not limited to every two domains or every four domains, and the like. It should be understood that the invention therefore contemplates various binding arrangements for oligonucleotides within a nucleic acid structure.

In some instances, however, certain domains in a nucleic acid structure may not bind to another domain in the structure. As an example, in some instances, oligonucleotides having a poly T domain are present in the structure, preferably at borders and in configurations that result in the poly T domains being single stranded.

Figures 1, 10A:
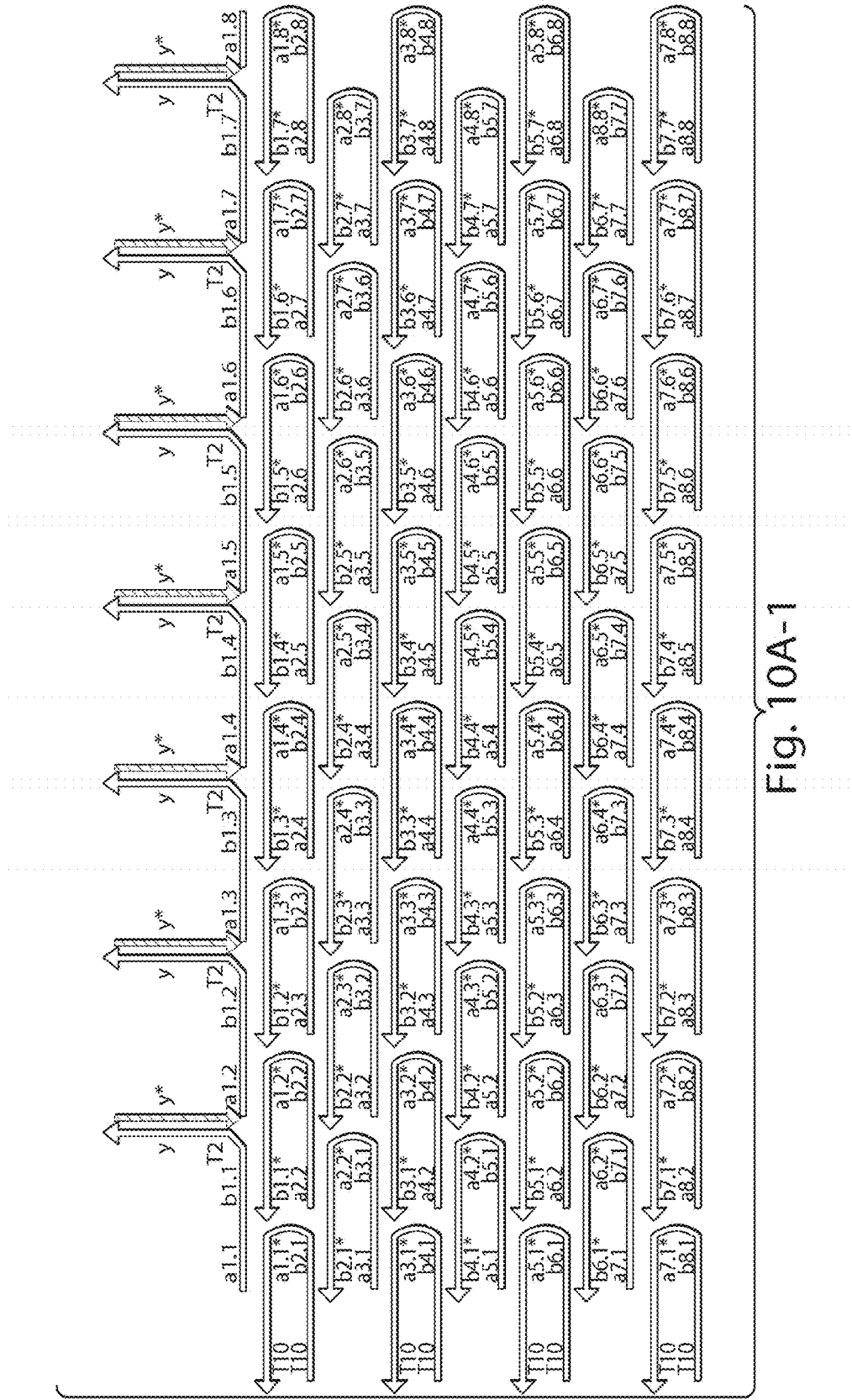
FIGS. 10A and B are a schematic (A) and AFM images (B) showing nucleic acid structure with "handles". The handles are provided as additional domains attached to the 2-domain boundary oligonucleotides, resulting in 3-domain boundary oligonucleotides. In the Figure, a double T (T2) spacer is present between the second and third domains, where the third domain represents the handle domain. An oligonucleotide that is complementary to the third domain may be included in the annealing reaction. In the Figure, this complementary oligonucleotide is denoted y* and has a biotin modification at its 3' end. The biotin moiety can then be used to bind streptavidin. The AFM images show such structures bound to labeled streptavidin. The invention contemplates incorporating such handle domains anywhere in the structure, including at the boundaries, edges and/or internally.
Figures 2, 10A:
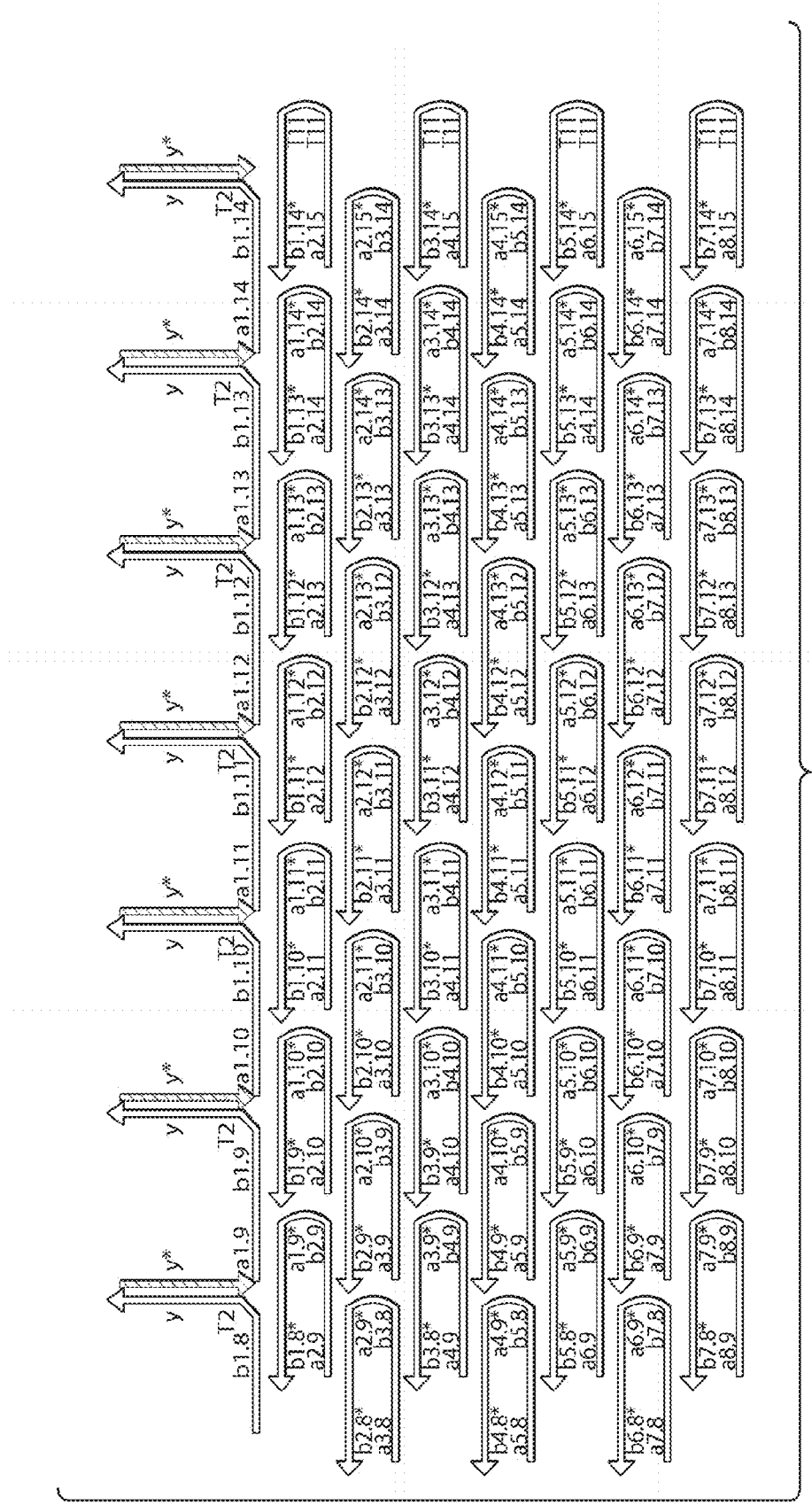
Figures 3, 10A:
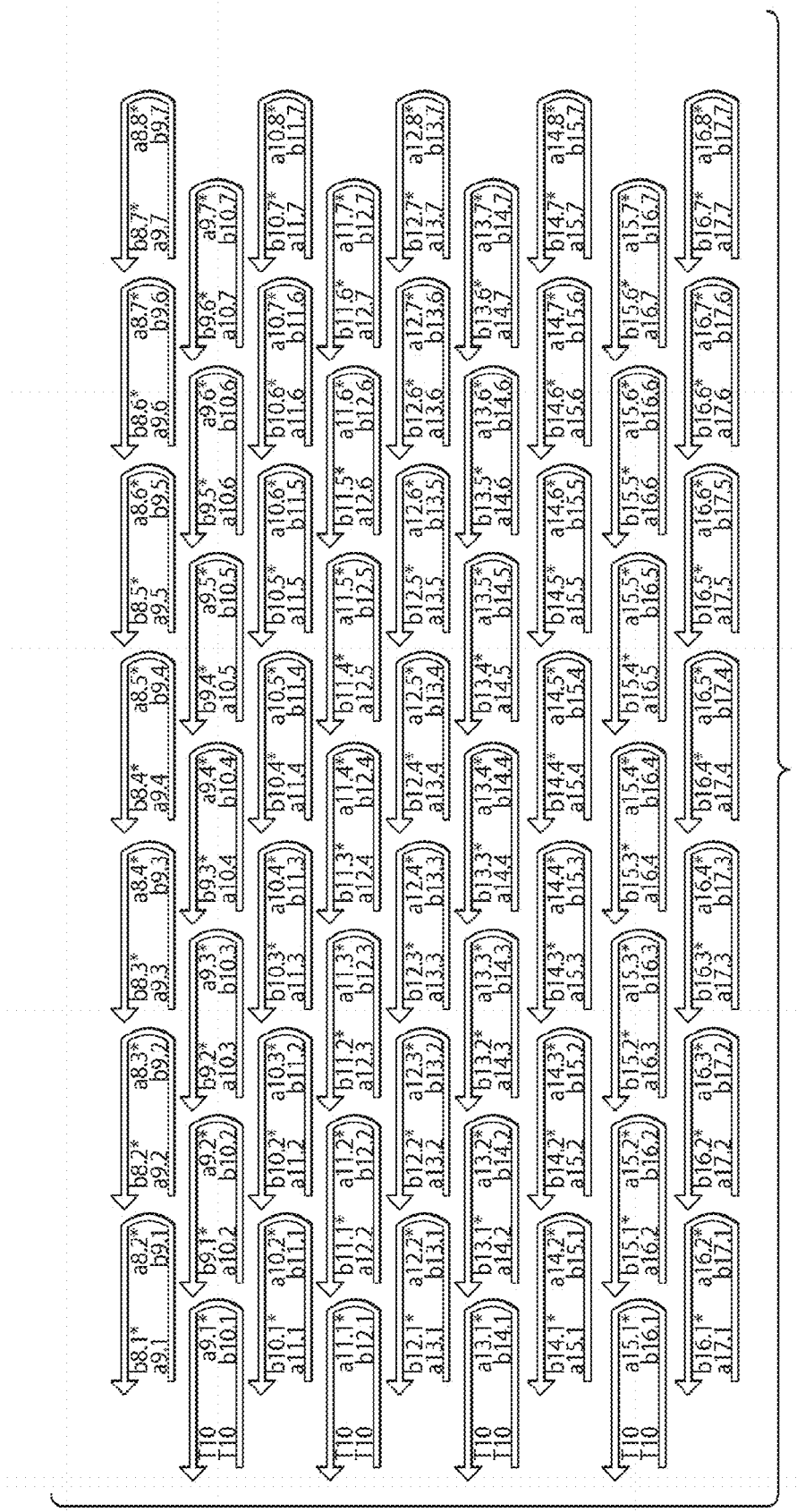
Figures 4, 10A:
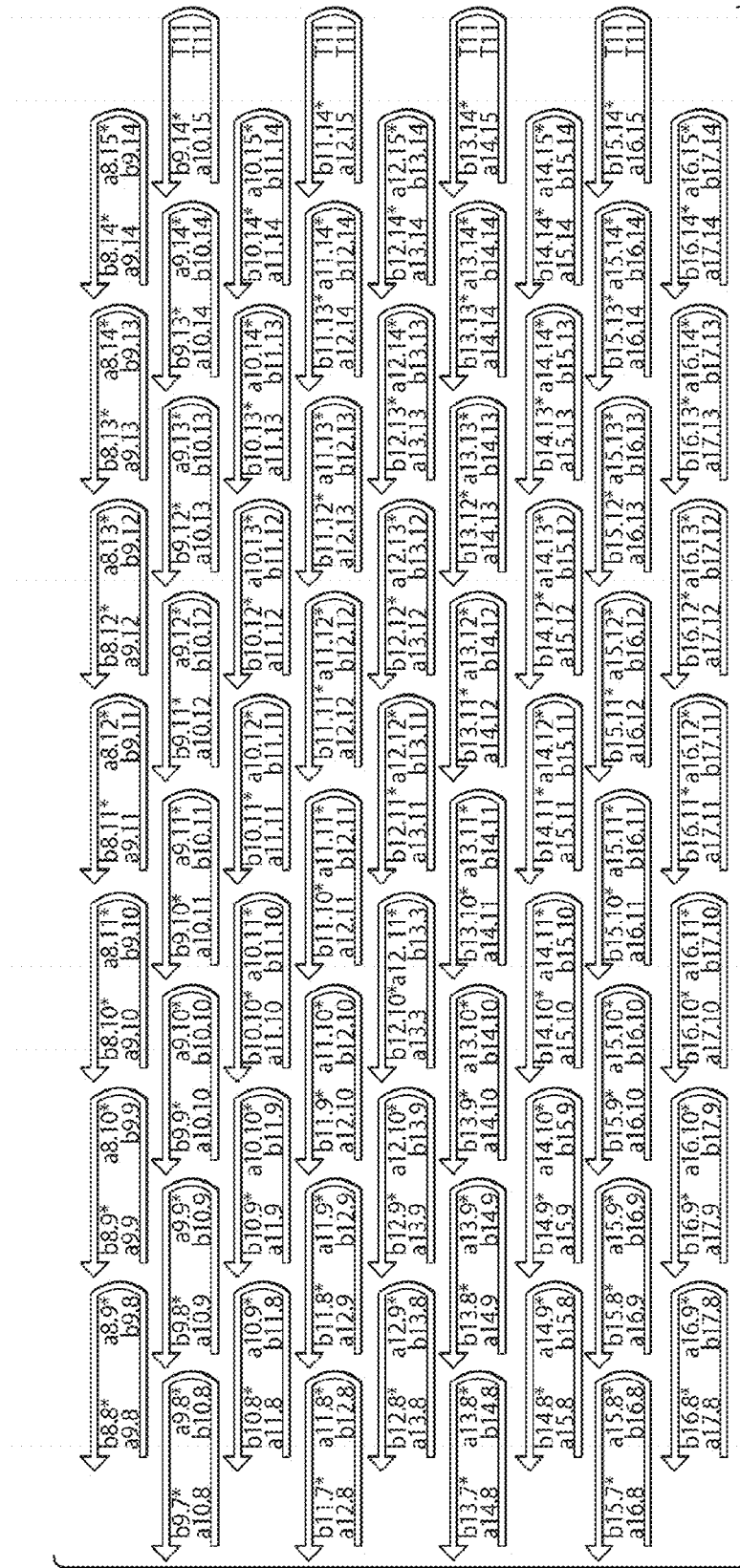
Figures 5, 10A:
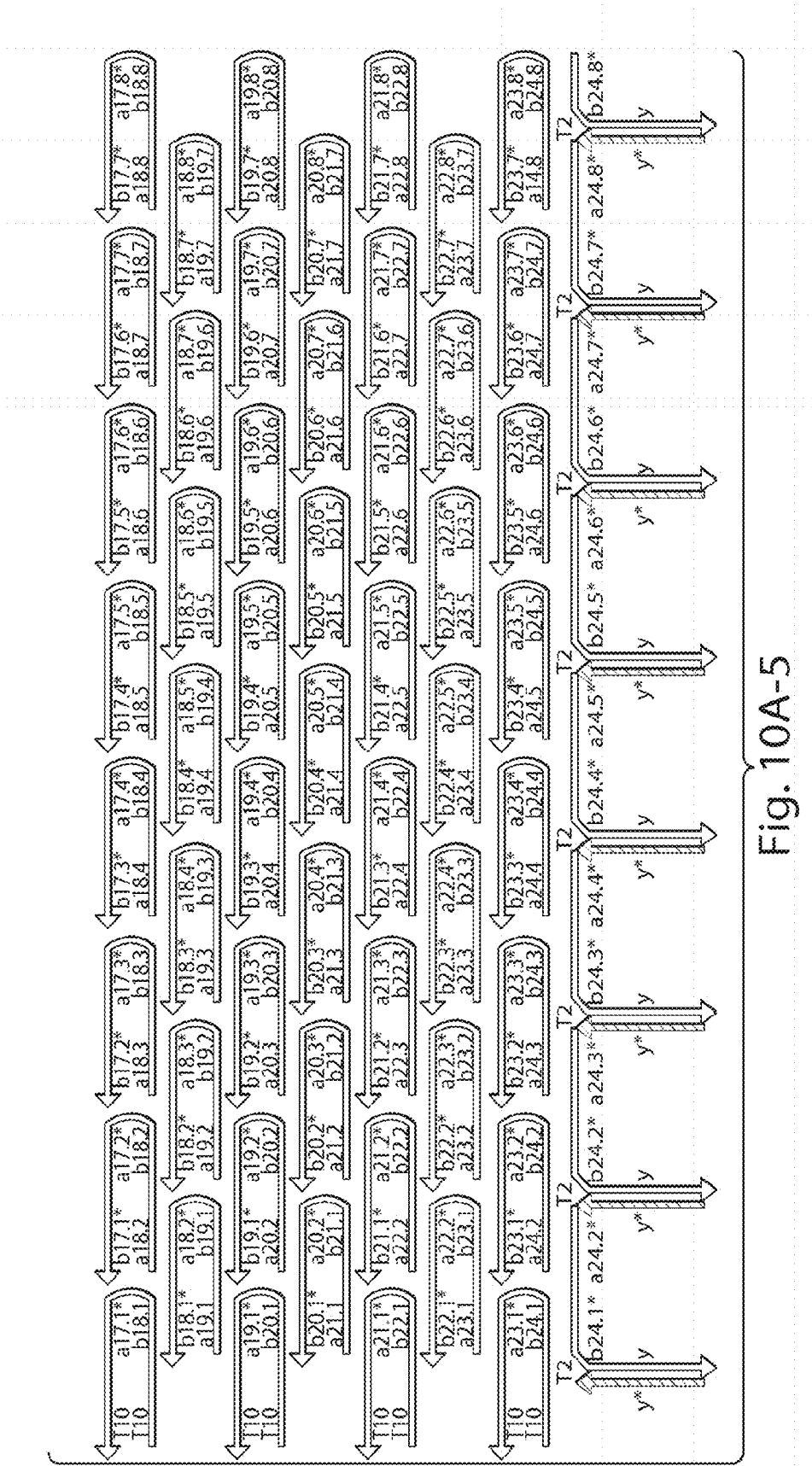
Figures 6, 10A:
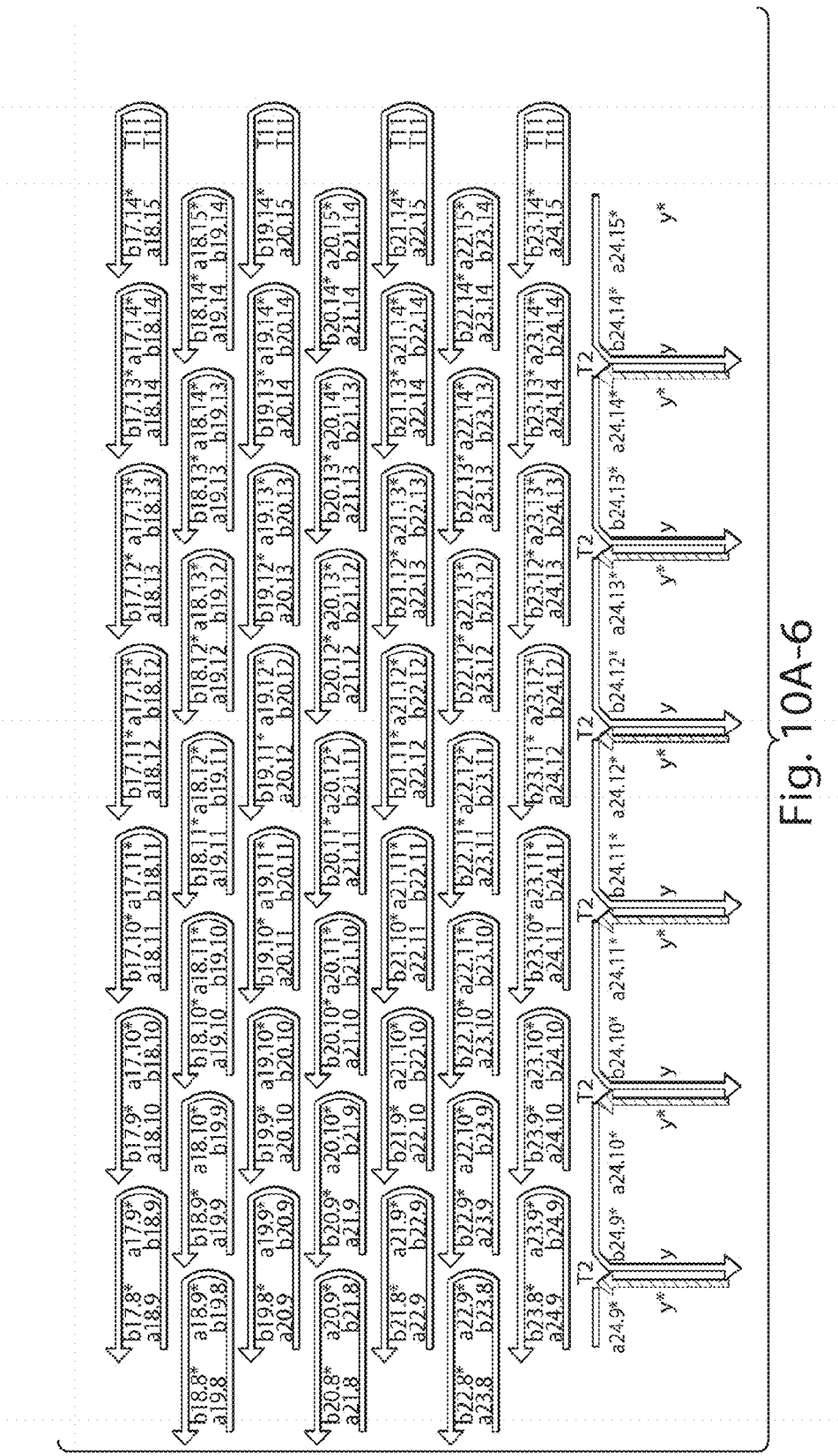
Figure 10B:
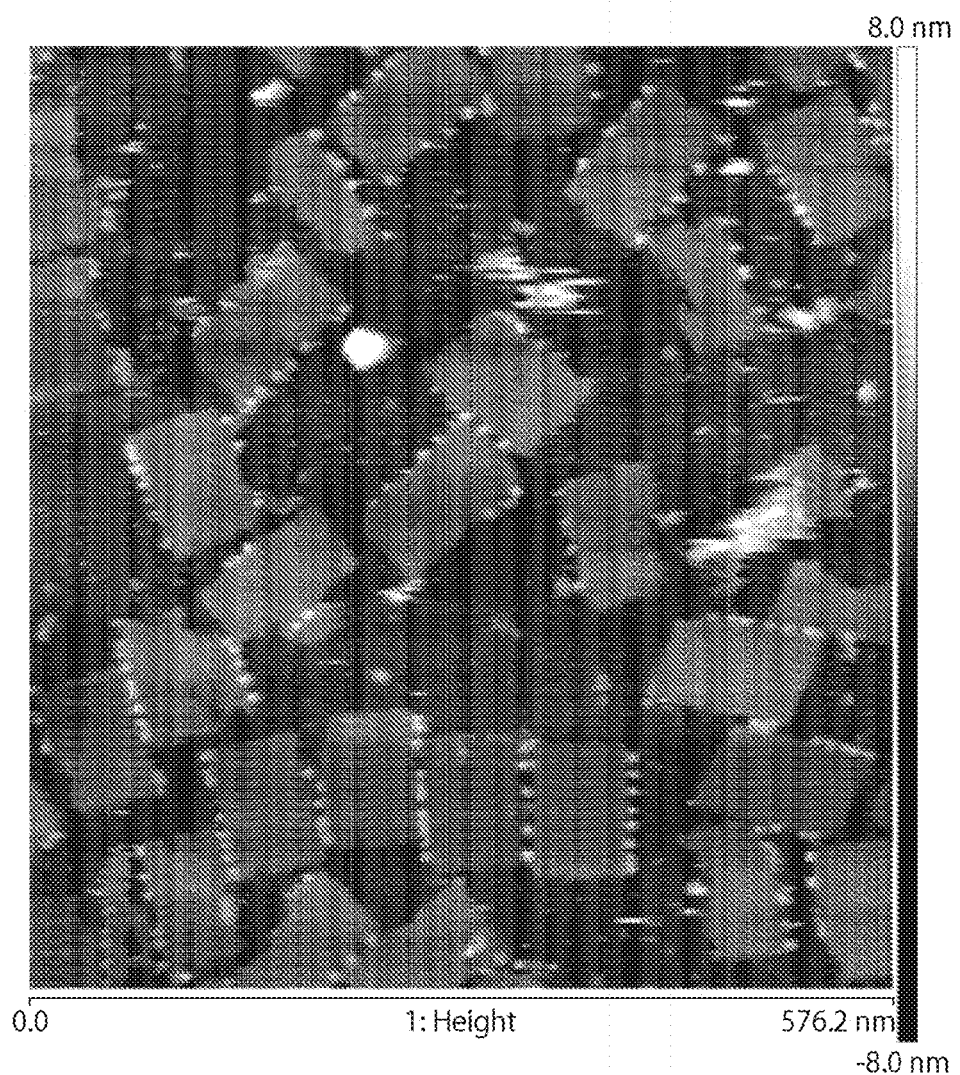
Figures 1, 11:
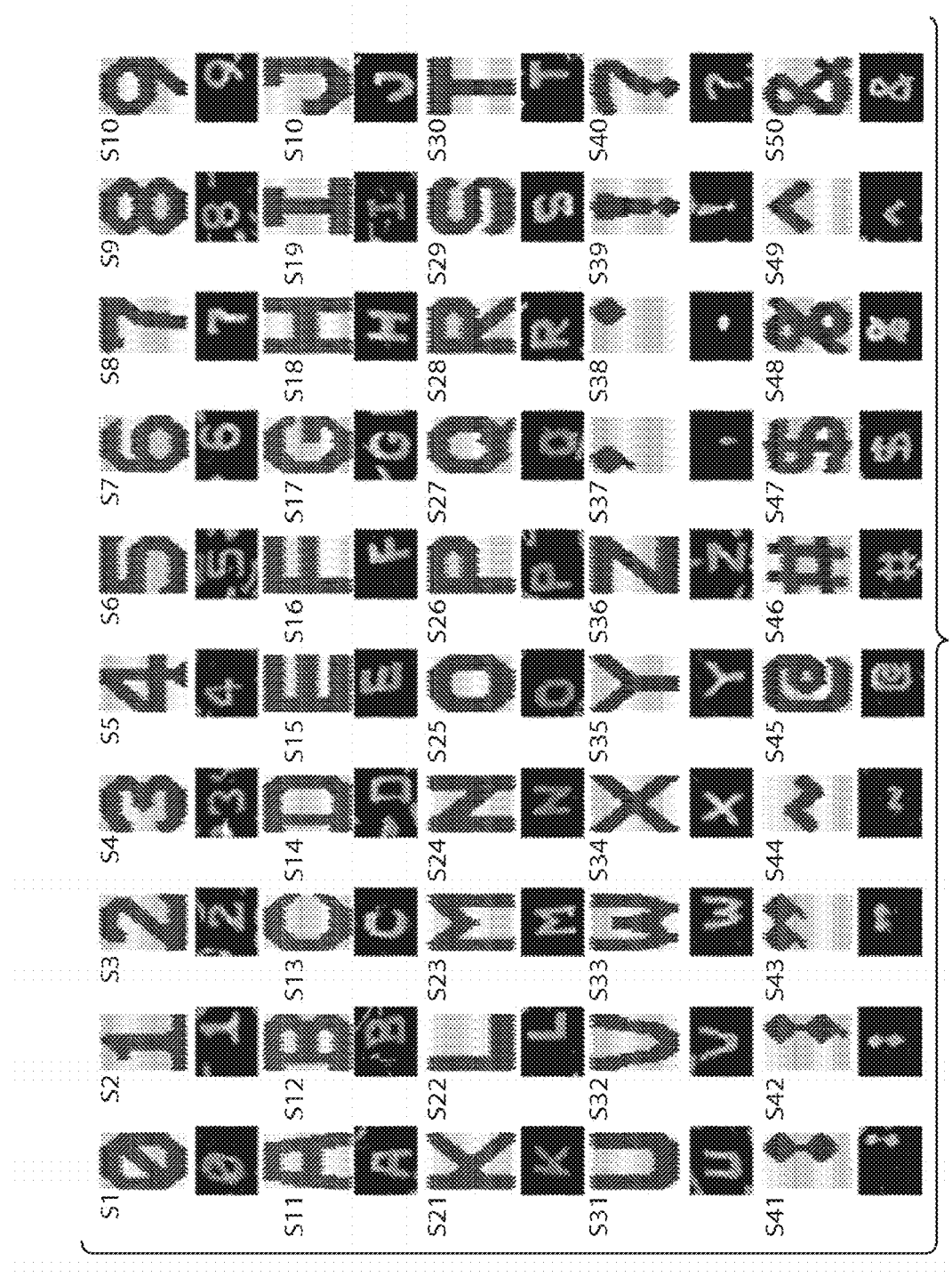
FIG. 11 is a compilation of diagrams (top panels) and corresponding AFM images (bottom panels) for a variety of structures generated in accordance with the invention.
Figures 2, 11:
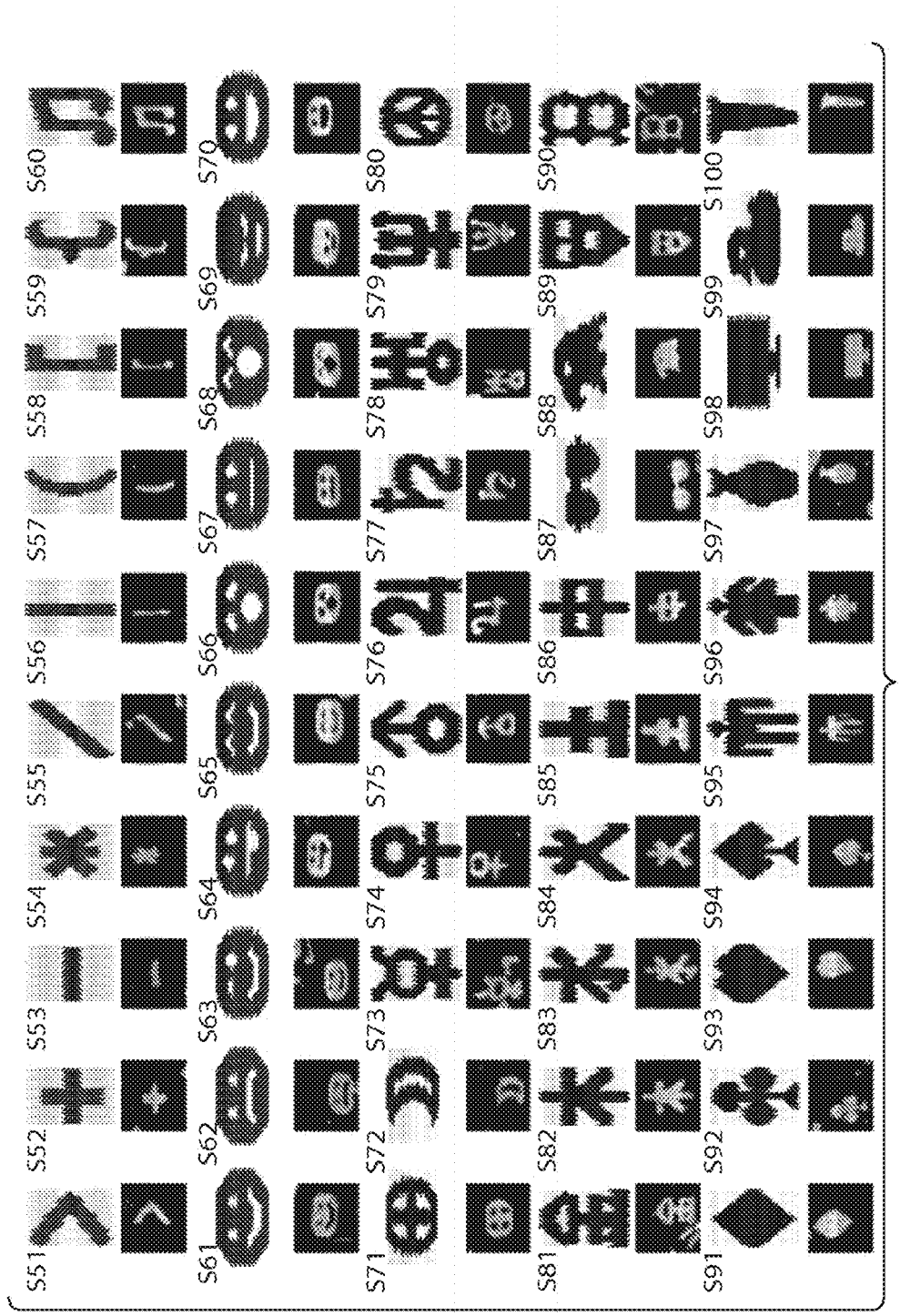

As another example, domains may be used as handles for annealing to other structures or to other moieties. Such handle domains are shown in FIG. 10A at the top and bottom borders of the lattice structure. Oligonucleotides comprising biotin moieties were bound to these handles and the structures were subsequently contacted with streptavidin. The location of the binding of the streptavidin is shown in FIG. 10B.

Figure 3A:
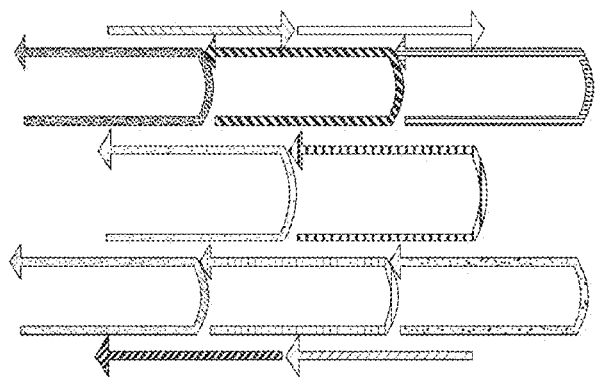
FIG. 3A is a schematic of a four parallel double helix lattice made up of 12 distinct oligonucleotides (A) and an eight parallel double helix square made up of 40 distinct oligonucleotides (B).
Figure 3A:
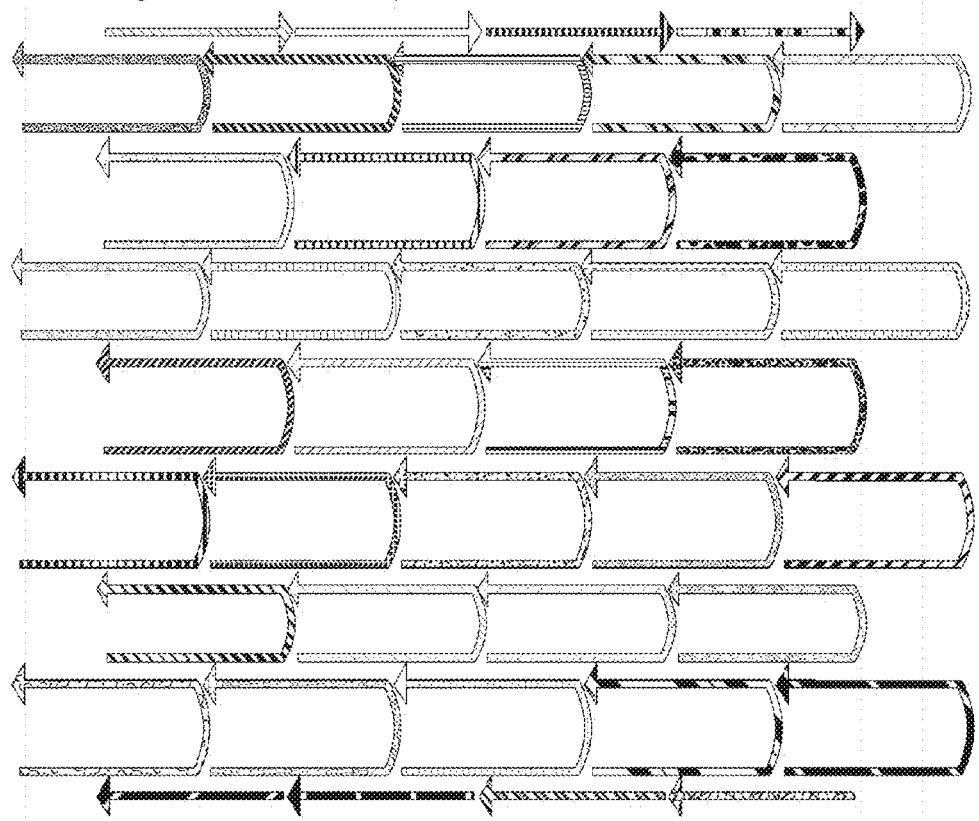
Figure 3B:
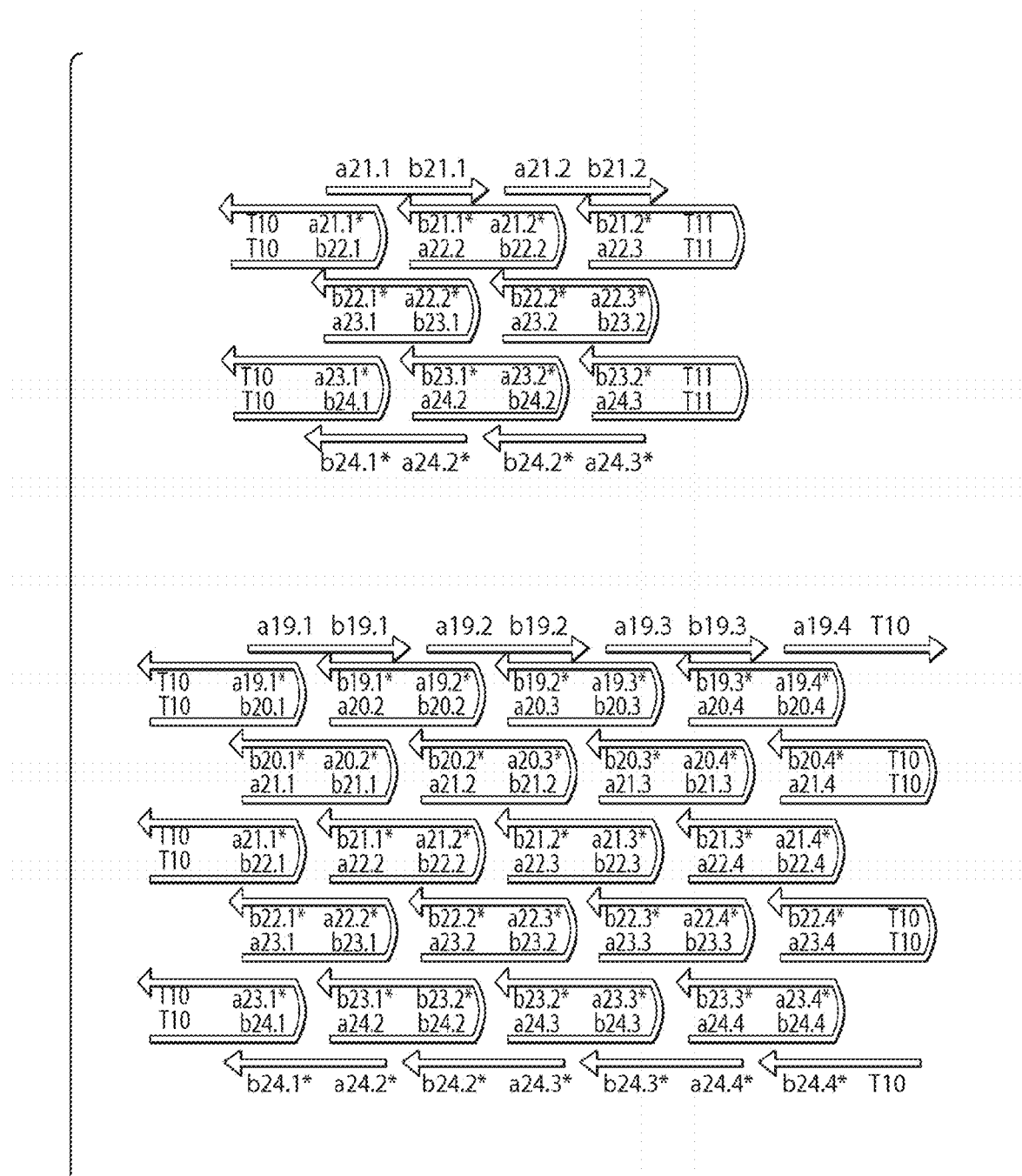
FIG. 3B-F are schematic maps of nucleic acid structures, commonly shaped as lattices but of different sizes. Size may be expressed as the number of double helices and the number of helical turns per double helix. Typically, the number of helical turns is similar or identical between the double helices in a structure. Each of these Figures is made of a plurality of unique oligonucleotides that are identified by their domain content and order. Each domain is identified by a certain alpha-numeric designation, and each oligonucleotide is identified by its domain content and order. The listing of the oligonucleotides, their designations, and their domain and sequence composition are provided in Table 1. The lattice in FIG. 3F is a 24 double helix lattice made up of 362 distinct oligonucleotides with sequences provided in Table 1. The lattices in FIGS. 3B-3D comprise a subset of these oligonucleotides, and may include additional 2-domain oligonucleotides as boundary oligonucleotides.
Figure 3C:
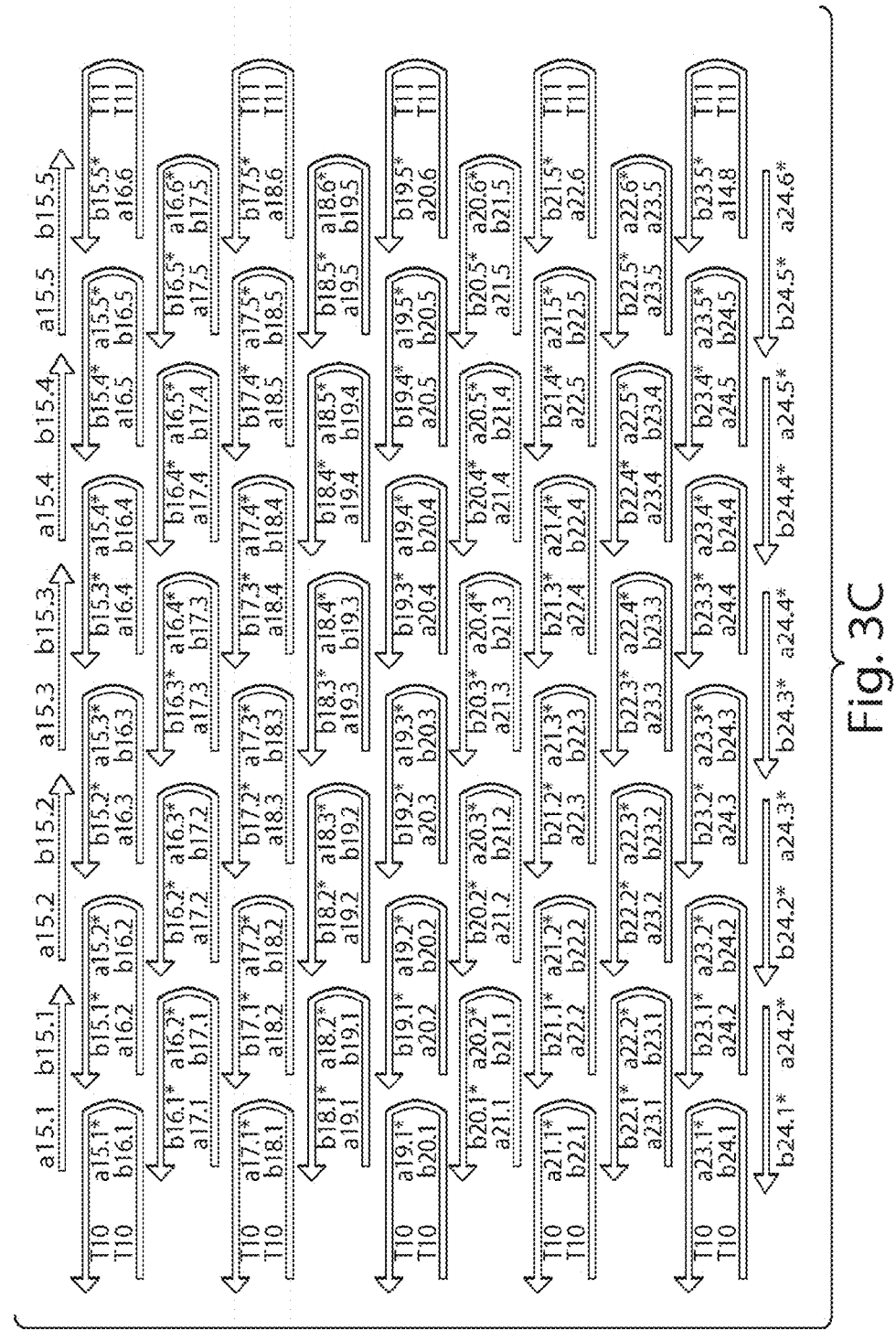
Figure 3D:
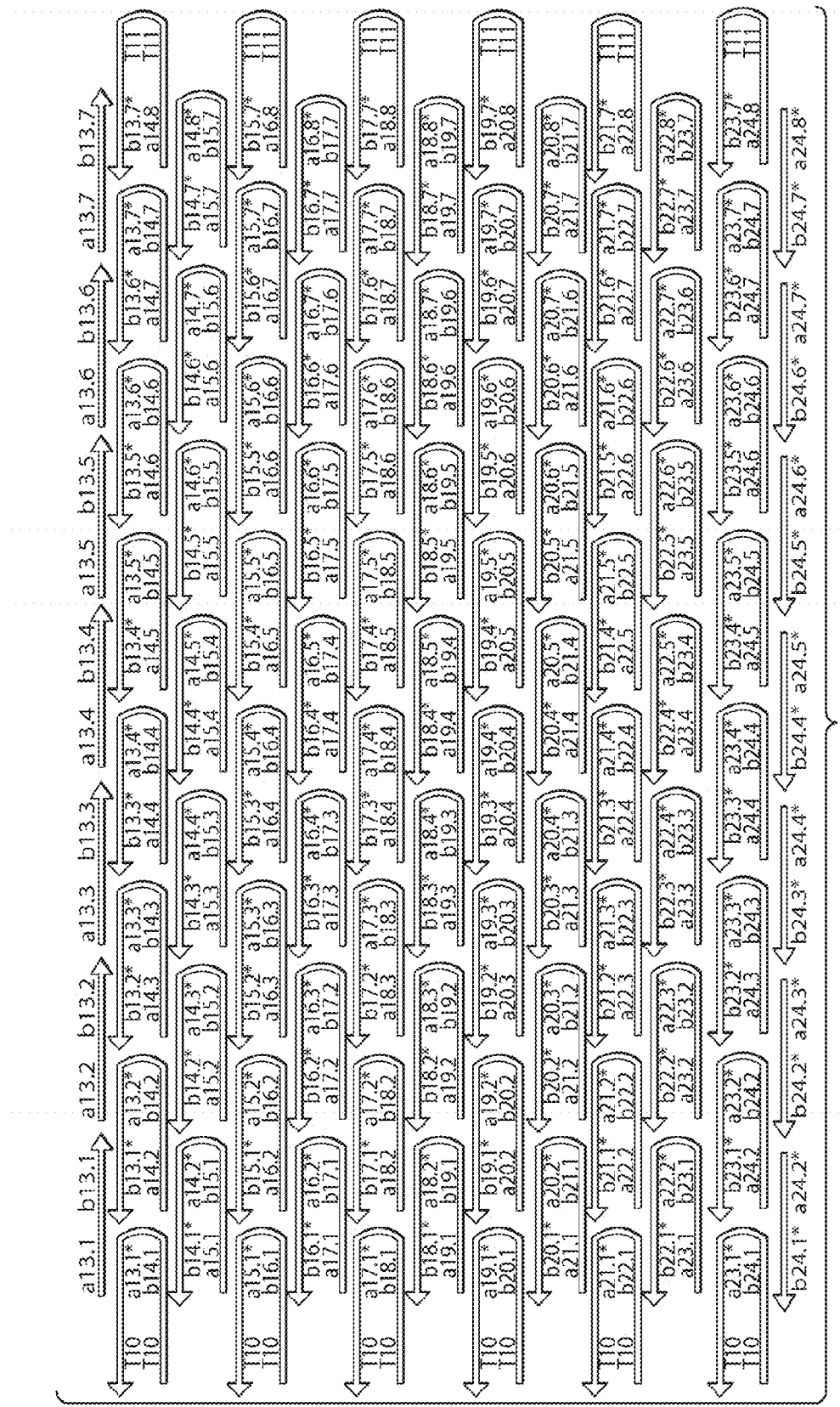
Figures 1, 3E:
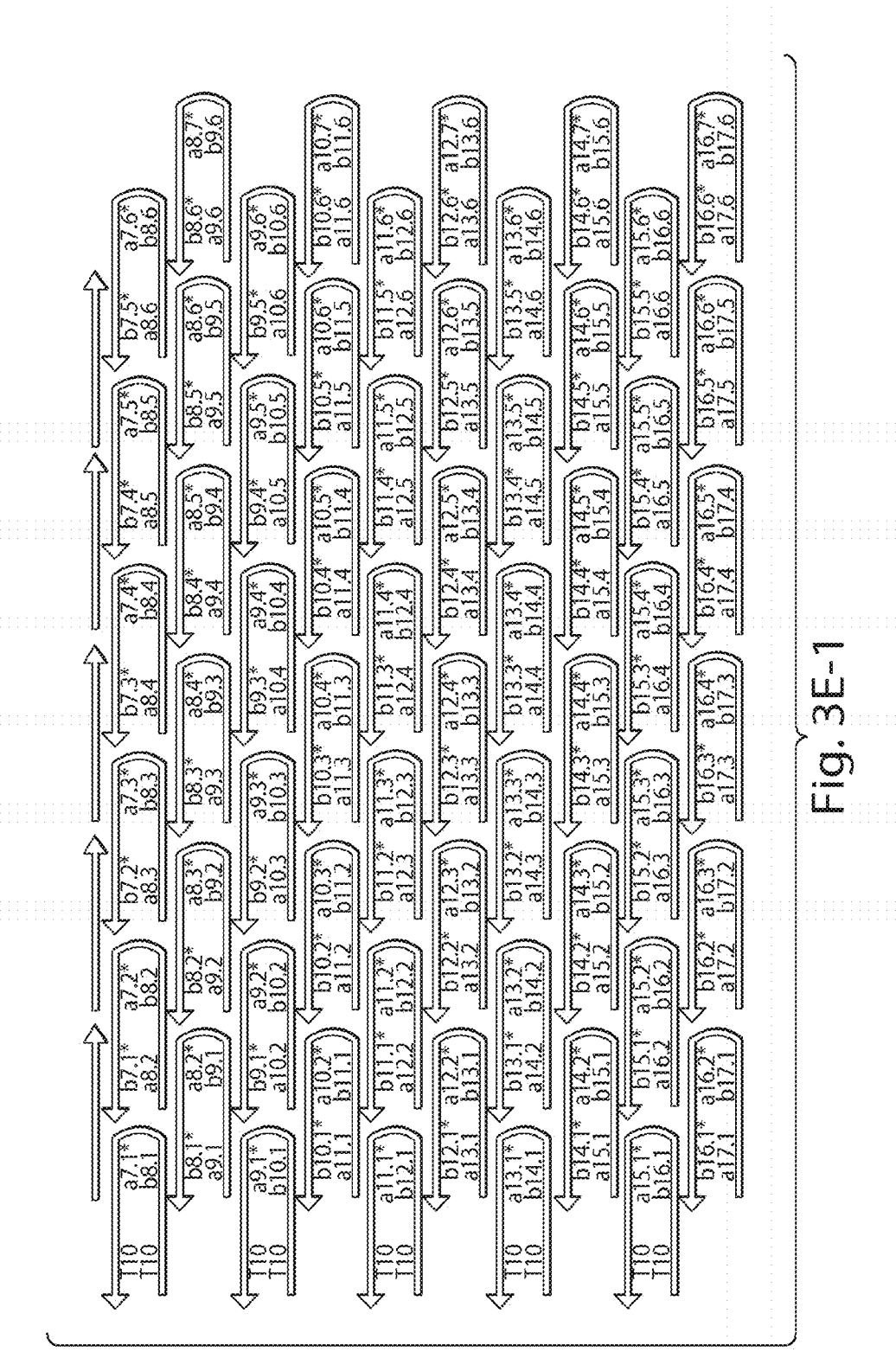
Figures 2, 3E:
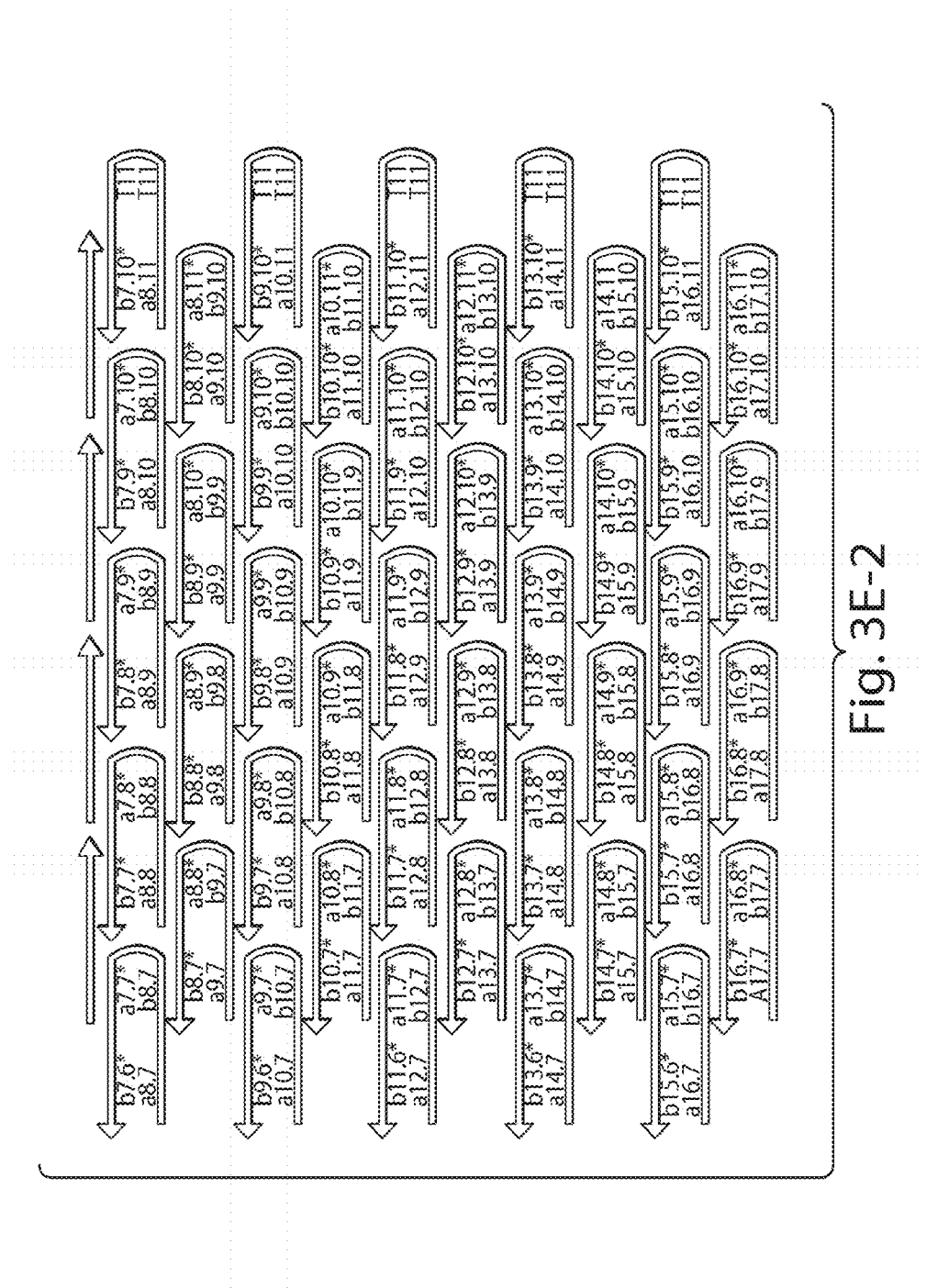
Figures 3, 3E:
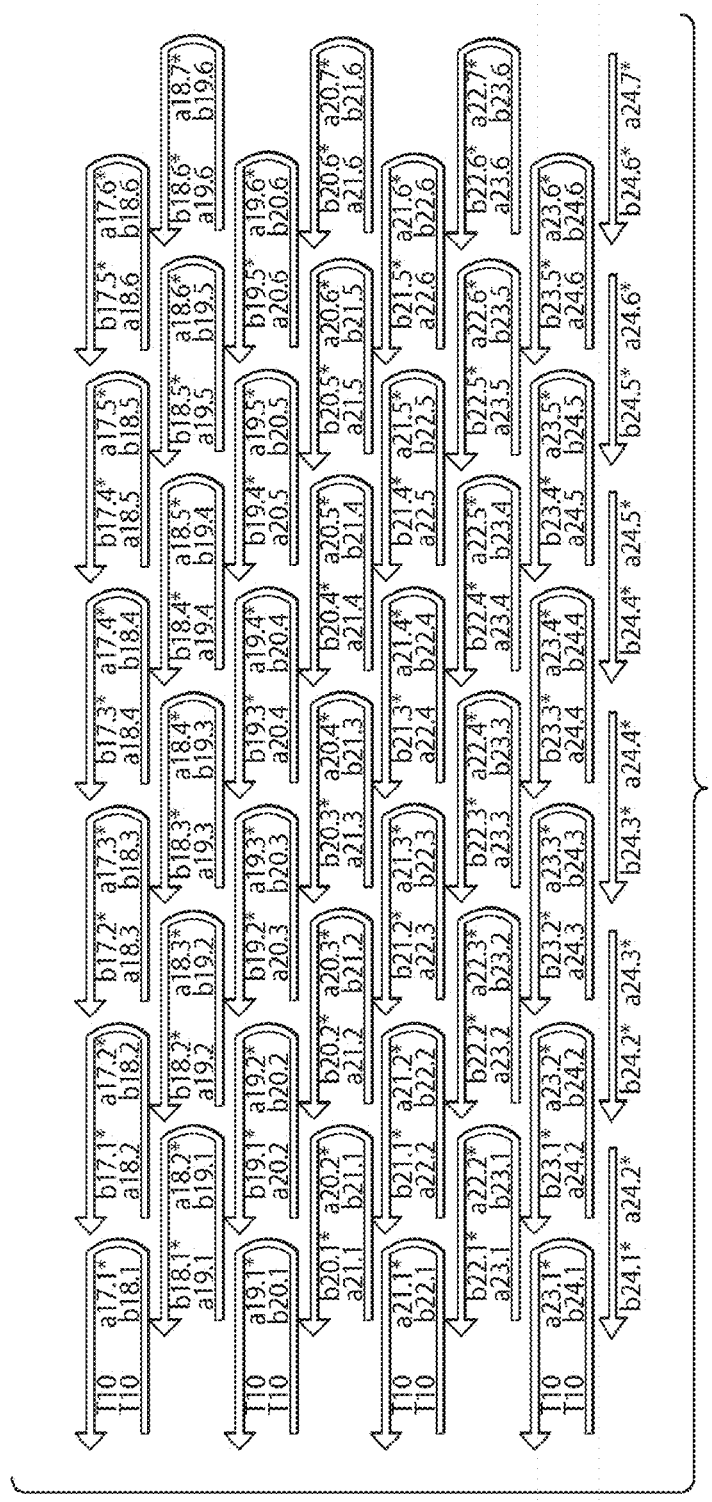

The oligonucleotides within a structure arrange themselves to form double helices, typically in a parallel arrangement. These double helices are referred to herein interchangeably as helices. Examples of such structures are provided in FIG. 3A. The left panel illustrates a 4 helix lattice structure and the right panel illustrates an 8 helix lattice structure. These double helices form as a result of the sequence-specific annealing of a select population of single stranded oligonucleotides to each other. Each double helix in the structure is comprised of a plurality of domains. Those domains bind to complementary domains in other oligonucleotides to form the helix. Adjacent helices are connected to each other by half-crossovers.

The invention provides that a nucleic acid structure may be designed prior to synthesis and its size, shape, complexity and modification may be prescribed and controlled by using certain select oligonucleotides in the synthesis process. As an example, FIGS. 3B-F illustrate an oligonucleotide map for a number of lattices of varying size. The location of each domain and each oligonucleotide in the structure is known and provided for in these Figures. The nucleotide sequences of the domains and the oligonucleotides are provided in Table 1.

The oligonucleotides of Table 1 may be used to generate a 310 "pixel" canvas from which various shaped nucleic acid structures may be generated. The Table contains the sequences of 4-domain internal and boundary oligonucleotides and the sequences of 2-domain boundary oligonucleotides. The 4-domain internal oligonucleotides represent pixels while the 2-domain and 4-domain boundary oligonucleotides bind to the top, bottom and side edges of the structure created by the internal oligonucleotides, thereby preventing unwanted aggregation of structures. The Table therefore comprises 310 4-domain (pixel or internal) oligonucleotides, 24 4-domain (vertical boundary) oligonucleotides, and 28 2-domain (horizontal boundary) oligonucleotides. It is to be understood that, when subsets of the 310 internal oligonucleotide pool are used to generate a structure of particular shape, different 2-domain and 4-domain boundary oligonucleotides may be needed depending on the sequences present at the edges of the desired structure of internal oligonucleotides. One of ordinary skill in the art is capable of determining the sequence of such boundary oligonucleotides using the teaching provided herein and with reference to certain of the Figures including without limitation FIGS. 2B and 3A.

It should be understood therefore that the internal oligonucleotides contribute to the desired shape of the structure and the boundary oligonucleotides prevent unwanted aggregation of structures to each other.

It should also be understood that the sequences of Table 1 are representative in nature and that the invention may be carried out using another oligonucleotide pool. Such oligonucleotide pools may be designed manually or by computer means based on the teachings provided herein.

As an example, oligonucleotide pools may be constructed using a process that minimizes the sequence symmetry or that populates the SST motifs with completely random sequences. Either process may employ software such as Uniquimer. For the sequence minimization based design, there are several criteria for sequence generation: 1) Nucleotides (i.e. A, C, G, T) are randomly generated one-by-one. 2) Complementary nucleotides to those generated are matched following the base pairing rule: A to T and vice versa, C to G and vice versa. 3) No repeating segment beyond a certain length (8 nt or 9 nt) is permitted. When such repeating segments emerge during design, the most recently generated nucleotides will be mutated until the repeating segment requirement is satisfied. 4) No four consecutive A, C, G or T bases are allowed. 5) Pre-specified nucleotides at the single-stranded linkage points (e.g. T and G for the 21st and 22nd nucleotides, respectively, for most of the strands) are used to avoid sliding bases around the linkage points. In the design using completely random sequences, however, restrictions in steps 3 to 5 are not applied.

Some or all of the oligonucleotides may be manually designed. For example, in some of the exemplified structures, manual design and/or optimization was used for the handle segment sequence design (e.g. handle segment to accommodate 3' biotin strand for streptavidin labeling and concatenation of poly-T domains). Additionally, in some cases, segments from different SST structures were manually combined to transform an existing structure into a new structure. For example, additional rows of SSTs were introduced to convert a rectangle design into a tube design (e.g. converting a 24H×28T rectangle design to a 24H×28T barrel design, and converting a 24H×28T rectangle design to a 8H×84T tube design). Similarly, a tube design was also manually converted into a rectangle design (e.g., converting a 12H×177T tube to a 36H×41T rectangle).

In some instances, at least one domain in a nucleic acid structure will be unique, intending that the domain appears only once in that structure. A structure may be comprised of one or more unique domains, including 1, 2, 3, 4, 5, 6, 7, 8, 9, 10, 20, 30, 40, 50, 60, 70, 80, 90, 100, 200, 300, 400, 500, 600, 700, 800, 900, 1000 or more unique domains. In some embodiments, at least 10%, 20%, 30%, 40%, 50%, 60%, 70%, 80%, 80%, or 90% of the domains in the structure are unique. As an example, a structure may comprise a first plurality of domains each of which appears only once in the structure and these unique domains may present 75% of the total domains in the structure, and a second plurality of domains each of which appears more than once in the structure and these repeating domains may represent 25% of the total domains in the structure. It will be apparent that other percentages are also possible. In some embodiments, every domain in a structure is unique. Every domain in a composite structure (i.e., a structure comprising two or more nucleic acid structures linked to each other with a spacer-linker) may or may not be unique.

Figures 3, 3E, 4:
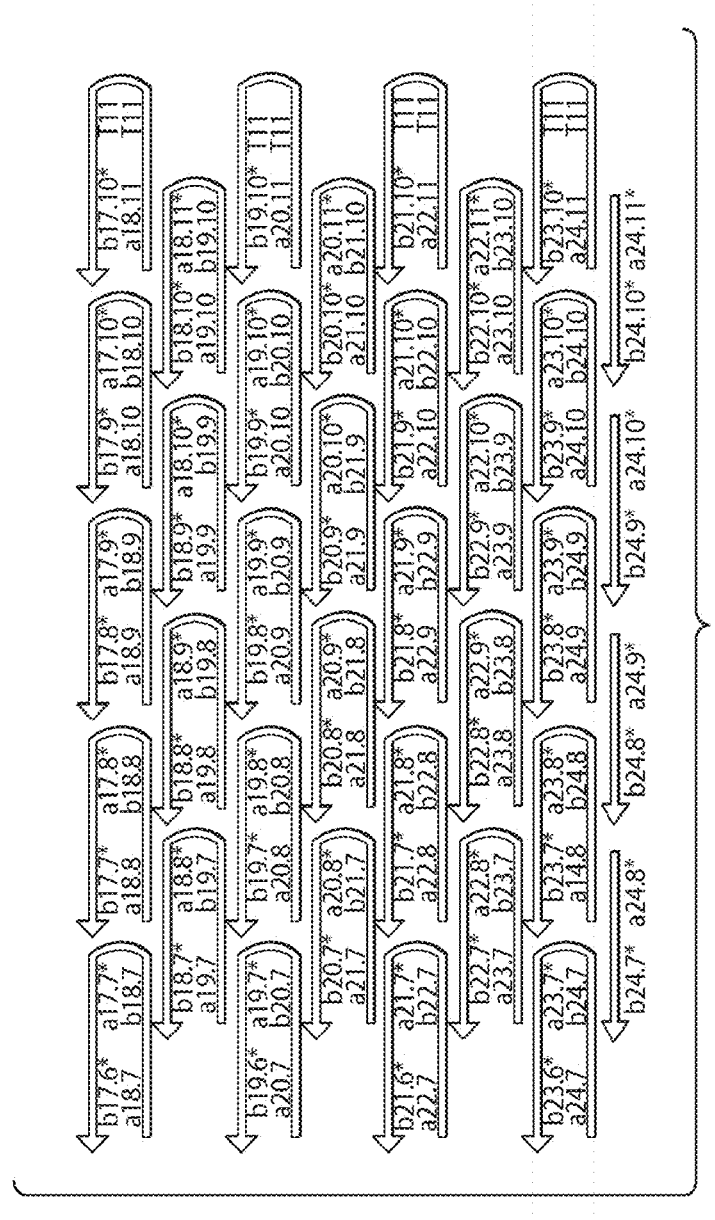
FIG. 4 is a schematic of a plurality of single stranded oligonucleotides combined and annealed to form a lattice nucleic acid structure. Also shown is the agarose gel electrophoresis analysis of the products of the annealing process in the absence of purification, and atomic force microscopic (AFM) images of those products. The scale bar represents 100 nm.
Figure 3F:
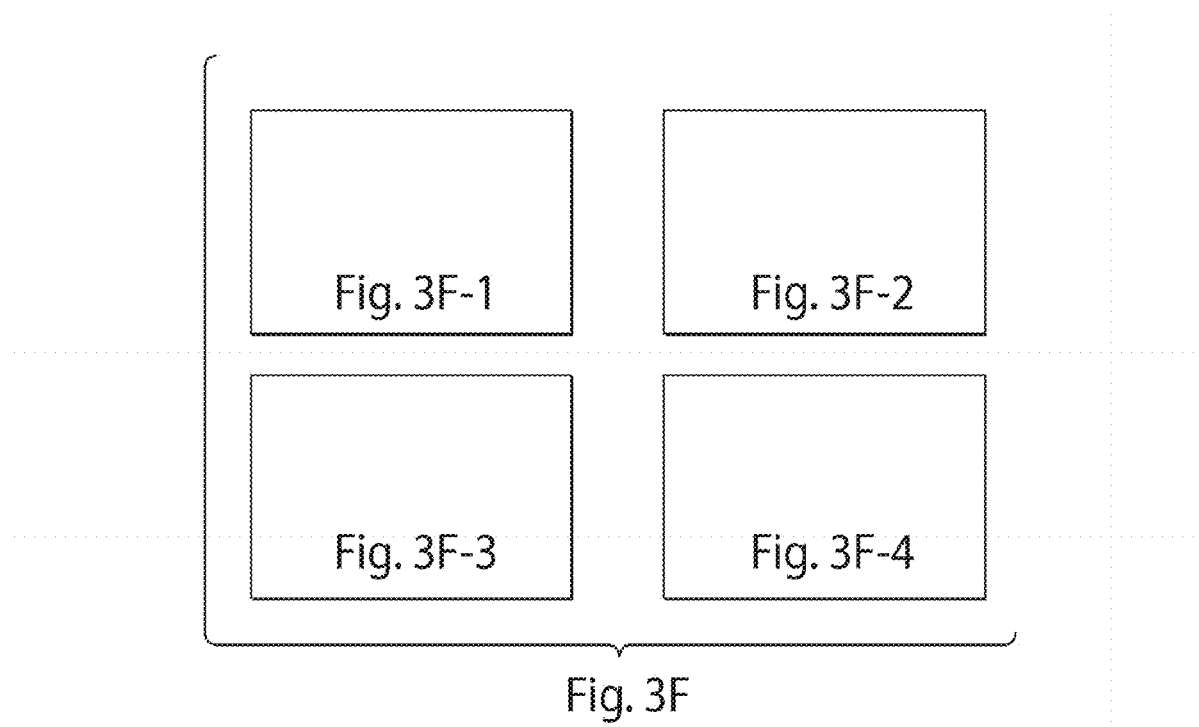
Figures 1, 3F:
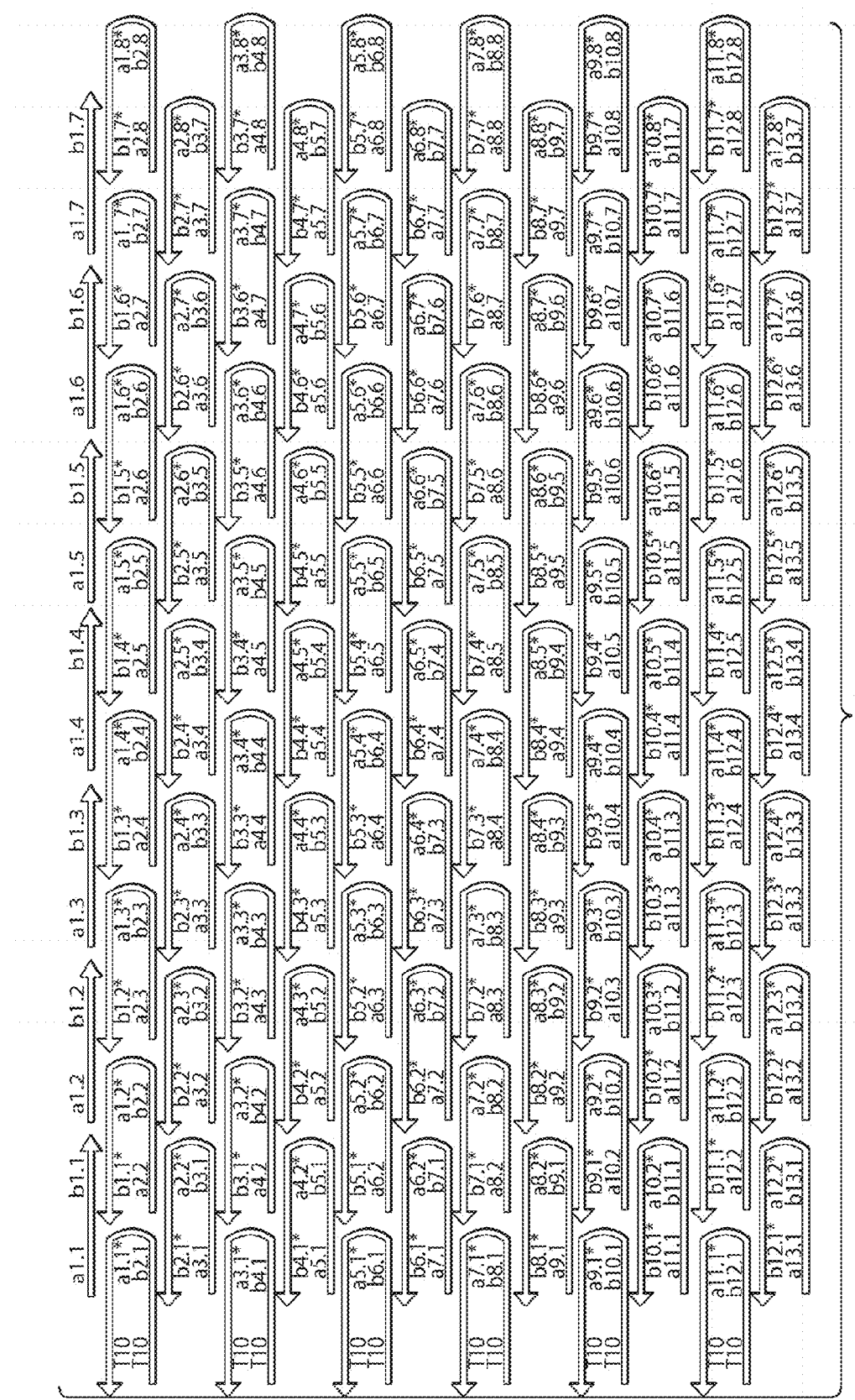
Figures 2, 3F:
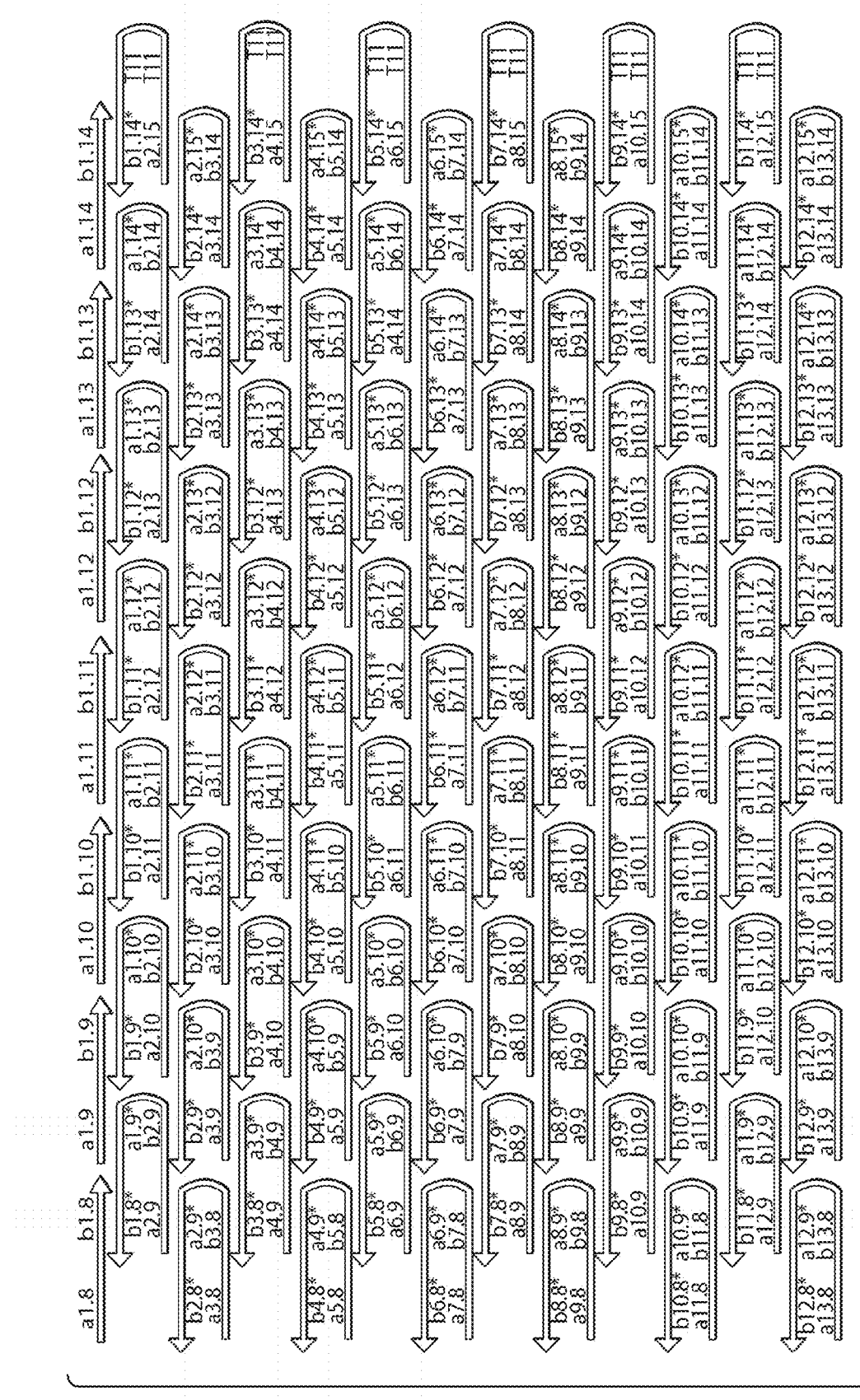
Figures 3, 3F:
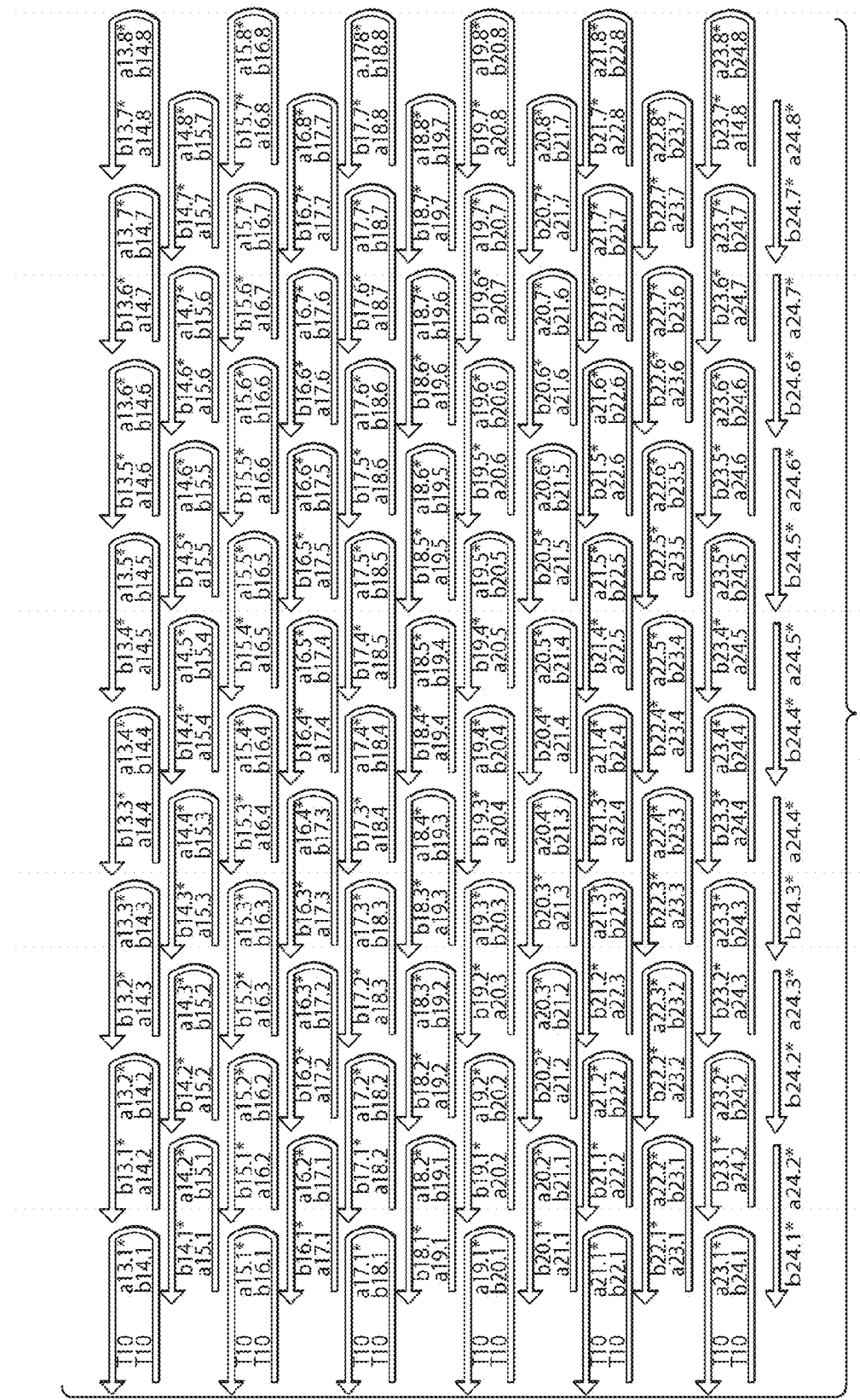
Figures 3, 3F, 4:
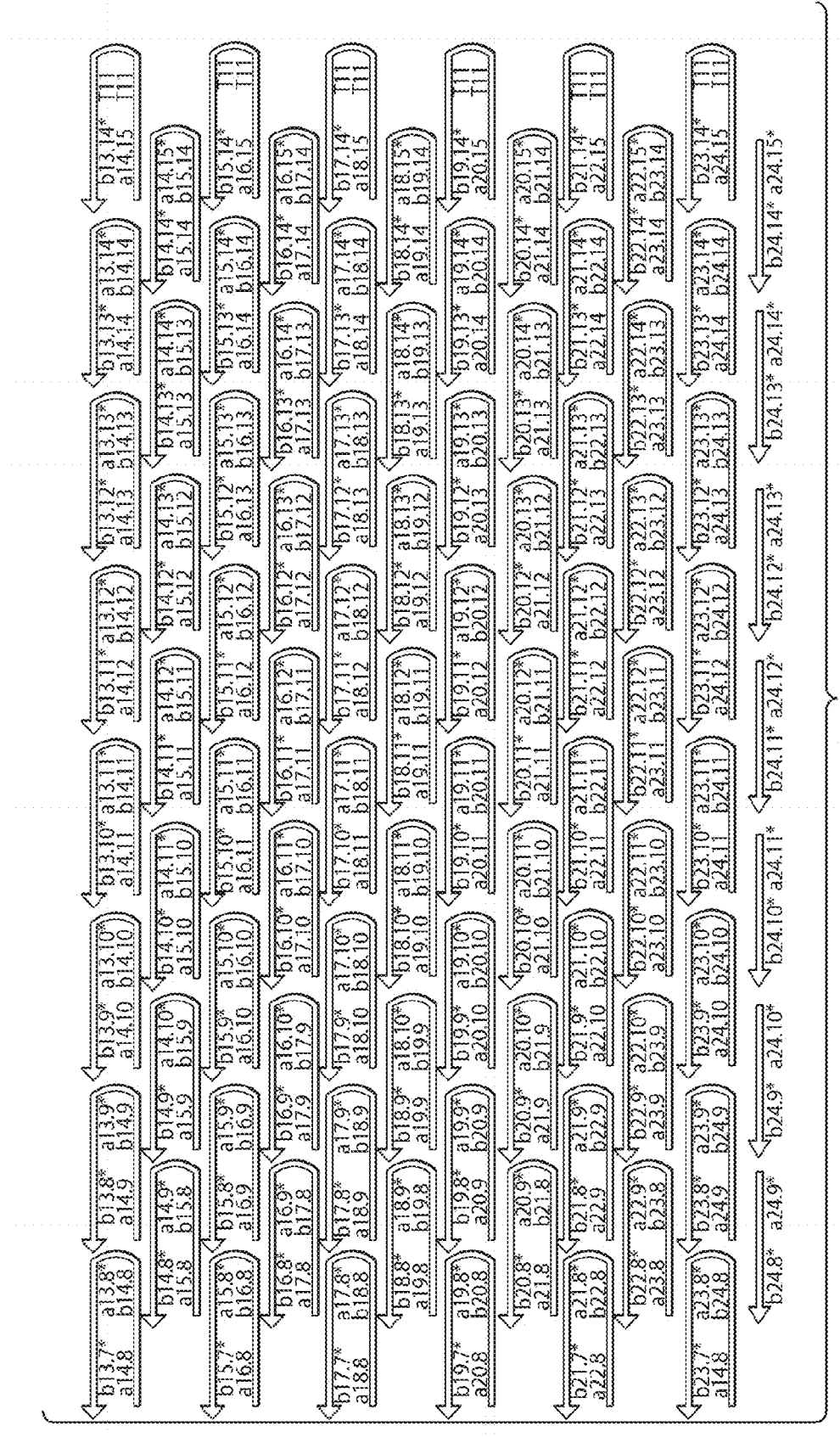
Figure 3G:
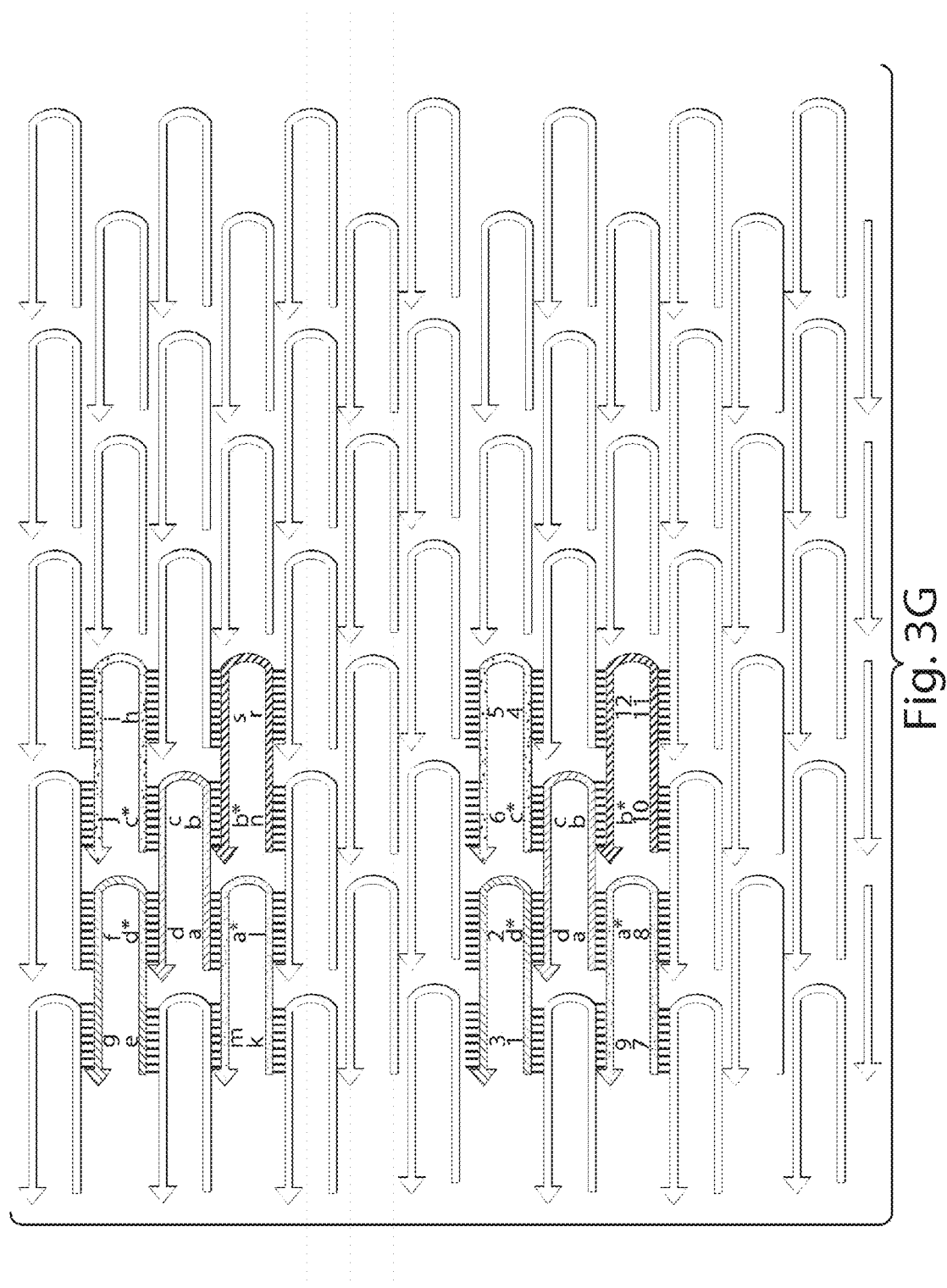
FIG. 3G is a schematic showing a region of a nucleic acid structure having two identical oligonucleotides (labeled as 5' a-b-c-d 3').
Figure 4:
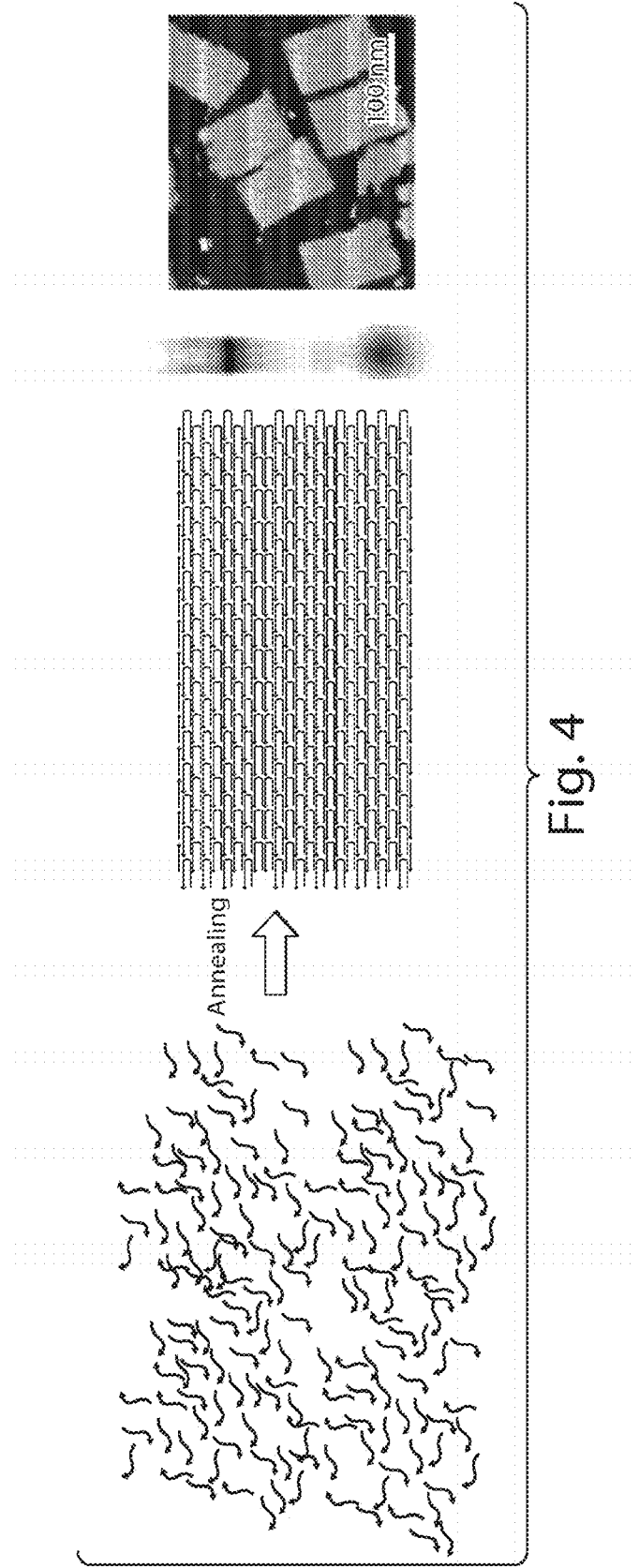

In some instances, at least one domain in a double helix in a structure will be unique, intending that the domain appears only once in that double helix. The domain may be present in other helices within the same structure, and so it may not be unique in the context of the entire nucleic acid structure. This is illustrated in FIG. 3G. The oligonucleotide designated 5'-a-b-c-d-3' is present twice in the structure. Domains designated a and its complement a* and b and its complement b* are present in two helices in the structure as are domains c and its complement c* and d and its complement d*. There may be 1, 2, 3, 4, 5, 6, 7, 8, 9, 10 or more domains in a helix that are unique in the context of that helix. The unique domains in a helix may represent at least 10%, 20%, 30%, 40%, 50%, 60%, 70%, 80%, 80%, 90%, or 100% of the domains in that helix. The unique domains in a helix may be located at or near the ends of the structure. The unique domains in a helix may be contiguous to each other or they may be spread apart from each other. They may be separated from each other by repeating domains (i.e., domains that appear more than once in a helix).

The structures may comprise one or more helices having unique domains. This type of helix may represent at least 10%, 20%, 30%, 40%, 50%, 60%, 70%, 80% or 90% or 100% of the helices present in the structure. If more than one of this helix type is present in the structure, they may be adjacent to each other or they may be separated by other helices including helices that do not contain unique domains. As an example, helices having unique domains may alternate in the structure with helices lacking unique domains.

Thus, in some instances, the nucleic acid structure may comprise two or more helices each having one or more unique domains, wherein the domain is unique in the context of an individual helix itself, and possibly unique within the context of the structure as a whole. The unique domain(s) in an individual helix may be present in other helices in the structure. The unique domain(s) in an individual helix may be the unique domain(s) in other helices in the structure.

In some instances, one or more helices in the structure each may be comprised entirely of unique domains, intending that each of those domains is present only once per helix or is present only once per structure.

Thus, in some instances, the nucleic acid structures of the invention comprise at least one unique double helix. A unique double helix is a helix having a domain composition that is different from any other helix in the structure. The unique double helix would therefore also have a nucleotide sequence that is different from any other helix in the structure.

In still other instances, the nucleic acid structures of the invention may be designed such that they comprise one region that is comprised of unique domains and another region that is comprised of non-unique or repeating domains.

The structures are formed, at least in part, by annealing a plurality of known oligonucleotides in a single vessel. This is illustrated in FIG. 4. The Figure shows the schematic of the expected lattice structure and the AFM image of the post-annealing process. The gel electrophoresis analysis of the post-annealing process shows two bands, one corresponding to the unbound oligonucleotides and one corresponding to the structure. The methods provide that, starting with a known pool of oligonucleotides that can be used to generate a lattice of a certain size, select oligonucleotides may be excluded from the pool in order to form different shaped and/or sized structures.

Figure 5A:
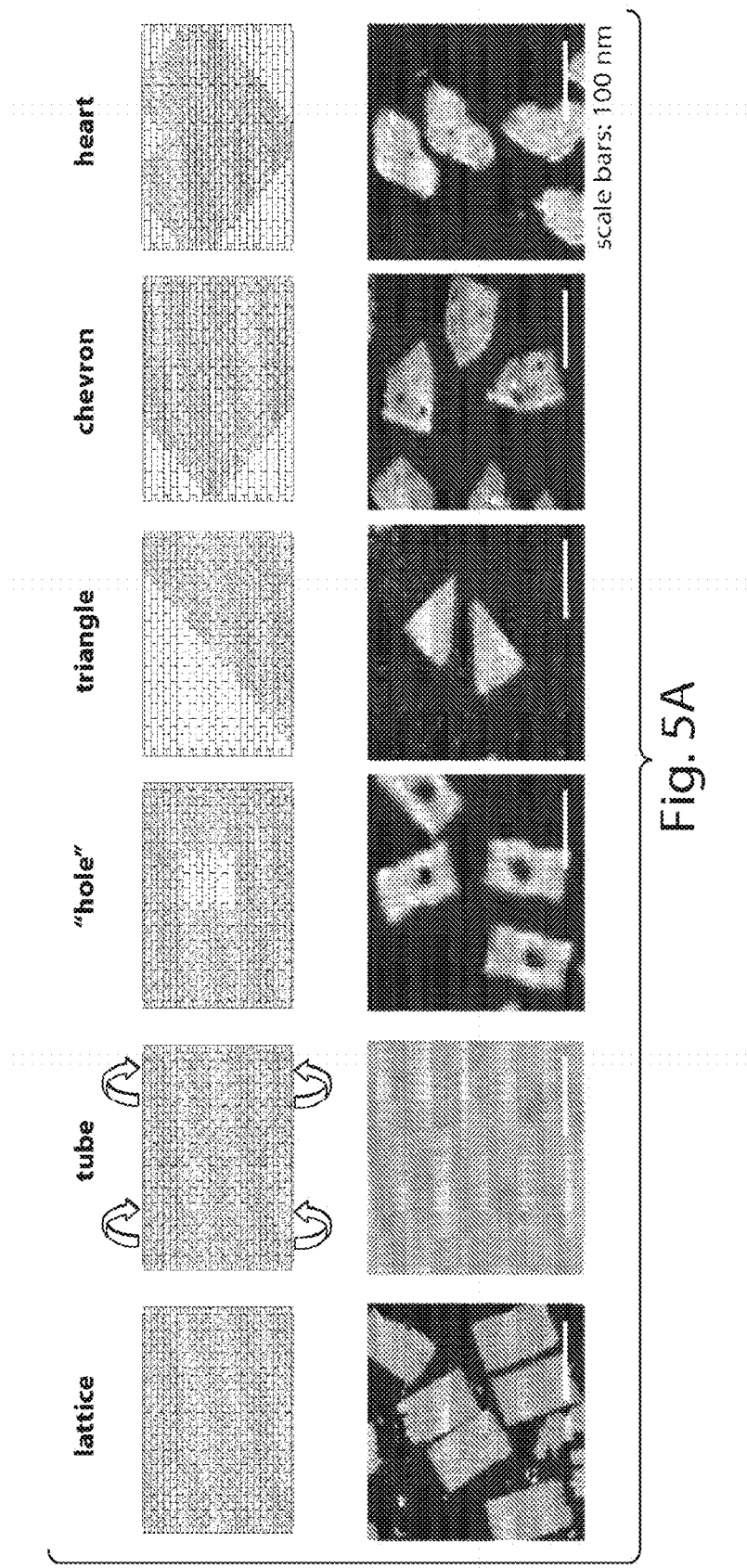
FIG. 5A is a schematic of variously shaped nucleic acid structures (top) and AFM images of the post-annealing products (bottom). The scale bar represents 100 nm. The schematics also illustrate the methodology for generating the variously shaped nucleic acid structures using an initial lattice structure having a known oligonucleotide map.
Figure 5B:
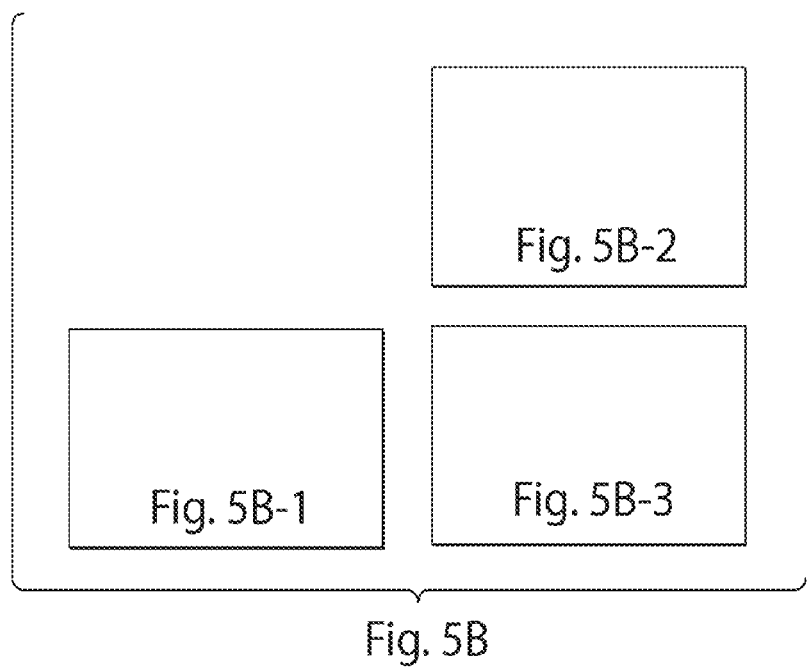
FIGS. 5B and C are schematics of two triangular shaped nucleic acid structures of different size and with different edges. Both structures have been made experimentally.
Figures 1, 5B:
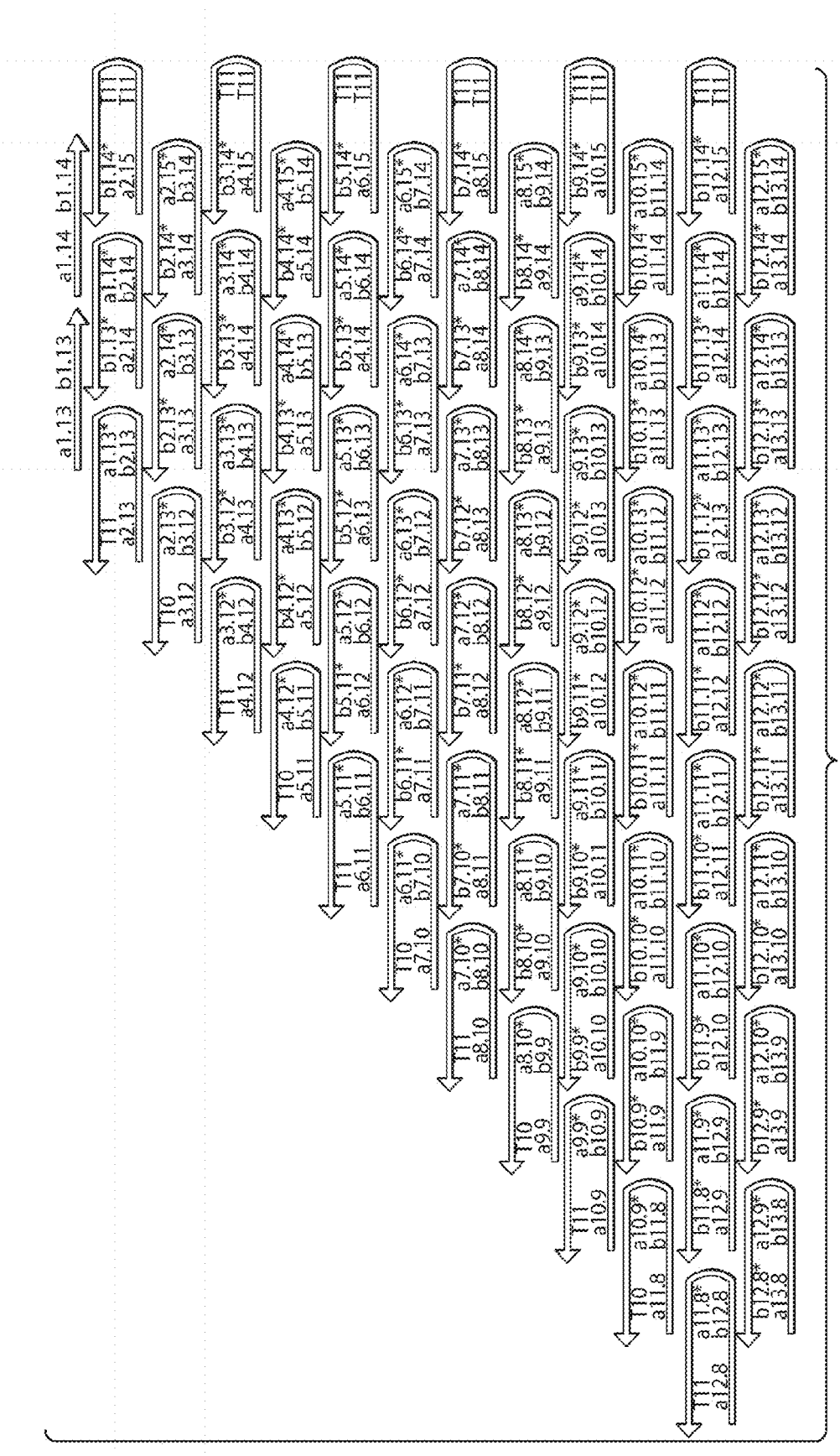
Figures 2, 5B:
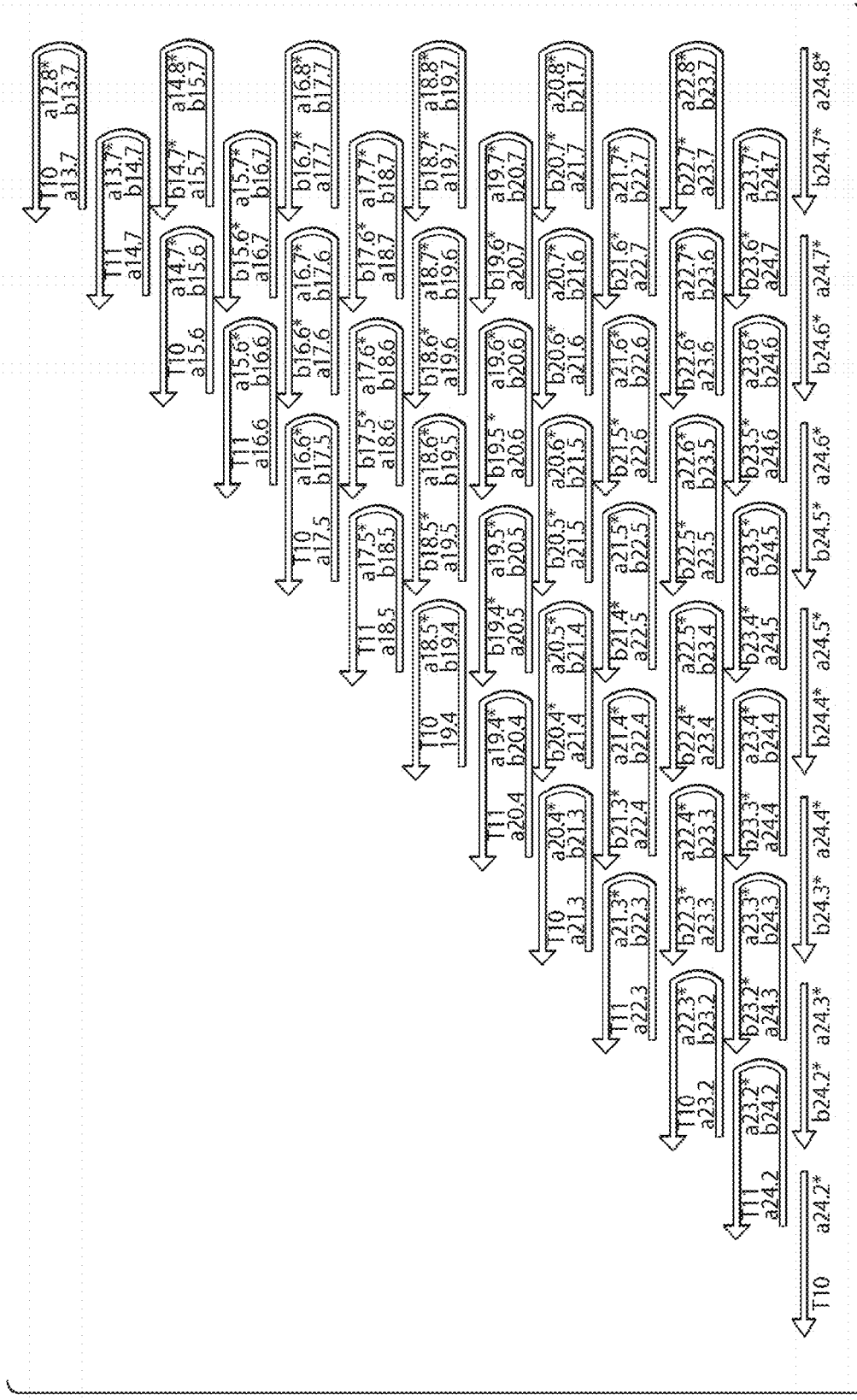
Figures 3, 5B:
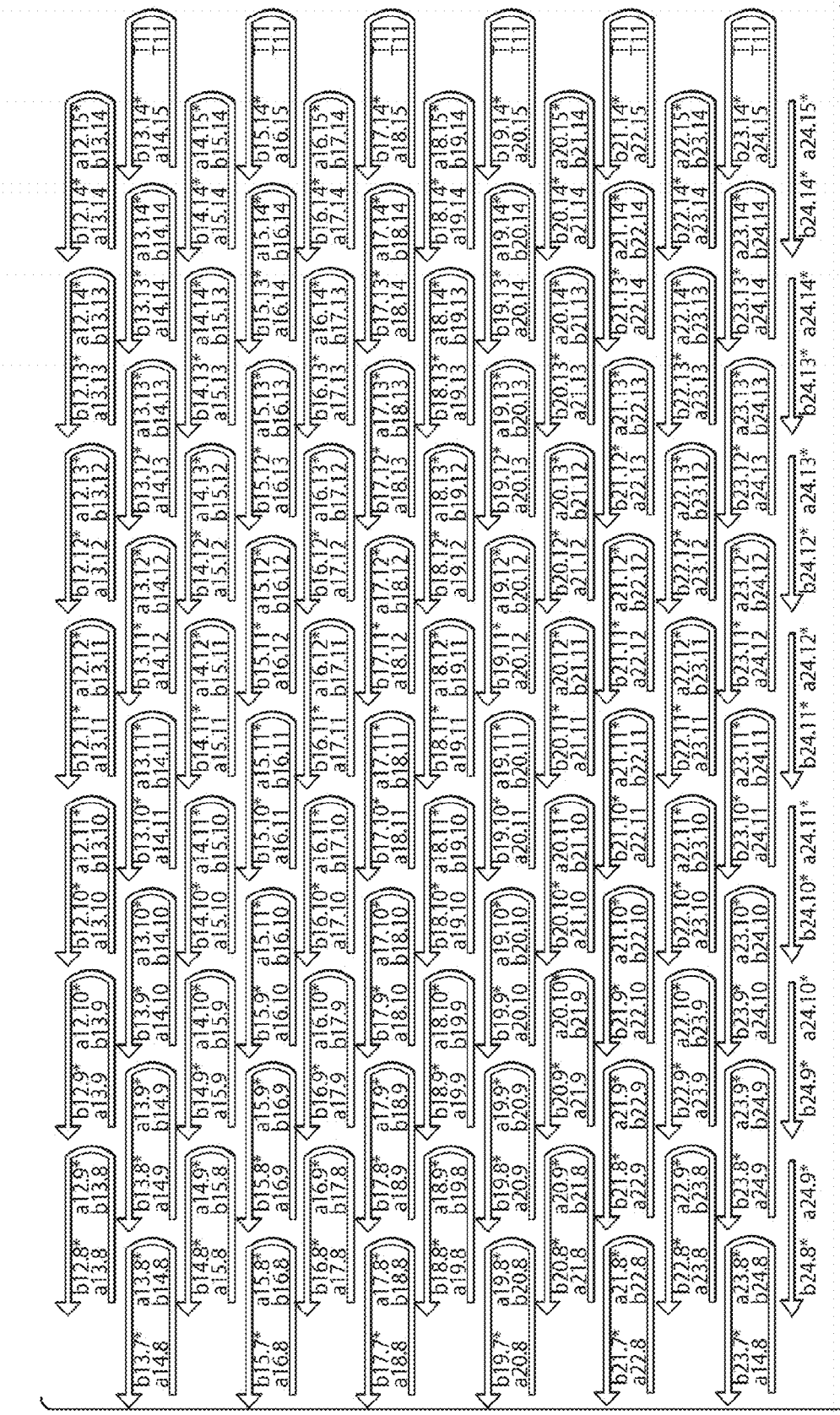
Figure 5C:
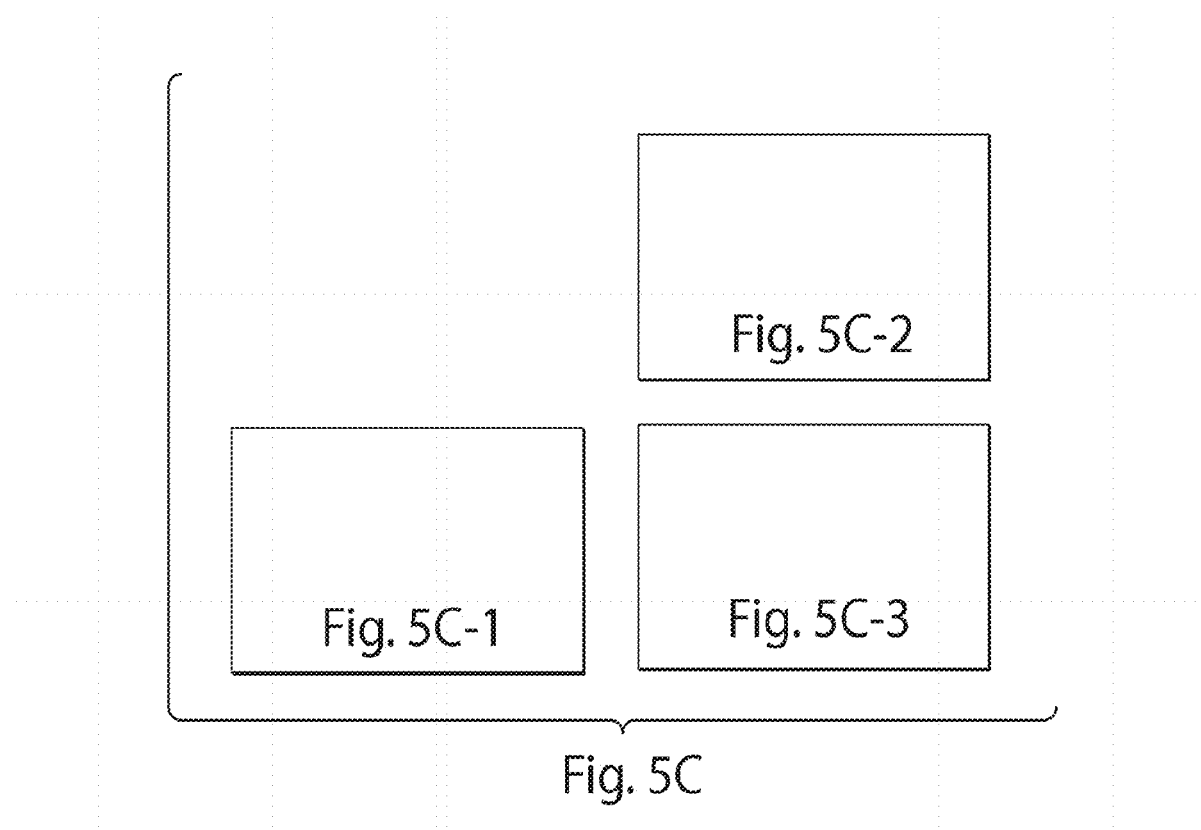
FIG. 5D is a schematic of a lattice that can be made into a tube. Domains a24.x* and b24.x* of the top row will bind to a24.x and b24.x of the bottom row respectively to form the tube shape.
Figures 1, 5C:
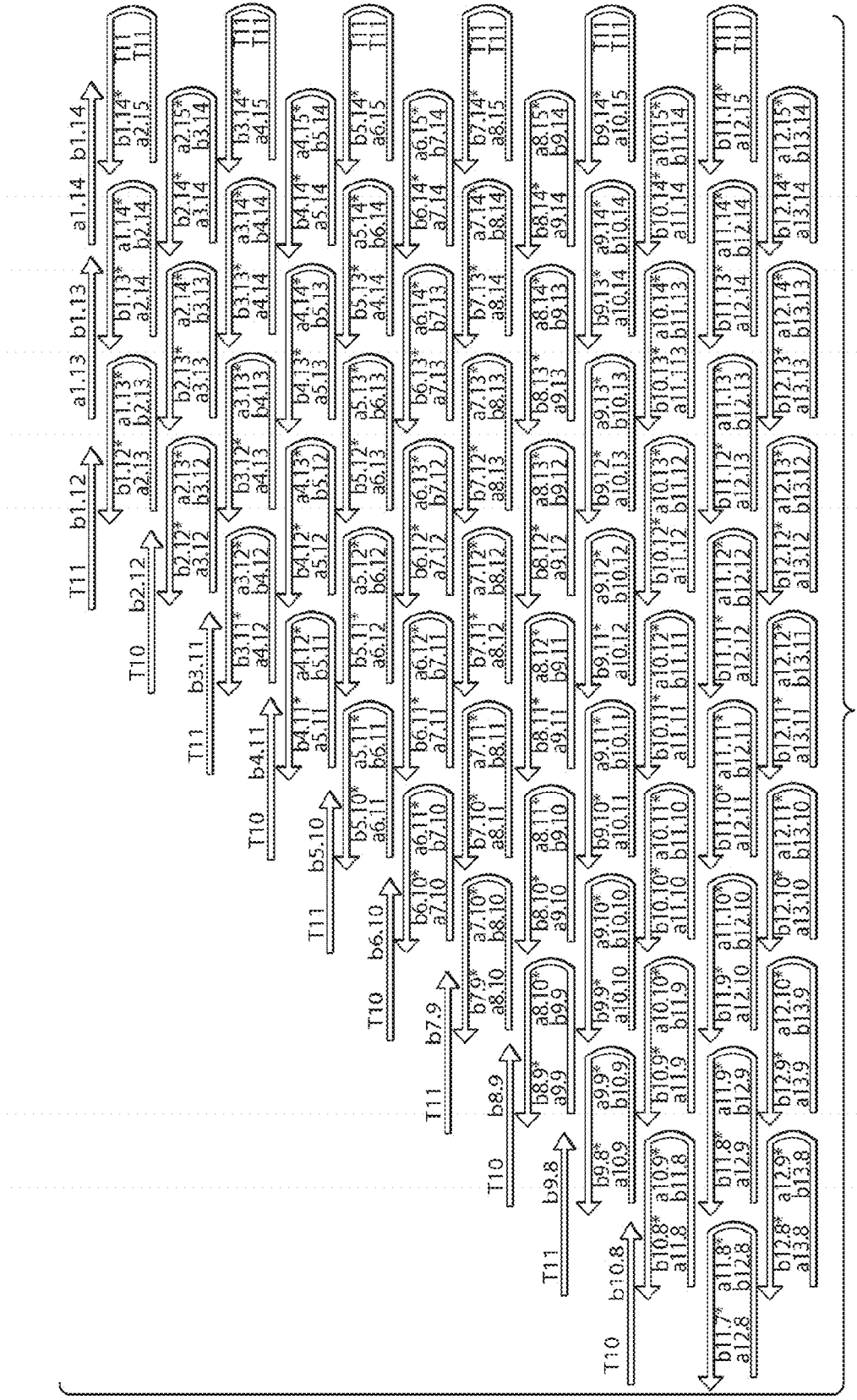
Figures 2, 5C:
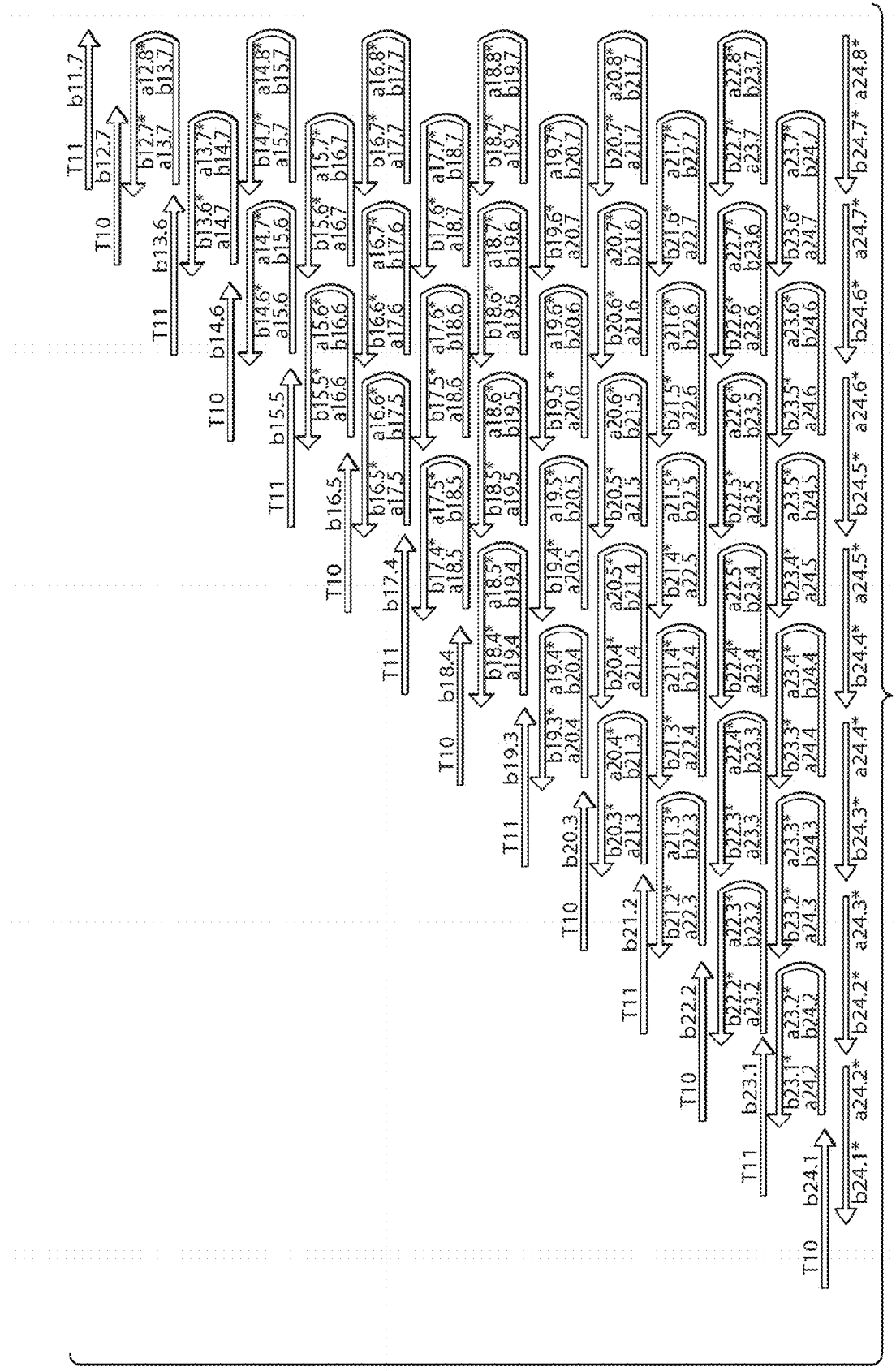
Figures 3, 5C:
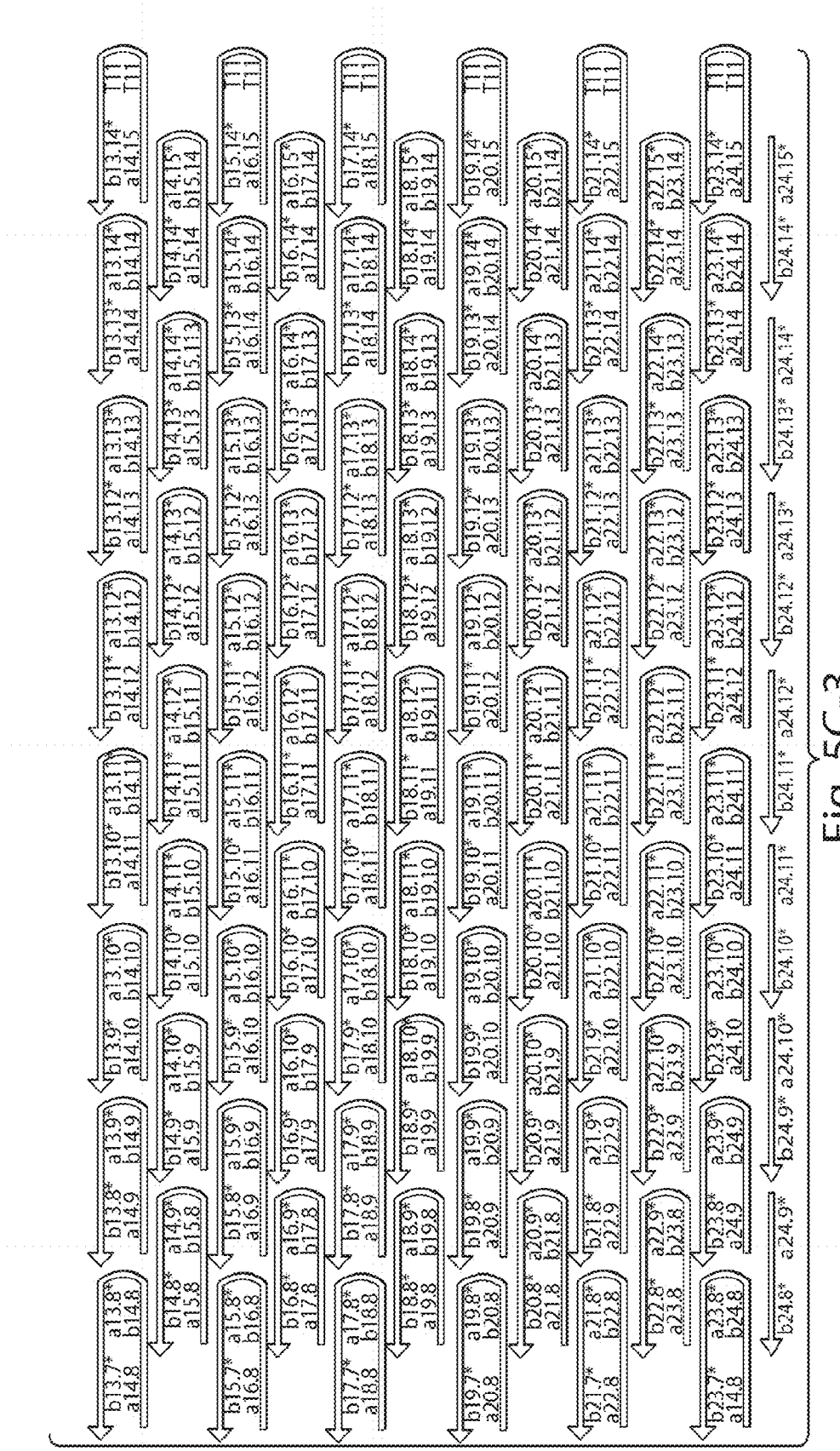
Figure 5D:
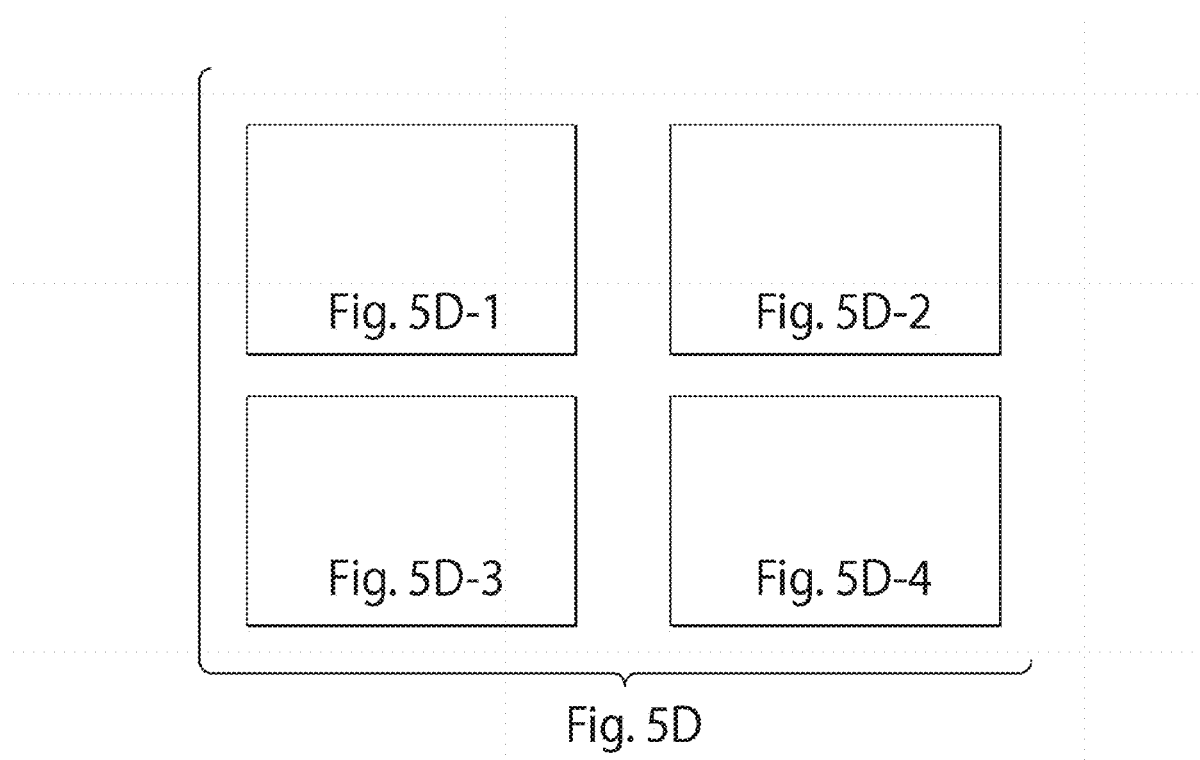
Figures 1, 5D:
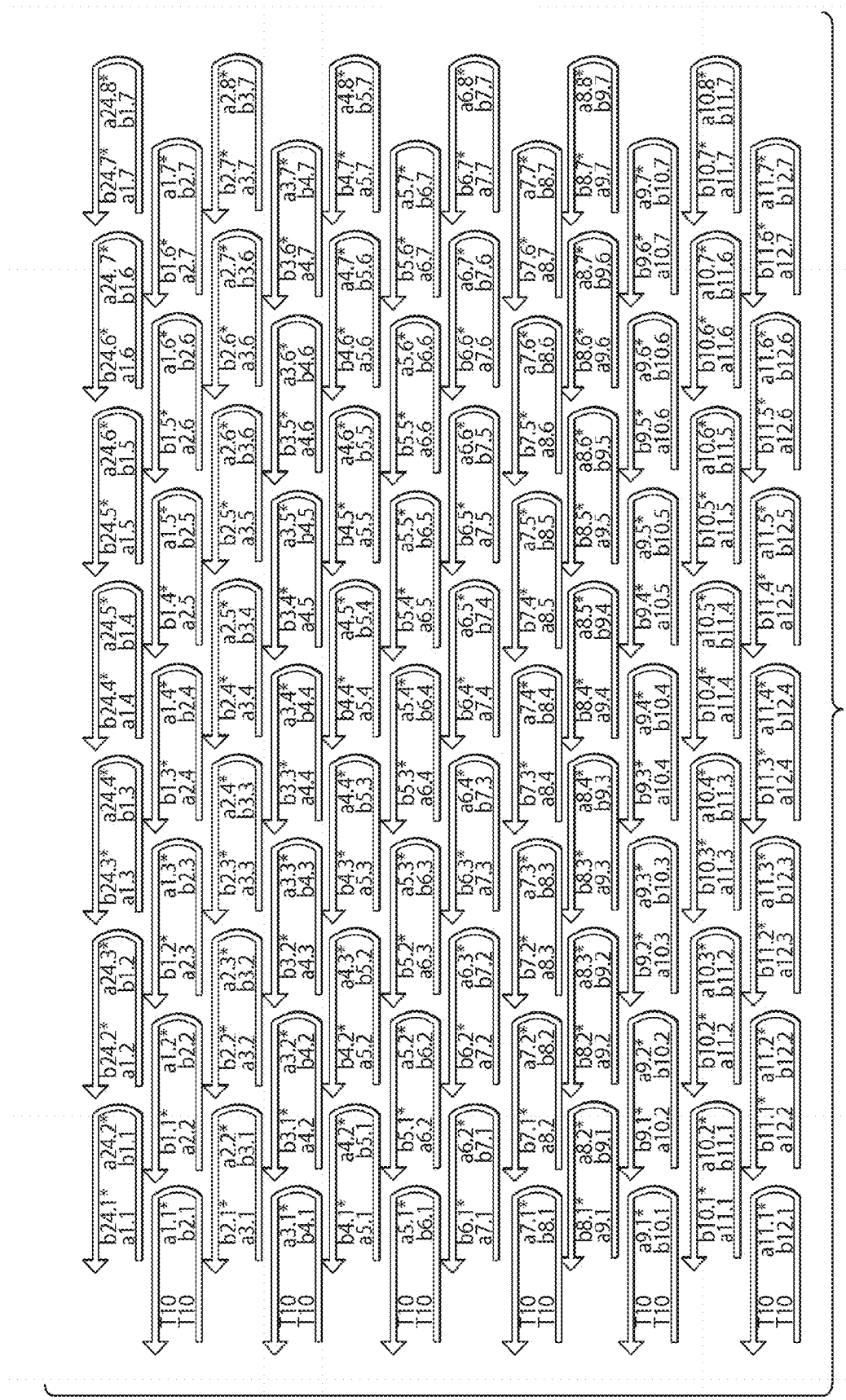
Figures 2, 5D:
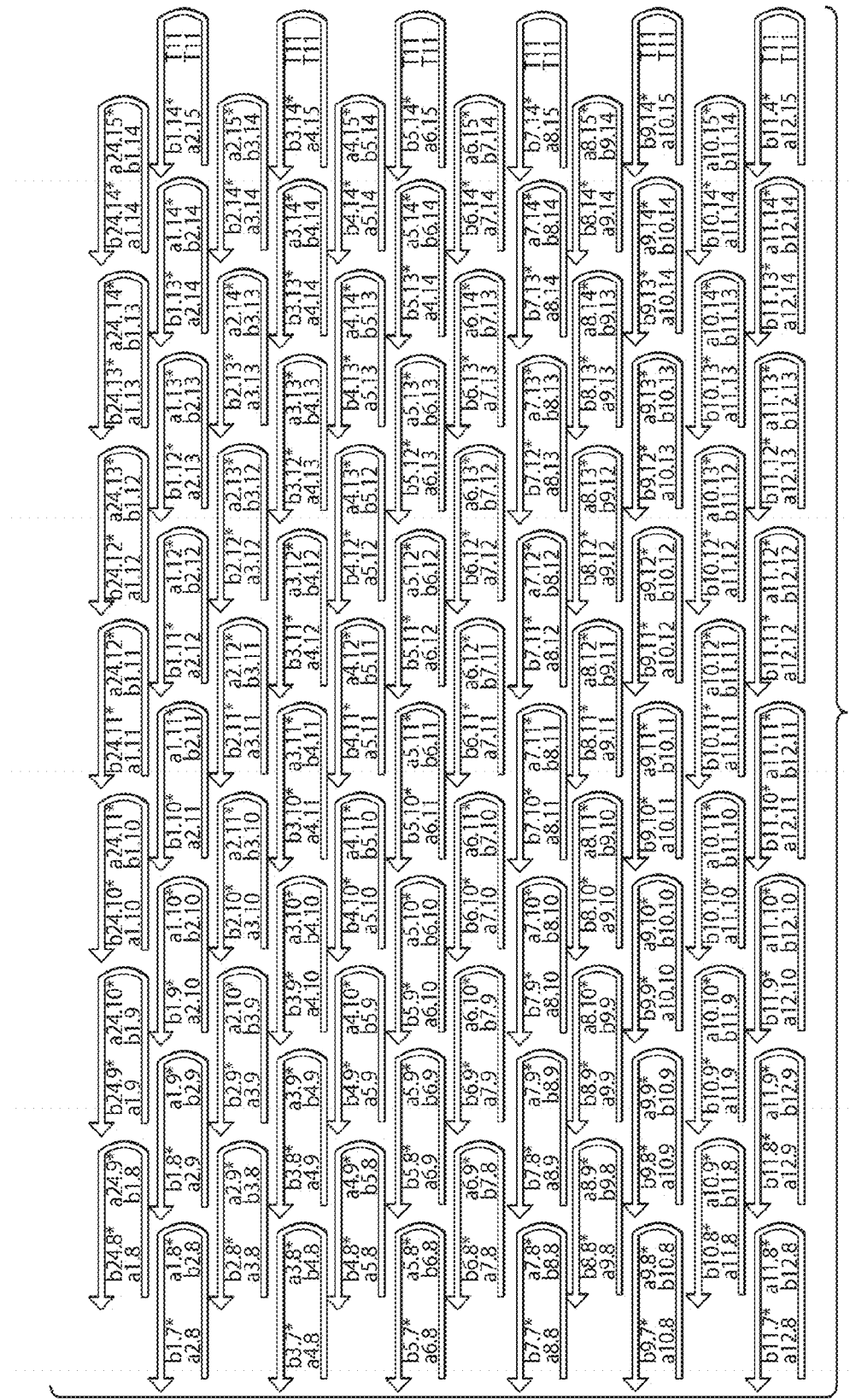
Figures 3, 5D:
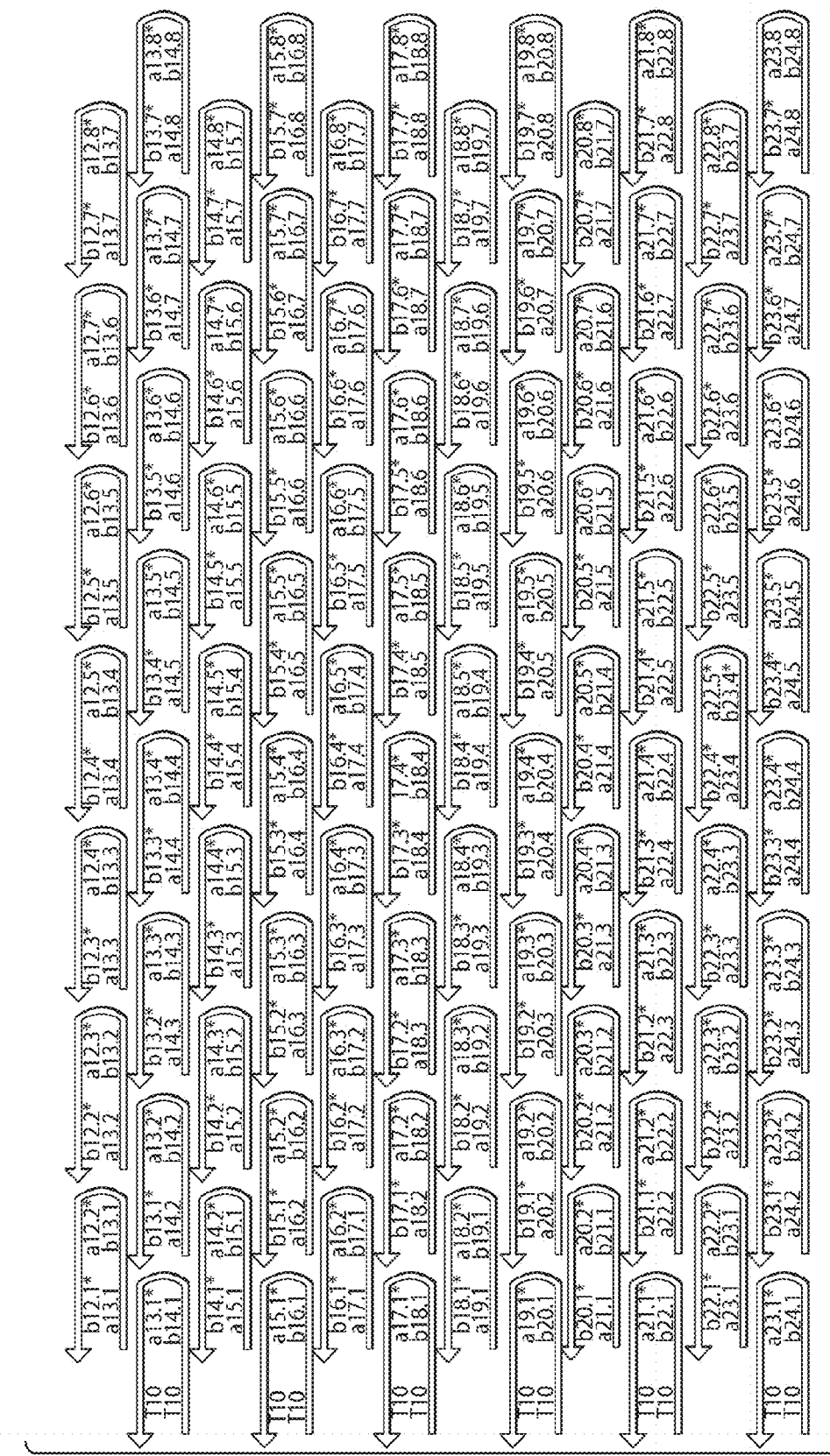
Figures 4, 5D:
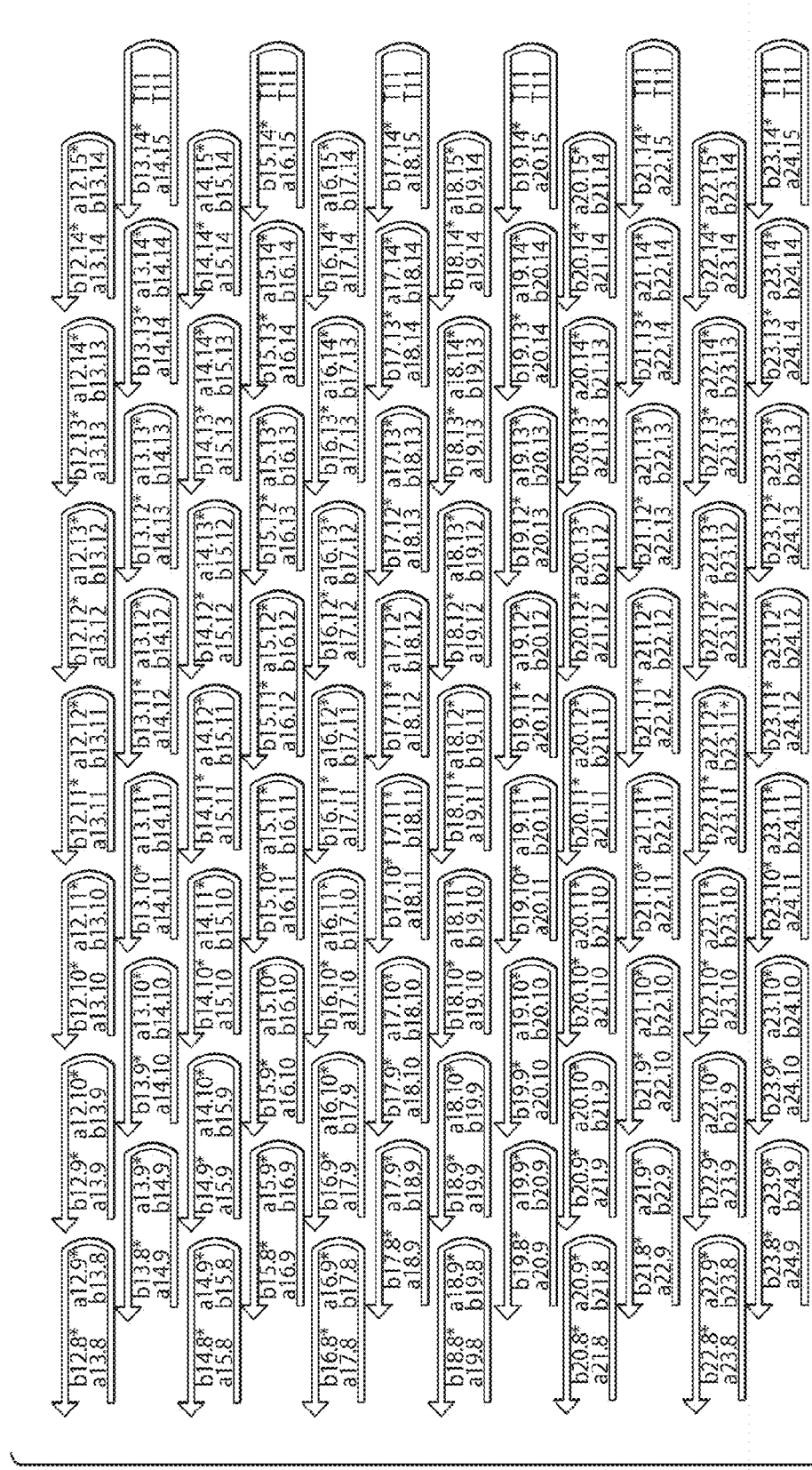
Figure 6:
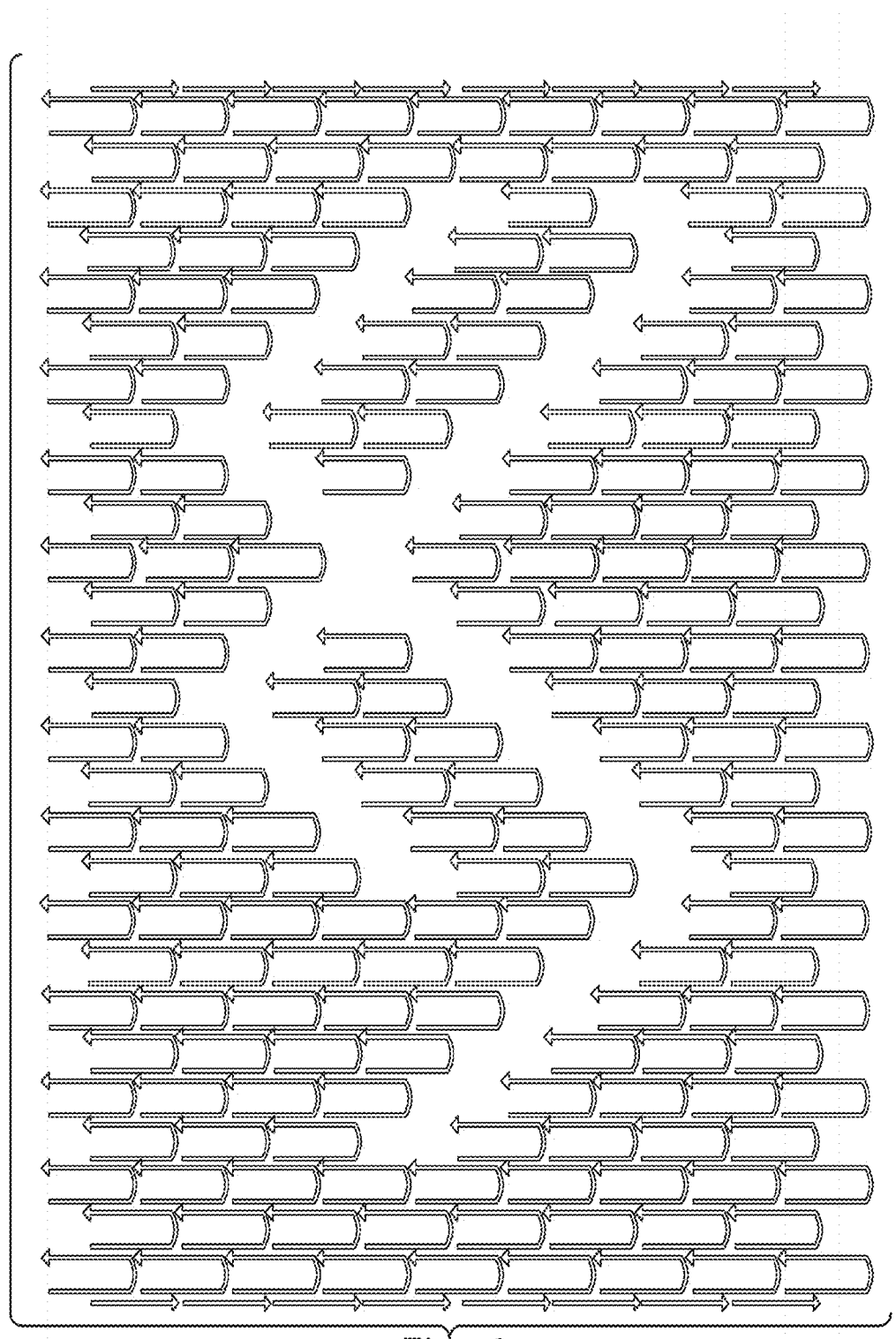
FIG. 6 is a schematic of a rectangular nucleic acid structure having an internal region that is devoid of oligonucleotides. The Figure illustrates the ease with which such complex structures may be formed by simply excluding known oligonucleotides from the plurality used to make the structure based on the predetermined and known oligonucleotide map of the structure.
Figure 7:
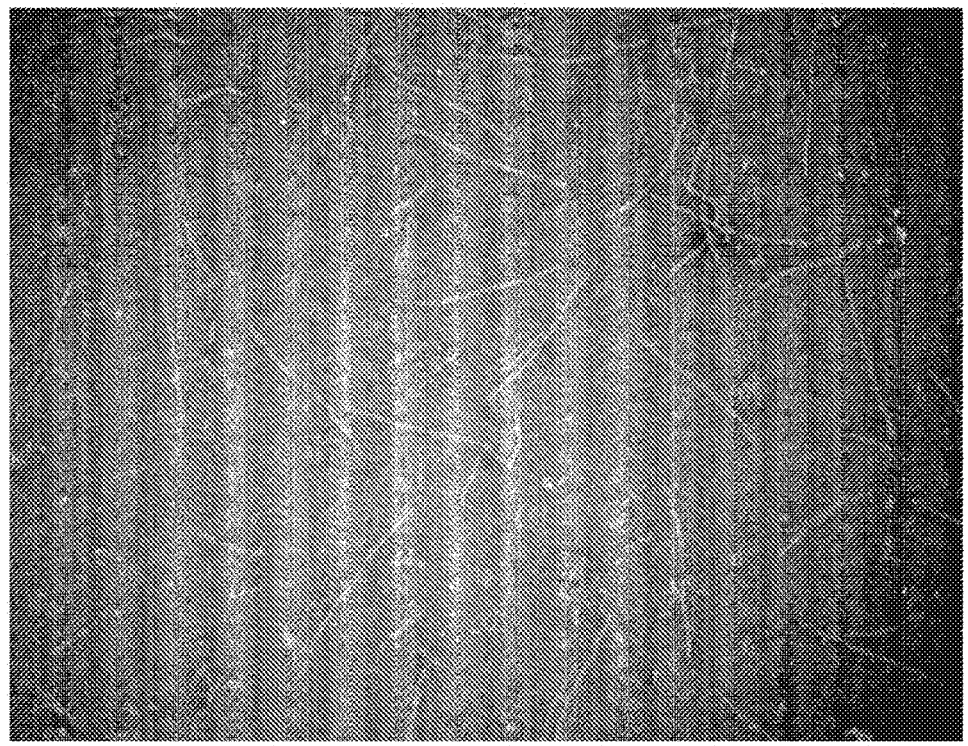
FIG. 7 is a transmission electron microscopy (TEM) image of a tubular nucleic acid structure made from a lattice that is three times the length and one-third the width of the rectangular lattice of FIG. 5. These tubes were generated using about 80% of the oligonucleotides required for the lattice and including some additional oligonucleotides to serve as connectors.

A variety of structures that may be made using these methods are shown in FIG. 5A (top). Also shown are the post-annealing products resulting from such methods. Detailed oligonucleotide maps that can be used to generate triangular structures are also provided in FIGS. 5B and C. A detailed oligonucleotide map that can be used to generate a tube-shaped structure is provided in FIG. 5D. The invention contemplates exclusion of oligonucleotides internal to a structure as well. As an example, FIG. 6 illustrates a structure having an internal void pattern (i.e., a predetermined region lacking any oligonucleotides).

Thus, in some instances, an end user designs a nucleic acid structure, such as for example a lattice having a particular length and a width dimension, with knowledge of the particular oligonucleotide present at each position in the structure. In effect, the end user has a physical map that denotes the precise location of each oligonucleotide within the structure. Knowledge of the identity of each oligonucleotide at each location in the map (and thus in the nucleic acid structure) allows the end user to engineer particular patterns or shapes using a particular structure as a starting point. Such engineering can occur by excluding one or more known oligonucleotides from the mixture of oligonucleotides combined to form the nucleic acid structure and/or including additional known oligonucleotides.

Thus, as an example and as demonstrated herein, an end user may design a two dimensional lattice having a particular length and width, and comprised of a plurality of unique oligonucleotides. The end user knows the identity of the oligonucleotide at each position in the lattice. In addition to being able to synthesize the lattice itself, the end user is also able to design and synthesize one or more other nucleic acid structures using the lattice as a starting point. As demonstrated herein, variously shaped nucleic acid structures may be synthesized by excluding one and usually more oligonucleotides from the pool that would be used to make the entire lattice. These shapes include heart shapes, chevrons, and triangles, as well as lattices or other structures with internal openings or holes.

The invention therefore provides a methodology for synthesizing a number of different nucleic acid structures without having to design each structure de novo. Rather, starting with an initial nucleic acid structure, such as a lattice, a variety of other nucleic acid structures may be formed simply by excluding preselected oligonucleotides and/or including preselected oligonucleotides. In this way, the end user uses the single stranded oligonucleotides in a modular manner, including or excluding members of the plurality depending upon the ultimate shape and size of nucleic acid structure desired. The interactions between oligonucleotide members of the plurality are not expected to change appreciably and therefore it is not necessary for an end user to design, essentially from scratch, every new nucleic acid structure. Instead, the end user prepares stocks of each oligonucleotide and combines various stocks together, at relative concentrations corresponding to their relative frequency in the structure and in a single vessel, in order to form a nucleic acid structure of desired shape, size and complexity.

The selection and arrangement of single stranded oligonucleotides in a nucleic acid structure of desired shape and size can be done manually or by computer algorithm. An example of such a computer algorithm is Uniquimer, which is openly available to the public.

As illustrated in some of the foregoing Figures, the size of the nucleic acid structures of the invention may be controlled during the annealing process. This size control is achieved by designing structures having one or more unique domains, or one or more unique helices and thus using select populations of oligonucleotides in the annealing process. The size of the nucleic acid structure thus is typically also predetermined.

The size of a nucleic acid structure may be represented by distance of one, two or three of its dimensions. Such dimensions may each independently be nanometers or micrometers in length, or longer. As an example, the structure may comprise one or two dimensions each having a length in the range of 5-100 nanometers, 5-500 nanometers, 5-1000 nanometers, including 10-100 nanometers, 10-500 nanometers, or 10-1000 nanometers. In some embodiments, they may have one or more dimensions of about 10, 20, 30, 40, 50, 60, 70, 80, 90, 100, 110, 120, 130, 140, 150, 160, 170, 180, 190, 200, 300, 400, 500, 600, 700, 800, 900 nm or more. In some embodiment, the structure is about 3 nm by 7 nm or about 4 nm by 7 nm. In some embodiments, the structure is 60 nm by 100 nm.

The size of the nucleic acid structure may also be presented by the number of double helices as well as the length of those double helices. The length of a double helix may be expressed as the number of helical turns in the helix. It is to be understood that the invention contemplates making structures that are in the nanometer and micrometer scale, and larger.

The size of the nucleic acid structure may also be presented as the number of 4-domain oligonucleotides (SSTs) it comprises. The range may be from 1 to more than 1000. Many of the structures exemplified herein are comprised of equal to or fewer than 310 SSTs. It is however to be understood that the number of SSTs contributing to a nucleic acid structure may vary depending on the size of structure desired and/or the degree of modification and/or complexity desired. Some of the exemplified structures comprise at least 4-fold more distinct molecular components as compared to previously reported one-pot annealing structures.

The size of the nucleic acid structure may also be presented as the number of nucleotides it comprises. Some of the structures exemplified herein comprise at least about 15,000 nucleotides, and some comprise about 45,000 nucleotides. Some of the exemplified structures comprise at least 3-fold more nucleotides than a typical DNA origami structure (i.e., a structure comprised of a single scaffold strand and a plurality of staple strands).

The nucleic acid structures of the invention may take any shape or form. Examples of various shapes and forms that may be created using the methods of the invention are illustrated in FIGS. 5A-D, 6, 7 and 11. Importantly, using the methodology of the invention, it is possible to predetermine and thus predesign the shape, form and size of the nucleic acid structure with precise control based on knowledge of the identity (and thus sequence) of oligonucleotides at every location in the structure. The efficacy of the methods is demonstrated by a 94% success rate in generating 103 out of 110 structures of interest in a first attempt. Of the 7 structures that were not generated in a first attempt, 4 were slightly redesigned, primarily by removing narrow connecting points and regions, and then were subsequently successfully produced. Significantly, different structures made using different subsets of, for example, the 310 oligonucleotide pool could be mixed post-synthesis and purification without loss of structural integrity even when the different structures comprised identical SSTs.

Figures 1, 8:
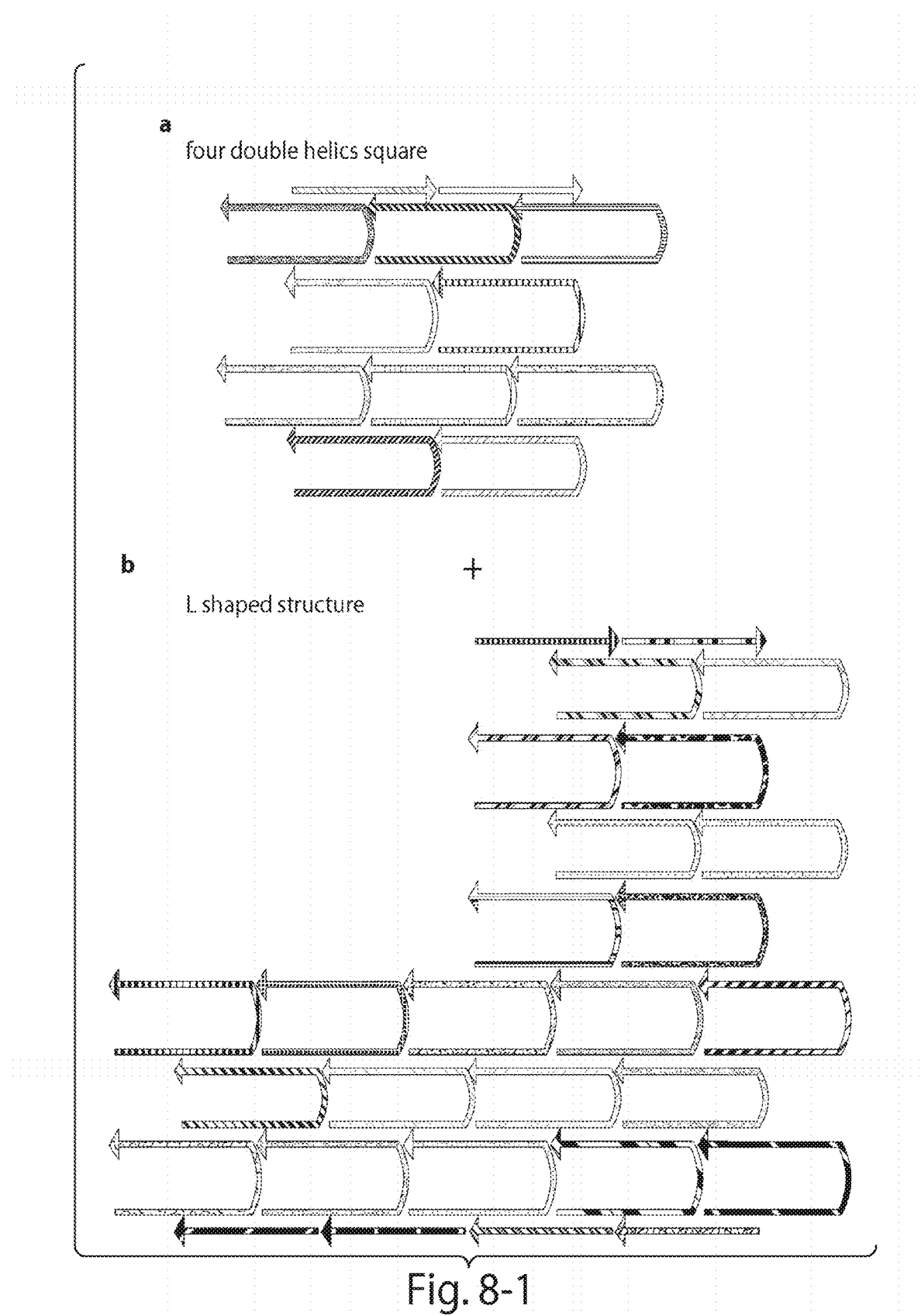
FIG. 8 is a schematic showing the annealing of a 4 parallel double helix square nucleic acid structure with an L-shaped nucleic acid structure. The Figure illustrates a modular approach to nucleic acid structure synthesis according to the invention.
Figures 2, 8:
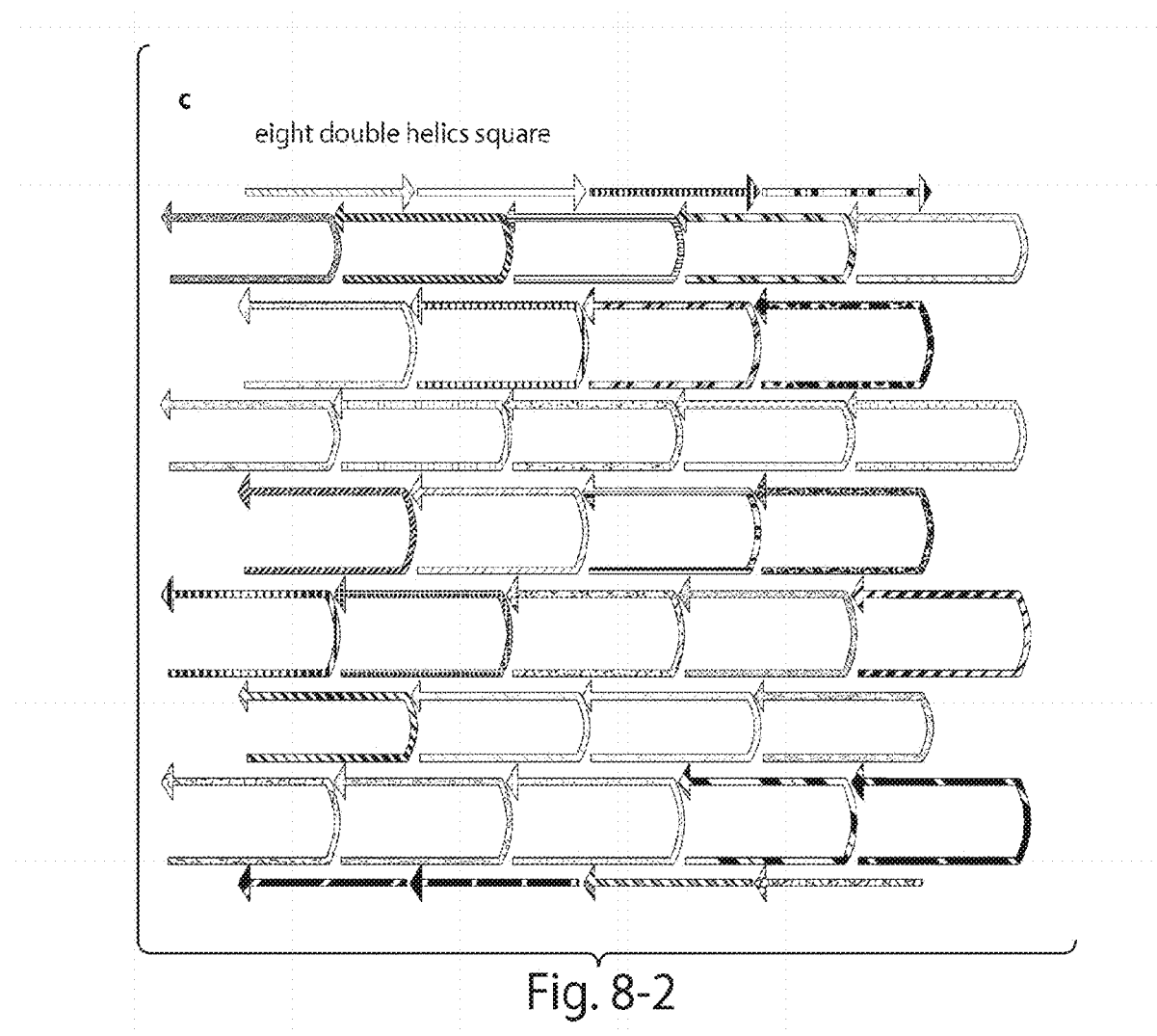

As discussed herein, nucleic acid structures may be synthesized by combining and annealing a plurality of single stranded oligonucleotides in a single annealing reaction to yield a nucleic acid structure of desired shape, size, complexity and modification. The invention also contemplates synthesis of nucleic acid structures by annealing separate smaller nucleic acid structures to each other, in a modular manner. This approach is illustrated in FIG. 8 in which a 4 double helix square structure and an L-shaped structure are made separately and then combined and annealed to each other to form an 8 double helix square. Accordingly, the structure of the invention may be made from annealing oligonucleotides to each other as illustrated in FIG. 4, and/or by annealing smaller structures to each other as illustrated in FIG. 8. This approach has been used to fuse together lattice-shaped structures to each other and tube-shaped structures to each other. Such fusion may also occur without the need to purify the structures from their initial synthesis annealing reaction solution. Thus, whether purified or not, the structures may be combined and annealed.

In some embodiments, the structures are annealed by subjecting them to an elevated temperature and then a slow cooling process. The elevated temperature may be about 50° C., about 45° C., or about 40° C., and the cooling process is intended to cool the solution to about room temperature (e.g., about 25° C.). The cooling period may be several hours including 2, 3, 4, 5, 6, 7, 8, 9, or 10 hours or more. Alternatively, the nucleic acid structures may be combined and allowed to anneal at a single temperature, including for example room temperature for the same length of time.

In other embodiments, the invention contemplates staggered or sequential addition (and annealing) of structures, as compared to simultaneous mixture and annealing of all structures. Sequential addition may be particularly useful in the synthesis of more complex structures. In some instances, these and other annealing methods can be carried out either in a static environment or under flow. A flow environment allows non-annealed oligonucleotides or nucleic structures to be removed prior to the addition of subsequent components.

The invention also provides pluralities of nucleic acid structures. As used herein, the term plurality intends more than one, and may be used interchangeably with the term population. Such pluralities may comprise 10, 50, 100, 500, 1000 or more structures. Such pluralities may have varying degrees of homogeneity intending that a percentage of the nucleic acid structures in the plurality are identical to each other with respect to size, shape, complexity and/or modification. The plurality of structures therefore may be at least 20%, 30%, 40%, 50%, 60%, 70%, 80%, 90%, or 100% homogeneous in structures having a certain characteristic. As an example, a plurality of lattice shaped structures may be at least 50% homogeneous intending that at least 50% of the structures in that plurality are lattice shaped.

Figure 12:
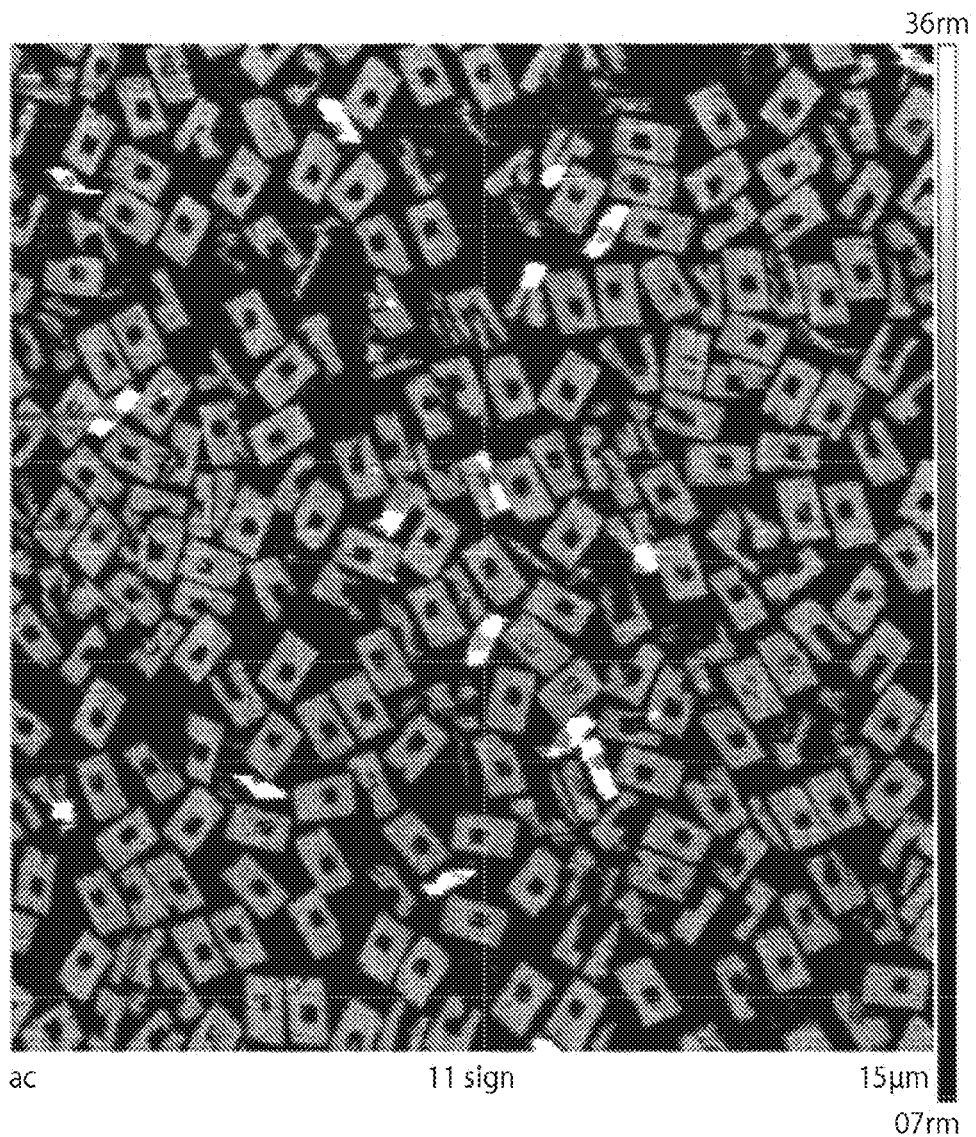
FIG. 12 is an AFM image of a plurality of rectangular, internal-ring shaped structures.

Such pluralities may be monodisperse intending that their members may be identical in terms of one or more characteristics including size, shape, complexity and/or modification. The pluralities may be monodisperse for all of these characteristics. In some embodiments, the pluralities are substantially monodisperse. Substantially monodisperse refers to pluralities in which at least 50%, 60%, 70%, 80%, 90%, or more of the structures are of about the same shape, size, complexity and/or have the same modification. In some embodiments, at least 10%, 20%, 30%, 40% or more of the structures are of about the same shape, size, complexity and/or have the same modification. An exemplary plurality is shown in FIG. 12.

The degree of homogeneity (and conversely heterogeneity) in a plurality may be determined using a number of techniques, including but not limited to AFM or TEM, and gel electrophoresis. These techniques have been used to determine the degree of homogeneity in prepared populations of structures, as discussed in the Examples. Importantly, it has been found that the annealing methods provided herein reproducibly yield populations having a predominant nucleic acid structure species. Moreover, that predominant species appears identical to the species that was intended using the design and mapping approach of the invention.

As illustrated in a number of the Figures, in some instances, once a nucleic acid structure is formed, there may still be domains that are single stranded. These may exist, for example, at the borders. Such borders are represented by the left and right borders of the structures provided in the Figures. It has been found in accordance with the invention that the nature of such domains can impact the efficiency and yield of the annealing process. More specifically, if these single stranded regions are of a mixed nucleotide sequence, then the structures are more likely to agglomerate and yield is reduced. Such agglomeration can be reduced by manipulating the nucleotide sequence of these single stranded regions. Specifically, single stranded regions that are poly T in sequence are less likely to cause agglomeration, resulting in better yields of structures. These poly T domains are shown, for example, in FIGS. 3B-F, represented as T10 or T11 to indicate the number of thymidines in the domain. Poly A and poly C sequences may also be used. In some embodiments, therefore, certain single stranded domains may be present in a structure and such domains may be identical to each other in sequence.

In certain embodiments, border regions may be comprised of a mixture of poly T domains and other domains of mixed sequence, provided that the structures do not agglomerate substantially. In these instances, the mixed sequence domains can be used to anneal two or more structures to each other, for example as shown in FIG. 8. The number of such domains may be 6, 8, 10 or more.

The structures of the invention may be modified during synthesis or post-synthesis. They may be modified during synthesis by using oligonucleotides that are modified. For example, one or more oligonucleotides used to generate a structure may be conjugated to a moiety of interest. Modified oligonucleotides may be used to generate the structures of the invention provided such modifications do not interfere with the ability of the oligonucleotide to bind to other oligonucleotides as required in order to form the desired structure. Additionally or alternatively, the structure may be modified post-synthesis.

Any modification is contemplated provided it does not interfere with the annealing of oligonucleotides to each other and it does not render the structure less stable, unless that is otherwise intended by the modification. Modification may be but is not limited to chemical or enzymatic in nature. Modification may involve the use of nucleic acid conjugated moieties. The moieties may be, without limitation, metallic, organic and inorganic in nature. The moieties may be conjugated to nucleic acids that are able to recognize and bind to oligonucleotides in the structure. Such nucleic acids may be triplex forming oligonucleotides, as an example. In other instances, one or more non-nucleic acid moieties may be attached, permanently or transiently, covalently or non-covalently, to the structures. The invention contemplates that unique and/or non-unique oligonucleotides may be modified. The oligonucleotides in a structure may themselves be conjugated to one or more domains that do not contribute to the structure but rather are used to bind moieties to the structure. It is to be understood that, since the location of each oligonucleotide and each domain in the structure can be predetermined, the location of each modification to the ultimate resulting structure can also be predetermined. In other words, knowledge of the location of each oligonucleotide in the structure facilitates the addressability of the structure.

Single Stranded Oligonucleotides:

The nucleic acid structures of the invention are designed and made using a plurality of single stranded oligonucleotides that anneal to each other in a sequence-specific manner. The oligonucleotides may be characterized by their length, their sequence, and their domain composition. The number and sequence of their domains governs the binding activity and location of each oligonucleotide. Their domain number typically governs the number of oligonucleotides each oligonucleotide will bind to in a structure.

In some instances, the oligonucleotides used to make a structure comprise an even number of domains. Each oligonucleotide typically comprises at least two domains. In some embodiments, oligonucleotides used to make a structure may be 2- and 4-domain oligonucleotides. It is also possible to form structures using other combinations of oligonucleotides including without limitation 2- and 6-domain oligonucleotides, 3- and 6-domain oligonucleotides, 2- and 8-domain oligonucleotides, 4- and 8-domain oligonucleotides, and the like.

A domain, as used herein, refers to a nucleotide sequence (i.e., a number of contiguous nucleotides or nucleotide analogs having the ability to bind in a sequence-specific manner to their complements). The domains in a plurality of oligonucleotides or in a nucleic acid structure are designed such that they anneal to domain in another oligonucleotide. The collective complementarity of all domains of an oligonucleotide facilitates the self-assembly of such oligonucleotides to form nucleic acid structures.

The domain length may vary. The combined length of two contiguous domains that contribute to the same helix will typically have a length that is h×k where h represents the number of monomer units (such as for example nucleotides) required to make a full helical turn and k represents any integer of 1 or greater. As an example, for B form DNA there are typically 10.5 nucleotides per helical turn, while for RNA there are 11 nucleotides per helical turn. Thus, for domains that are B form DNA in nature, the combined length of two contiguous domains that contribute to the same helix can be represented as 10.5*k (rounding off to the nearest integer) where k represents an integer of 1 or greater, wherein * denotes a multiplication sign.

In situations where two contiguous domains from the same oligonucleotide are contributing to the same helix, the lengths of the two domains will be interrelated. Assume that the combined length of two such domains is x where x is h*k as defined above. In that case, one domain has a length of y and the other domain has a length of x−y, provided that y is 1 or greater. As an example, in one embodiment, each of a first and a second DNA domain may range in length from 1-20 nucleotides provided that the combined length of the two domains is 21 nucleotides.

In some embodiments, two contiguous domains that contribute to the same helix may have a combined length of about 21+/−2 nucleotides in length, or any integral multiple of 10.5 nucleotides. Thus, a single domain may have a length of, for example, 1, 2, 3, 4, 5, 6, 7, 8, 9, 10, 11, 12, 13, 14, 15, 16, 17, 18, 19, 20, 21 or 22 nucleotides. Two contiguous domains may have a total combined length of, for example, 19, 20, 21, 22 or 23 nucleotides. A 2-domain oligonucleotide may have a length of, for example, 21+/−2 nucleotides. A 4-domain oligonucleotide may have a length of, for example, 42+/−4 nucleotides.

Thus in general, two consecutive domains participating in the same duplex with a total length x=h*k as defined above, x can be h*k+/−a, where a=0, 1, 2, . . . , y, where y=(h/2)*k (rounding to the nearest integer). For example, in one embodiment, h=11 (in the case of RNA), k=1, and y=6. Hence, x can be 11+/−0, 1, 2, 3, 4, 5, or 6. As another example, for h=10.5 (in the case of B form DNA), k=2, y=10. Hence x can be 21+/−1, 2, 3, 4, 5, 6, 7, 8, 9, or 10.

In some important embodiments, a domain has a length of 10 or 11 nucleotides, two contiguous domains have a length of 21 nucleotides, and a 4-domain oligonucleotide has a length of 42 nucleotides. It is to be understood that the invention contemplates oligonucleotides having two contiguous domains (both contributing to a single helix) that have a length that is a multiple of 21 nucleotides.

Domain length combinations such as 10-11-11-10, 11-10-10-11, 11-10-11-10, and 10-11-10-11, where the first number represents the length of the first domain, the second number represents the length of the second domain, the third number presents the length of the third domain, and the fourth number represents the length of the fourth domain, and where the four domains are arranged as in FIG. 1, are contemplated by the invention.

Typically in a given synthesis method or resultant structure, oligonucleotides having the same number of domains will also have the same length. As an example, in one embodiment, all 4-domain oligonucleotides will be the same length and all 2-domain oligonucleotides will be the same length (but that length will be different from that of the 4-domain oligonucleotides). More specifically, some embodiments will use 4-domain oligonucleotides that are one length (e.g., n nucleotides) and 2-domain oligonucleotides that are half that length (e.g., n/2 nucleotides).

The 4-domain "internal" oligonucleotides represent the monomer units for the structures of the invention. As a stand-alone monomer, the 4-domain oligonucleotide has no well-defined structure. However, upon interaction with neighboring 2- and/or 4-domain oligonucleotides, it folds into a tile-like shape. This is contrasted with previous tile monomers which, as stand-alones, fold into multistranded structures having a defined, structurally rigid (or semi-rigid) body and several sticky ends.

The invention contemplates nucleic acid structures comprising any number of single stranded oligonucleotides. As an example, the nucleic acid structures may comprise as few as 4 and as many as 1000 (or more) oligonucleotides, without limitation. Similarly, pluralities of oligonucleotides used to generate nucleic acid structures may comprise as few as 4 different types of oligonucleotides (as defined by nucleotide sequence) and as many as 1000 (or more) different oligonucleotide species (as defined by nucleotide sequence), without limitation. Thus, depending on the embodiment, the nucleic acid structure may comprise 4, 5, 6, 7, 8, 9, 10, 15, 10, 25, 50, 75, 100, 150, 200, 250, 300, 350, 400, 450, 500, 600, 700, 800, 900, 1000, 1100, 1200, 1300, 1400, 1500, or more oligonucleotides. Similarly, depending on the embodiment, a plurality of oligonucleotides used to generate nucleic acid structures may comprise 4, 5, 6, 7, 8, 9, 10, 15, 10, 25, 50, 75, 100, 150, 200, 250, 300, 350, 400, 450, 500, 600, 700, 800, 900, 1000, 1100, 1200, 1300, 1400, 1500, or more different oligonucleotides.

Oligonucleotides, in the context of the invention, include DNA such as D-form DNA and L-form DNA and RNA, as well as various modifications thereof. Modifications include base modifications, sugar modifications, and backbone modifications. Non-limiting examples of these are provided below.

Non-limiting examples of DNA variants that may be used in the invention are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that the oligonucleotides used in products and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The oligonucleotide modification may render the oligonucleotide more stable and/or less susceptible to degradation under certain conditions. For example, in some instances, the oligonucleotides are nuclease-resistant.

The oligonucleotides may have a homogenous backbone (e.g., entirely phosphodiester or entirely phosphorothioate) or a heterogeneous (or chimeric) backbone. Phosphorothioate backbone modifications render an oligonucleotide less susceptible to nucleases and thus more stable (as compared to a native phosphodiester backbone nucleic acid) under certain conditions. Other linkages that may provide more stability to an oligonucleotide include without limitation phosphorodithioate linkages, methylphosphonate linkages, methylphosphorothioate linkages, boranophosphonate linkages, peptide linkages, alkyl linkages, dephospho type linkages, and the like. Thus, in some instances, the oligonucleotides have non-naturally occurring backbones.

Oligonucleotides may be synthesized in vitro. Methods for synthesizing nucleic acids, including automated nucleic acid synthesis, are also known in the art. Oligonucleotides having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" IRL Press, Oxford, UK, 1991, and M. D. Matteucci and M. H. Caruthers, *Tetrahedron Lett.* 21, 719 (1980)) Aryl- and alkyl-phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

The oligonucleotides may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$) alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

The oligonucleotides may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Methods of Synthesis:

The invention contemplates synthesizing nucleic acid structures through annealing processes. In one approach, once the single stranded oligonucleotides have been identified and synthesized (e.g., using commercial vendors such as Bioneer), they are combined, in a single vessel such as but not limited to a tube, a well, a vial, and the like. The molar amounts of oligonucleotides that are used will depend on the frequency of each oligonucleotide in the structures desired and the amount of structures desired. In some embodiments, the oligonucleotides may be present in equimolar concentrations. In some embodiments, each oligonucleotide may be present at a concentration of about 100 nM. The oligonucleotides are placed in a solution. Preferably the solution is buffered although the annealing reaction can also occur in the absence of buffer. The solution may further comprise divalent cations such as but not limited to $Mg^{2+}$. The cation or salt concentration may vary. An exemplary concentration is about 25 mM. The solution may also comprise EDTA or other nuclease inhibitors in order to prevent degradation of the oligonucleotides.

The annealing reaction is carried out by heating the solution and then allowing the solution to slowly cool down. The temperature of the reaction should be sufficiently high to melt any undesirable secondary structure such as hairpin structures and to ensure that the oligonucleotide species are not bound incorrectly to other non-complementary oligonucleotides. The temperature may therefore be initially raised to about 100° C., about 95° C., about 90° C., about 85° C., 80° C., 75° C., 70° C., 65° C. or 60° C. in some embodiments. The temperature may be raised by placing the vessel in a hot water bath or a heating block or a device capable of temperature control such as a PCR machine. The vessel may be kept in that environment for seconds or minutes. Typically, an incubation of about 1-10 minutes is sufficient.

Once the incubation at elevated temperature is complete, the temperature may be dropped in a number of ways. The temperature may be dropped in an automated manner using a computer algorithm that drops the temperature by a certain amount and maintains that temperature for a certain period of time before dropping the temperature again. Such automated methods may involve dropping the temperature by a degree in each step or by a number of degrees at each step. The vessel may thus be heated and cooled in the same device.

An exemplary process is provided. To effect a drop in temperature from about 90° C. to about 25° C., the temperature is changed from 90° C. to 61° C. in one degree increments at a rate of 10 minutes per degree (i.e., 90° C. for 10 minutes, 89° C. for 10 minutes, etc.). The temperature is then changed from 60° C. to 25° C. in one degree increments and at a rate of about 20 minutes per degree (i.e., 60° C. for 20 minutes, 59° C. for 20 minutes, etc.). The total annealing time for this process is about 17 hours. In accordance with the invention, under these conditions, the oligonucleotides self-assemble into a nucleic acid structure of predetermined and desired shape and size.

Alternatively, the vessel may be placed in a different environment, including for example a room temperature environment (e.g., about 25° C.). It is maintained there for an extended period of time in order to allow the oligonucleotides to anneal to each other in the predetermined manner. The cooling down period may last for hours, including without limitation 10, 11, 12, 13, 14, 15, 16, 17, 18, 19 or 20 or more hours. In some instances, the cooling down period is longer than 20 hours and may be 25, 30, 25, 40, 50, 55, 60, or more hours.

The Examples describe a specific annealing process using 100 nM oligonucleotides in a Tris-EDTA (TE), 25 mM $MgCl_2$ solution and heating the solution to about 90° C. and then cooling the solution to about 25° C. over a period of about 17 hours, as described above with a 10 minute per degree drop between 90° C. and 61° C. and a 10 minute per degree drop between 60° C. and 25° C.

Still another set of conditions for self-annealing includes a TE/$Mg^{2+}$ buffer (20 mM Tris, pH 7.6, 2 mM EDTA, 12.5 mM $MgCl_2$) and an identical temperature reduction process.

The stoichiometry of oligonucleotides does not have to be tightly regulated.

Following the annealing process, the reaction mixture may be used directly or it may be further fractionated in order to further isolate the nucleic acid structure products. As an example, the reaction mixture may be subjected to gel electrophoresis, such as 2% native agarose gel electrophoresis, in order to physically separate the structure of interest from other structures or substrates. Typically, a single dominant band is observed. The band may be extracted from the gel and further purified, for example, via centrifugation. The purified product may then be again subjected to gel electrophoresis, with a single band again expected. The purified product may be imaged via AFM or TEM. Such imaging reveals the dimensions of the purified product, the degree and location of any modification (e.g., streptavidin modification), and can be used to determine yield and degree of purity. Such analyses have revealed the formation of structures having approximately expected dimensions.

Yield of desired product may also be determined post-annealing. "Assembly yield" may be first estimated by native gel electrophoresis, in which the samples are stained with SYBR safe. The yield (referred to as "gel yield") is calculated as the ratio between the fluorescent intensity of the desired product band and that of the entire lane (after background correction). The ratio will therefore be an indicator of the yield. Measured gel yields range from 6-40%. It has been found according to the invention that such ratios may be overestimates since there is apparent structure and sequence-dependent variation in the staining efficiency of SYBR safe. In some instances, the yields may be about 60-100% of the measured gel yield.

The efficiency of the annealing process may also be determined by measuring the fraction of "well-formed" structures as a percentage of all identifiable shapes in an AFM field. The structure is considered to be "well-formed" if it has no defects in its expected outline greater than 15 nm in diameter and no defects in its interior greater than 10 nm in diameter. Following the above criteria, "well-formed" ratios, or "AFM yields" ranging from about 20-85% have been observed across a spectrum of structures. In certain instances, this ratio is likely an underestimate of the actual ratio of "well-formed" structures within the purified product, due to the relative fragility of the structure in some instances and the significant post-purification damage that likely occurs during sample deposition or imaging. Such fragility may be mitigated by introducing more covalent bonds into the assembled structures, e.g. via ligation of two ends of an 4-oligonucleotide SST or crosslinking of neighboring 4-oligonucleotide SSTs.

For some structures having depth (e.g., tubes or barrels), the degree of well-formed structures may be determined using TEM imaging. In those instances, the TEM yield was defined as the percentage of identifiable structures (e.g., tubes or barrels) that measure within 5 nm deviation from the expected full length (e.g., tube or barrel length), based on a 3.5 nm per helical turn estimation.

The invention contemplates manual or automatic means for synthesizing the structures of the invention. An example of an automatic means, a computer program (e.g., a MAT-LAB program) provides a graphical interface that displays the canvas from which a structure will be made (e.g., in the case of the 310-oligonucleotide pool, a rectangular canvas is the starting point). Onto that canvas is mapped the desired structure, and the pixels (or SSTs) necessary to synthesize that structure are identified. The program can also help to automate the process of strand picking and mixing using a liquid handling robot (Bravo, Agilent). Thus, once the end user maps the structure to the graphical interface, the computer program outputs instructions for a robotic liquid handler to pick and mix the suitable strands for subsequent annealing. The strand mixture is then used in standard one-pot annealing to produce the shape for AFM imaging. In various tests, each robot batch has been found to produce 48 shapes in roughly 48 hours, effectively reducing several human-hours of labor to 1 machine-hour per shape, and avoids potential human mistakes. Such a robotic system was used to generate 44 of the shapes described herein.

The program interface features three functions: (1) shape design, (2) pipette sequence generation, and (3) protocol output. Using the program, three steps are involved in designing a target shape and generating the preannealing strand mixture for the shape. First, the program displays a schematic of the 2D lattice (the "molecular canvas") and allows the user to either draw a shape from scratch, or upload an image and convert it to a target shape. Then, a list of the constituent strands is generated for the shape. Based on the source strand arrangement in the 96 well plates used by the robot, this strand list is subsequently converted to a list of pipette sequences. Finally, a set of instructions (a runset) are generated in xml format and can be directly loaded and executed by the robot controlling software (VWorks, Agilent).

Figure 9:
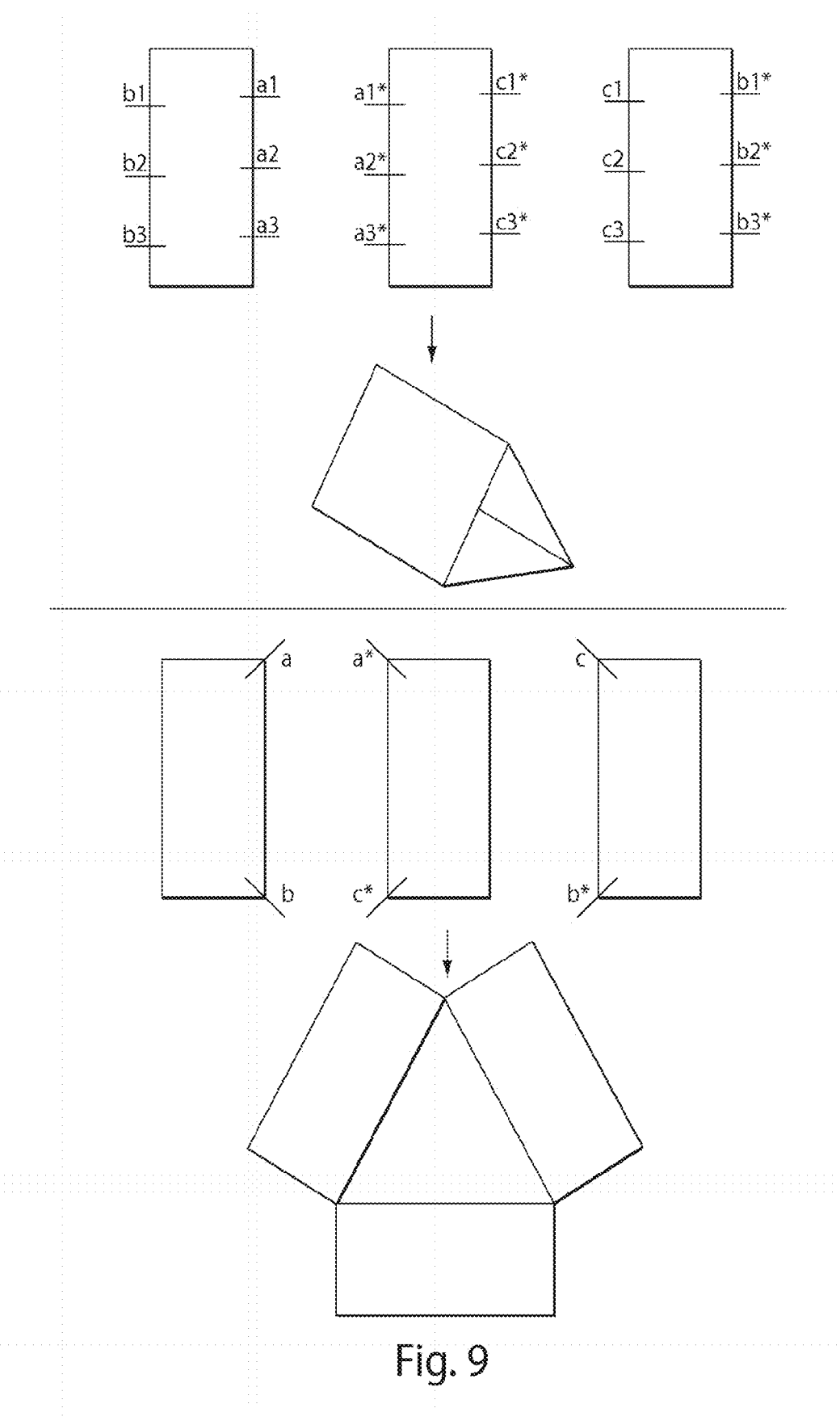
FIG. 9 is a schematic showing the attachment of three rectangular nucleic acid structures to each other using spacer-linkers. A variety of these composite structures may be made depending on the placement and length of the spacer-linkers.

Composite Structures:

The invention further contemplates that the nucleic acid structures described herein themselves may be used essentially as monomers or building blocks in order to form higher order or composite structures. The composite structures of the invention are comprised of nucleic acid structures linked to each other using spacer-linkers. The linkers are typically not integral to the nucleic acid structures although they may be attached to the structures via suitable functional groups. The ability to attach two or more nucleic acid structures together allows structures of greater size and complexity to be made. Examples of such structures and arrangements are shown in FIG. 9.

The dimensions of these composite structures may range from 500 nm to 100 microns, or 1-1000 microns, without limitation.

Applications:

The nucleic acid structures of the invention may be used in a variety of applications, including those that would benefit from the ability to precisely position and importantly arrange one or more moieties at a nanometer or micron scale.

As an example, the structures can be used as templates for arranging or patterning inorganic materials such as those useful in electronics, plasmonics, and quantum computing applications. Moieties that may be attached to the nucleic acid structures include metallic particles such as gold nanoparticles (refs. 5, 35), quantum dots (ref. 6), carbon nanotubes (ref. 7), and the like. In this way, the nucleic acid structures provided by the invention act as scaffolds upon which other moieties may be arranged and/or other structures may be synthesized with nanometer precision and control. For example, carbon nanotubes can be organized into functional molecular electronics systems; tunable geometric arrangement of gold nanoparticles can be used to make functional molecular electronics circuits and novel plasmonics circuits; organized, predetermined arrangement of magnetic particles can be used to make nano-inductors or memory devices; and organized and predetermined arrangement of quantum dots can be used to make novel quantum computers.

In other aspects, the invention contemplates that the nucleic acid structures of the invention may be metalized to make components for electronics. DNA tubes have been metalized into nanowires (refs. 4,15,19). Controlled metallization of the nucleic acid structures of the invention can be used to make, among other things, nano-wires with controlled diameters and hence controlled electronic properties. Further, novel molecular electronic components and circuits can be made through controlled metallization of the strut based nucleic acid structures provided by the invention.

The nucleic acid structures can also be used as templates for biological or organic molecules. Such templated molecules and systems may be useful, for example, in diagnostic and research applications. The biological or organic molecules include without limitation proteins and peptides such as antibodies and antibody fragments, enzymes and enzyme domains, receptors and receptor domains, biological ligands such as hormones and other signaling moieties, polysaccharides, cells, cell aggregates, and the like. Diverse strategies have been demonstrated for templating proteins on DNA lattices (refs. 4, 23, 36). Organization of proteins into prescribed geometric patterns with programmable nanometer precision can be used, for example, to study the cooperative behavior of biological motor proteins (ref. 37). Certain nucleic acid structures may also be used in cell or tissue culture. In these embodiments, as an example, the structures may be functionalized with biological moieties such as growth factors and extracellular matrix components. In this way, the functionalized structures may be arranged in culture to mimic a two or three dimensional in vivo environment. As a further example, it is contemplated that higher order functionalize structures may be made that exhibit a concentration gradient for any particular biological moiety. These systems can then be used to study cellular development, differentiation and/or motion for any number of cell types. In still other instances, higher order structures of the invention can be used as scaffolds for cellular growth and differentiation in vitro or in vivo.

In various of these applications, the invention further contemplates that the nucleic acid scaffold comprised of the structures of the invention may be retained or it may be removed (e.g., through digestion or degradation) once it ceased being a template. For example, if the goal is to create a predetermined arrangement of gold particles and such particles are connect to each other as desired independently of the nucleic acid scaffold, the scaffold may be removed, leaving only the gold nanoparticle network.

The following Examples are included for purposes of illustration and are not intended to limit the scope of the invention.

EXAMPLES

Example 1

Materials and Methods

Sample preparation. DNA strands were synthesized by Integrated DNA Technology, Inc. or Bioneer Corporation. To assemble the structures, DNA strands were mixed to a roughly equal molar final concentration of 100 nM per strand species for most of the structures (except for different shapes based on a 24H×28T rectangle, which were prepared in 200 nM) in 0.5×TE buffer (5 mM Tris, pH 7.9, 1 mM EDTA) supplemented with 12.5 or 25 mM $MgCl_2$. The concentrations were based on the manufacturer spec sheet, and no additional in-house calibration was performed. Thus, the stoichiometry for the strands was not tightly controlled. The mixture was then annealed in a PCR thermo cycler by cooling from 90° C. to 25° C. over a period of 17-58 hours with different cooling programs. The annealed samples were then applied to a 1.5 or 2 percent agarose gel electrophoresis (gel prepared in 0.5×TBE buffer supplemented with 10 mM $MgCl_2$ and pre-stained with SYBR safe) in an ice water bath. Then, the target gel bands were excised and put into a Freeze 'N Squeeze column (Bio-Rad Laboratories, Inc.). The gel pieces were crushed into fine pieces by a microtube pestle in the column and the column was then directly subjected to centrifugation at 438 g for 3 minutes. Samples centrifuged through the column were collected for concentration estimation by the measurement of ultraviolet absorption at 260 nm. Such estimation will be useful for estimating the dilution factor before AFM or TEM imaging.

Streptavidin labeling. Streptavidin labelings were done with two different approaches. 1) Labeling the top and bottom row or internal loci of a 24H×28T rectangle. Each tile of the top and bottom rows (or internal loci) of the 24H×28T rectangle was modified to have a 3' 17 nt handle (TT as spacer and GGAAGGGATGGAGGA, SEQ ID NO: 363 to be complementary to the 3' biotin modified strand whose sequence is TCCTCCATCCCTTCC-biotin, SEQ ID NO. 364). Special tiles of the top and bottom rows (or internal loci), and the rest of the component tiles of the rectangular lattice were mixed with 30 biotin modified strands of 1-2× concentration (when concentration of special and common component tiles was 100 nM and there were 14 different special tile species, 1× concentration of the 3' biotin modified strand was 100×14=1400 nM), which is complementary to the handle sequence of the special tiles, in 0.5×TE buffer (25 mM $MgCl_2$). They were then annealed over 17 hours and purified after agarose gel electrophoresis. The purified sample was then subjected to AFM imaging. After the first round of imaging, streptavidin (1 µL of 10 mg/mL in 0.5×TE buffer (10 mM $MgCl_2$)) was added to the imaging sample (~40 µL) for an incubation of 2 minutes before re-imaging. 2) Labeling the poly-T ends of tube structures. After tube purification, 3' biotin modified poly-A strand (5-10× to the poly-T counterparts) was mixed with the sample at room temperature overnight. The sample was then subjected to AFM imaging. After the first round of imaging, streptavidin (1 µL of 10 mg/mL in 0.5×TE buffer (10 mM $MgCl_2$)) was added to the imaging sample on mica for an incubation of 2 minutes before re-imaging.

Robot automation for sample preparation. A MATLAB program was designed to aid complex shapes design and automate strand mixing by a liquid handling robot (Bravo, Agilent). For each shape, 5 µL of 10 µM of each single strand tile in water solution was picked and mixed into a final volume of less than 2 mL (the exact volume was determined by the number of constituent strands for the target shape), and was then vacuum evaporated to a 200 µL of 250 nM solution. This mixture was then supplemented with 50 µL 62.5 mM $Mg^{2+}$ buffer to reach a 250 µL final mixture ready for annealing. This preannealing solution had the following final concentrations: 200 nM DNA strand per SST species and 12.5 mM $Mg^{2+}$. Each run accommodated 48 shapes and took around two days to finish.

AFM imaging. AFM images were obtained using an SPM Multimode with Digital Instruments Nanoscope V controller (Vecco). A 5 µL drop (2-5 nM) of annealed sample with purification followed by a 40 µL drop of 0.5×TE (10 mM $MgCl_2$) was applied onto the surface of a freshly cleaved mica and left for approximately 2 minutes. Sometimes, additional dilution of the sample was performed to achieve the desired sample density. On a few occasions, supplemental 10 mM $NiCl_2$ was added to increase the strength of DNA-mica binding. Samples were imaged using the liquid tapping mode. The AFM tips used were the short and thin cantilevers in the SNL-10 silicon nitride cantilever chip (Vecco Probes).

TEM imaging. For imaging, 3.5 µL sample (1-5 nM) were adsorbed onto glow discharged carbon-coated TEM grids for 4 minutes and then stained using a 2% aqueous uranyl formate solution containing 25 mM NaOH for 1 minute. Imaging was performed using a JEOL JEM-1400 operated at 80 kV.

Yield quantification with SYBR safe staining. Yield was first estimated by native agarose gel electrophoresis analysis. The ratio between the fluorescence intensity of the target band and that of the entire lane was adopted to present the gross yield of structural formation. For a 24H×28T rectangle, as an independent alternative quantification procedure, the intensity of the target band was compared with a standard sample (1500 by DNA of 1 kb ladder mixture). The mass value of the target band was deducted from the intensity-mass curve based on the standard sample, and was used to calculate the yield of the desired structure.

Measurement and statistics. AFM measurements were obtained using Nanoscope Analysis (version 1.20) provided by Veeco. The cross section function was applied for the distance measurement task (lengths and widths of the rectangles of different sizes). "Well-formed" structures were chosen for the measurements. TEM images of the tubes were analyzed using ImageJ (version 1.43u) by NIH. The "Straight Line" function was applied in order to measure the width of a tube. The "Segmented Line" function was applied to highlight and measure the contour length of a tube. Thirty sample points were collected for each distance measurement (e.g. width of a 24H×28T rectangle) and the statistics (e.g. average, standard deviation) were based on the 30 data points.

Example 2

Using the methods described herein, we have used a plurality of single stranded oligonucleotides to build DNA structures as large as those made from the prior art DNA origami approach. More specifically, we have self-assembled 362 different single stranded DNAs to build a rectangular lattice that is about 60 nm by about 100 nm is size, and derivative structures thereof.

The oligonucleotides were synthesized (e.g., Bioneer) and mixed together in the desired concentration (e.g., 100 nM) in TE buffered solution with $MgCl_2$ (concentration 25 mM). The mixture was subjected to an annealing procedure involving a slow cooling down (e.g., starting at about 90° C. and ending at about 25° C. over the course of 17 hours, as described herein). This annealing procedure allowed the oligonucleotides to self-assemble, thereby forming the nucleic acid structures.

Once the annealing was complete, the reaction mixtures were analyzed prior to and following purification of the structures. The structures were characterized using agarose gel electrophoresis, AFM and TEM.

The structures that have been made using this approach include those shown in FIGS. 3B-F, 5B-D, and 10A (using the oligonucleotides shown in the Figures with reference to Table 1, below). The structures shown in FIGS. 4 and 5 have also been made using this approach.

Example 3

We then also attempted to connect two nucleic acid structures, each a tube shape, to form a larger, higher order structure.

First, each of the tubular structures were made by mixing and annealing oligonucleotides as described herein. The oligonucleotides were combined and annealed using a temperature transition of from about 90° C. to about 25° C. over the course of about 17 hours. The resultant nucleic acid structures were then mixed together and further annealed using a temperature transition of from about 45° C. to about 25° C. over the course of about 7 hours. This process provided an improved yield as compared to simply maintaining the structures at room temperature for the same period of time. In addition, it was noted that the structures could be adequately annealed regardless of whether they were purified after the first annealing step.

TABLE 1

Single Stranded Oligonucleotides

| SEQ ID NO. | strand name | segment composition | segment sequences |
|---|---|---|---|
| 1 | 1.1 | a1.1-b1.1 | CAGGGTGGTAC-TATTTATCGT |
| 2 | 1.2 | a1.2-b1.2 | CCTCCGGGCAC-TCAGCTTACT |
| 3 | 1.3 | a1.3-b1.3 | CAACCGATCTC-TGGATAATAT |
| 4 | 1.4 | a1.4-b1.4 | CCCGTCAAAGC-TTATATTTCT |
| 5 | 1.5 | a1.5-b1.5 | CTATTTAGAAC-TCCAGGAAGT |
| 6 | 1.6 | a1.6-b1.6 | CCAGGCCCACC-TATATGGATT |
| 7 | 1.7 | a1.7-b1.7 | CTTAAAGGCTC-TGGTTGAAGT |
| 8 | 1.8 | a1.8-b1.8 | CAGATCACGAC-TAACACACCT |
| 9 | 1.9 | a1.9-b1.9 | CGCCTCTATCC-TGTGAACACT |
| 10 | 1.10 | a1.10-b1.10 | CGGCTGAGAAC-TTAAGTTTCT |
| 11 | 1.11 | a1.11-b1.11 | CGGTCTCGCCC-TTAGAATGAT |
| 12 | 1.12 | a1.12-b1.12 | CGGGCGCCAAC-TGAAGCCCTT |
| 13 | 1.13 | a1.13-b1.13 | CGGGACATCCC-TTTAGTCGAT |
| 14 | 1.14 | a1.14-b1.14 | CGGAGATGCGC-TCAGATGTAT |
| 15 | 2.1 | 10T-b2.1-a1.1*-10T | TTTTTTTTTT-TGGGTGCCCAT-GTACCACCCTG-TTTTTTTTTT |
| 16 | 2.2 | a2.2-b2.2-a1.2*-b1.1* | CGGGCTGGTC-TCCGAAGGACT-GTGCCCGGAGG-ACGATAAATA |
| 17 | 2.3 | a2.3-b2.3-a1.3*-b1.2* | CGAAGTTTCC-TGCATTATGAT-GAGATCGGTTG-AGTAAGCTGA |
| 18 | 2.4 | a2.4-b2.4-a1.4*-b1.3* | CTTCAAGTGC-TCCCTGCAGCT-GCTTTGACGGG-ATATTATCCA |
| 19 | 2.5 | a2.5-b2.5-a1.5*-b1.4* | CGATTTCAGC-TAAAGTTGTGT-GTTCTAAATAG-AGAAATATAA |
| 20 | 2.6 | a2.6-b2.6-a1.6*-b1.5* | CCAATGCGCC-TGCACCTGTAT-GGTGGGCCTGG-ACTTCCTGGA |
| 21 | 2.7 | a2.7-b2.7-a1.7*-b1.6* | CATCACATCC-TCGTTCGTACT-GAGCCTTTAAG-AATCCATATA |
| 22 | 2.8 | a2.8-b2.8-a1.8*-b1.7* | CACAGTCTGC-TACTGCAGATT-GTCGTGATCTG-ACTTCAACCA |
| 23 | 2.9 | a2.9-b2.9-a1.9*-b1.8* | CTTGGATACC-TCAGTCTGACT-GGATAGAGGCG-AGGTGTGTTA |
| 24 | 2.10 | a2.10-b2.10-a1.10*-b1.9* | CAACTCTAGC-TCCTCCGCACT-GTTCTCAGCCG-AGTGTTCACA |
| 25 | 2.11 | a2.11-b2.11-a1.11*-b1.10* | CTCACATAAC-TTCCCTCTTCT-GGGCGAGACCG-AGAAACTTAA |
| 26 | 2.12 | a2.12-b2.12-a1.12*-b1.11* | CTTGCGAGGC-TAAAGAATGCT-GTTGGCGCCCG-ATCATTCTAA |
| 27 | 2.13 | a2.13-b2.13-a1.13*-b1.12* | CAGCGGACTC-TAGTGGGCTAT-GGGATGTCCCG-AAGGGCTTCA |
| 28 | 2.14 | a2.14-b2.14-a1.14*-b1.13* | CATCGTGTGC-TTATTCCTCTT-GCGCATCTCCG-ATCGACTAAA |
| 29 | 2.15 | a2.15-11T-11T-b1.14* | CCTATTTGTC-TTTTTTTTTTT-TTTTTTTTTTT-ATACATCTGA |
| 30 | 3.1 | a3.1-b3.1-a2.2*-b2.1* | CGCCGCGTGTC-TATCGTGGTT-GACCAGCCCG-ATGGGCACCCA |

TABLE 1-continued

Single Stranded Oligonucleotides

| SEQ ID NO. | strand name | segment composition | segment sequences |
|---|---|---|---|
| 31 | 3.2 | a3.2-b3.2-a2.3*-b2.2* | CCATTAGGGCC-TAAGCAGCCT-GGAAACTTCG-AGTCCTTCGGA |
| 32 | 3.3 | a3.3-b3.3-a2.4*-b2.3* | CATATATCGAC-TCGTCAAGGT-GCACTTGAAG-ATCATAATGCA |
| 33 | 3.4 | a3.4-b3.4-a2.5*-b2.4* | CGAAAGTTGGC-TAAACGACAT-GCTGAAATCG-AGCTGCAGGGA |
| 34 | 3.5 | a3.5-b3.5-a2.6*-b2.5* | CATACGGTTTC-TAGAAAGATT-GGCGCATTGG-ACACAACTTTA |
| 35 | 3.6 | a3.6-b3.6-a2.7*-b2.6* | CAAGGCTCGGC-TTATGCAATT-GGATGTGATG-ATACAGGTGCA |
| 36 | 3.7 | a3.7-b3.7-a2.8*-b2.7* | CAACTTAGCTC-TGAAAGTCGT-GCAGACTGTG-AGTACGAACGA |
| 37 | 3.8 | a3.8-b3.8-a2.9*-b2.8* | CACTTCCCATC-TAAACCAGGT-GGTATCCAAG-AATCTGCAGTA |
| 38 | 3.9 | a3.9-b3.9-a2.10*-b2.9* | CAAGTCCGCGC-TCGTCAGATT-GCTAGAGTTG-AGTCAGACTGA |
| 39 | 3.10 | a3.10-b3.10-a2.11*-b2.10* | CGTGTAGAATC-TAGAGCTGAT-GTTATGTGAG-AGTGCGGAGGA |
| 40 | 3.11 | a3.11-b3.11-a2.12*-b2.11* | CAGCTGAGAGC-TTTGGTCGGT-GCCTCGCAAG-AGAAGAGGGAA |
| 41 | 3.12 | a3.12-b3.12-a2.13*-b2.12* | CATCTTAGGGC-TGCTGTGTAT-GAGTCCGCTG-AGCATTCTTTA |
| 42 | 3.13 | a3.13-b3.13-a2.14*-b2.13* | CCTTTCTCGAC-TCTGAAGTGT-GCACACGATG-ATAGCCCACTA |
| 43 | 3.14 | a3.14-b3.14-a2.15*-b2.14* | CGCCCTGTTTC-TGAGTCCCTT-GACAAATAGG-AAGAGGAATAA |
| 44 | 4.1 | 10T-b4.1-a3.1*-10T | TTTTTTTTTT-TGGGAGTGGAT-GACACGCGGCG-TTTTTTTTTT |
| 45 | 4.2 | a4.2-b4.2-a3.2*-b3.1* | CAGGCTCTAC-TGGGAGGATAT-GGCCCTAATGG-AACCACGATA |
| 46 | 4.3 | a4.3-b4.3-a3.3*-b3.2* | CGCGCTAGAC-TACATTTATAT-GTCGATATATG-AGGCTGCTTA |
| 47 | 4.4 | a4.4-b4.4-a3.4*-b3.3* | CTACGCTATC-TTTACCATTAT-GCCAACTTTCG-ACCTTGACGA |
| 48 | 4.5 | a4.5-b4.5-a3.5*-b3.4* | CGGAGTAAAC-TTGTGCCTTGT-GAAACCGTATG-ATGTCGTTTA |
| 49 | 4.6 | a4.6-b4.6-a3.6*-b3.5* | CAGATAAAGC-TACTAGCATTT-GCCGAGCCTTG-AATCTTTCTA |
| 50 | 4.7 | a4.7-b4.7-a3.7*-b3.6* | CGCCTCCTTC-TCAATAATAAT-GAGCTAAGTTG-AATTGCATAA |
| 51 | 4.8 | a4.8-b4.8-a3.8*-b3.7* | CCAACTAGGC-TGGACCATCGT-GATGGGAAGTG-ACGACTTTCA |
| 52 | 4.9 | a4.9-b4.9-a3.9*-b3.8* | CTAATGATGC-TAATGAACTAT-GCGCGGACTTG-ACCTGGTTTA |
| 53 | 4.10 | a4.10-b4.10-a3.10*-b3.9* | CCGCCAGTAC-TAAATACCTGT-GATTCTACACG-AATCTGACGA |
| 54 | 4.11 | a4.11-b4.11-a3.11*-b3.10* | CGTGGCGTTC-TACCATTGTTT-GCTCTCAGCTG-ATCAGCTCTA |
| 55 | 4.12 | a4.12-b4.12-a3.12*-b3.11* | CACTTTATTC-TATGAGTTAAT-GCCCTAAGATG-ACCGACCAAA |
| 56 | 4.13 | a4.13-b4.13-a3.13*-b3.12* | CCCGACCGTC-TGCCCTCGCTT-GTCGAGAAAGG-ATACACAGCA |
| 57 | 4.14 | a4.14-b4.14-a3.14*-b3.13* | CGGATTTGAC-TCACAGAGACT-GAAACAGGGCG-ACACTTCAGA |
| 58 | 4.15 | a4.15-11T-11T-b3.14* | CATGCTCGCC-TTTTTTTTTTT-TTTTTTTTTTT-AAGGGACTCA |
| 59 | 5.1 | a5.1-b5.1-a4.2*-b4.1* | CGGACTTCATC-TATGGTTTAT-GTAGAGCCTG-ATCCACTCCCA |
| 60 | 5.2 | a5.2-b5.2-a4.3*-b4.2* | CCGTTGATGAC-TGGGCGGATT-GTCTAGCGCG-ATATCCTCCCA |
| 61 | 5.3 | a5.3-b5.3-a4.4*-b4.3* | CTAATGGGACC-TCTGGTCCCT-GATAGCGTAG-ATATAAATGTA |
| 62 | 5.4 | a5.4-b5.4-a4.5*-b4.4* | CCACTTCCTTC-TTGGTTGCGT-GTTTACTCCG-ATAATGGTAAA |
| 63 | 5.5 | a5.5-b5.5-a4.6*-b4.5* | CAGTACATAGC-TAGGATGCAT-GCTTTATCTG-ACAAGGCACAA |
| 64 | 5.6 | a5.6-b5.6-a4.7*-b4.6* | CGAAGGGAGCC-TGGCATTTGT-GAAGGAGGCG-AAATGCTAGTA |
| 65 | 5.7 | a5.7-b5.7-a4.8*-b4.7* | CGCCAAGTAGC-TAGTCCGCAT-GCCTAGTTGG-ATTATTATTGA |
| 66 | 5.8 | a5.8-b5.8-a4.9*-b4.8* | CTAGCAGCATC-TAATCCATTT-GCATCATTAG-ACGATGGTCCA |
| 67 | 5.9 | a5.9-b5.9-a4.10*-b4.9* | CAAGCGCGTAC-TTACCTGACT-GTACTGGCGG-ATAGTTCATTA |

TABLE 1-continued

Single Stranded Oligonucleotides

| SEQ ID NO. | strand name | segment composition | segment sequences |
|---|---|---|---|
| 68 | 5.10 | a5.10-b5.10-a4.11*-b4.10* | CCCTGCGCACC-TTCGCCACGT-GAACGCCACG-ACAGGTATTTA |
| 69 | 5.11 | a5.11-b5.11-a4.12*-b4.11* | CCCTAACCCTC-TTTAGGTACT-GAATAAAGTG-AAACAATGGTA |
| 70 | 5.12 | a5.12-b5.12-a4.13*-b4.12* | CTGCAAACATC-TTACTGACCT-GACGGTCGGG-ATTAACTCATA |
| 71 | 5.13 | a5.13-b5.13-a4.14*-b4.13* | CATGGTACGGC-TAACATATCT-GTCAAATCCG-AAGCGAGGGCA |
| 72 | 5.14 | a5.14-b5.14-a4.15*-b4.14* | CATGCGGCTGC-TACCGGGCAT-GGCGAGCATG-AGTCTCTGTGA |
| 73 | 6.1 | 10T-b6.1-a5.1*-10T | TTTTTTTTTT-TGGAGGATTCT-GATGAAGTCCG-TTTTTTTTTT |
| 74 | 6.2 | a6.2-b6.2-a5.2*-b5.1* | CCCGTGGTCC-TCGCCCGAAAT-GTCATCAACGG-ATAAACCATA |
| 75 | 6.3 | a6.3-b6.3-a5.3*-b5.2* | CTTTATTGGC-TTCTCAGTTAT-GGTCCCATTAG-AATCCGCCCA |
| 76 | 6.4 | a6.4-b6.4-a5.4*-b5.3* | CACTAGAAGC-TTAAGGGTAAT-GAAGGAAGTGG-AGGGACCAGA |
| 77 | 6.5 | a6.5-b6.5-a5.5*-b5.4* | CGCGAGAGCC-TTCCTGTTATT-GCTATGTACTG-ACGCAACCAA |
| 78 | 6.6 | a6.6-b6.6-a5.6*-b5.5* | CGCGTCCTTC-TACGGCGAGAT-GGCTCCCTTCG-ATGCATCCTA |
| 79 | 6.7 | a6.7-b6.7-a5.7*-b5.6* | CCAGTTAGTC-TCAATGCAGTT-GCTACTTGGCG-ACAAATGCCA |
| 80 | 6.8 | a6.8-b6.8-a5.8*-b5.7* | CCAATACTCC-TCGGAGGCAGT-GATGCTGCTAG-ATGCGGACTA |
| 81 | 6.9 | a6.9-b6.9-a5.9*-b5.8* | CCAATCGGCC-TGCAGGCTGTT-GTACGCGCTTG-AAATGGATTA |
| 82 | 6.10 | a6.10-b6.10-a5.10*-b5.9* | CCCTATATTC-TCTTGGGCAAT-GGTGCGCAGGG-AGTCAGGTAA |
| 83 | 6.11 | a6.11-b6.11-a5.11*-b5.10* | CGGTGGCCGC-TACAACCAATT-GAGGGTTAGGG-ACGTGGCGAA |
| 84 | 6.12 | a6.12-b6.12-a5.12*-b5.11* | CTGTTGCTTC-TTTAGTTCTTT-GATGTTTGCAG-AGTACCTAAA |
| 85 | 6.13 | a6.13-b6.13-a5.13*-b5.12* | CAGCGTTGGC-TGAAACTCGCT-GCCGTACCATG-AGGTCAGTAA |
| 86 | 6.14 | a6.14-b6.14-a5.14*-b5.13* | CGTGGTCAGC-TTGCTCTAGTT-GCAGCCGCATG-AGATATGTTA |
| 87 | 6.15 | a6.15-11T-11T-b5.14* | CCCTGACGCC-TTTTTTTTTTT-TTTTTTTTTTT-ATGCCCGGTA |
| 88 | 7.1 | a7.1-b7.1-a6.2*-b6.1* | CGATTGGTCTC-TGAGACTTAT-GGACCACGGG-AGAATCCTCCA |
| 89 | 7.2 | a7.2-b7.2-a6.3*-b6.2* | CGGGCCGGTC-TATTGACAAT-GCCAATAAAG-ATTTCGGGCGA |
| 90 | 7.3 | a7.3-b7.3-a6.4*-b6.3* | CAGAGGATGGC-TTTCCGATGT-GCTTCTAGTG-ATAACTGAGAA |
| 91 | 7.4 | a7.4-b7.4-a6.5*-b6.4* | CACCAAGGGC-TCAACAACTT-GGCTCTCGCG-ATTACCCTTAA |
| 92 | 7.5 | a7.5-b7.5-a6.6*-b6.5* | CTTGTTCAGAC-TCGAATTCCT-GAAGGACGCG-AATAACAGGAA |
| 93 | 7.6 | a7.6-b7.6-a6.7*-b6.6* | CAGAGCATCCC-TACAGATGCT-GACTAACTGG-ATCTCGCCGTA |
| 94 | 7.7 | a7.7-b7.7-a6.8*-b6.7* | CGTACTGGTTC-TGACAGGTCT-GGAGTATTGG-AACTGCATTGA |
| 95 | 7.8 | a7.8-b7.8-a6.9*-b6.8* | CCTCGGACGCC-TAACTTCTGT-GGCCGATTGG-ACTGCCTCCGA |
| 96 | 7.9 | a7.9-b7.9-a6.10*-b6.9* | CCACCAAACTC-TATAGCCCGT-GAATATAGGG-AACAGCCTGCA |
| 97 | 7.10 | a7.10-b7.10-a6.11*-b6.10* | CATGAGTGAAC-TGTTAGGTCT-GCGGCCACCG-ATTGCCCAAGA |
| 98 | 7.11 | a7.11-b7.11-a6.12*-b6.11* | CTAGAGTACAC-TACCCGCATT-GAAGCAACAG-AATTGGTTGTA |
| 99 | 7.12 | a7.12-b7.12-a6.13*-b6.12* | CGAGAAGTATC-TATGCACCCT-GCCAACGCTG-AAAGAACTAAA |
| 100 | 7.13 | a7.13-b7.13-a6.14*-b6.13* | CTATTGAGGAC-TATCCAATCT-GCTGACCACG-AGCGAGTTTCA |
| 101 | 7.14 | a7.14-b7.14-a6.15*-b6.14* | CCGACTGCTGC-TGCGAATAGT-GGCGTCAGGG-AACTAGAGCAA |
| 102 | 8.1 | 10T-b8.1-a7.1*-10T | TTTTTTTTTT-TTGCTTGGGTT-GAGACCAATCG-TTTTTTTTTT |
| 103 | 8.2 | a8.2-b8.2-a7.2*-b7.1* | CCGCACAGCC-TCATACCCTCT-GAGCCGGCCCG-ATAAGTCTCA |
| 104 | 8.3 | a8.3-b8.3-a7.3*-b7.2* | CTAGGTTCCC-TTCCTTATAAT-GCCATCCTCTG-ATTGTCAATA |
| 105 | 8.4 | a8.4-b8.4-a7.4*-b7.3* | CTATGGCTAC-TCACAACCGTT-GCCCTTTGGTG-ACATCGGAAA |

TABLE 1-continued

Single Stranded Oligonucleotides

| SEQ ID NO. | strand name | segment composition | segment sequences |
|---|---|---|---|
| 106 | 8.5 | a8.5-b8.5-a7.5*-b7.4* | CGTGTTGTCC-TATATCACGCT-GTCTGAACAAG-AAGTTGTTGA |
| 107 | 8.6 | a8.6-b8.6-a7.6*-b7.5* | CGAGCGTCTC-TTGTTGTCTTT-GGGATGCTCTG-AGGAATTCGA |
| 108 | 8.7 | a8.7-b8.7-a7.7*-b7.6* | CTGACGCTCC-TCTGGACCTAT-GAACCAGTACG-AGCATCTGTA |
| 109 | 8.8 | a8.8-b8.8-a7.8*-b7.7* | CACATTTAAC-TAACTTATCCT-GGCGTCCGAGG-AGACCTGTCA |
| 110 | 8.9 | a8.9-b8.9-a7.9*-b7.8* | CAACATACGC-TTCGAGCCAGT-GAGTTTGGTGG-ACAGAAGTTA |
| 111 | 8.10 | a8.10-b8.10-a7.10*-b7.9* | CAATACTTCC-TACACCTATCT-GTTCACTCATG-ACGGGCTATA |
| 112 | 8.11 | a8.11-b8.11-a7.11*-b7.10* | CTTCCAGCCC-TTAAAGCGGAT-GTGTACTCTAG-AGACCTAACA |
| 113 | 8.12 | a8.12-b8.12-a7.12*-b7.11* | CCCTATCCAC-TTAGTTCGACT-GATACTTCTCG-AATGCGGGTA |
| 114 | 8.13 | a8.13-b8.13-a7.13*-b7.12* | CTCCAAGCCC-TCACGAAACAT-GTCCTCAATAG-AGGGTGCATA |
| 115 | 8.14 | a8.14-b8.14-a7.14*-b7.13* | CCTACGGATC-TGATGCACATT-GCAGCAGTCGG-AGATTGGATA |
| 116 | 8.15 | a8.15-11T-11T-b7.14* | CCAGCAACGC-TTTTTTTTTTT-TTTTTTTTTTT-ACTATTCGCA |
| 117 | 9.1 | a9.1-b9.1-a8.2*-b8.1* | CCTTACCGGAC-TTTCCGTAAT-GGCTGTGCGG-AACCCAAGCAA |
| 118 | 9.2 | a9.2-b9.2-a8.3*-b8.2* | CTTACCGCGGC-TAGTGCTCAT-GGGAACCTAG-AGAGGGTATGA |
| 119 | 9.3 | a9.3-b9.3-a8.4*-b8.3* | CTTGATCGAAC-TTGTCATATT-GTAGCCATAG-ATTATAAGGAA |
| 120 | 9.4 | a9.4-b9.4-a8.5*-b8.4* | CTGGTTTGATC-TCGTACCAAT-GGACAACACG-AACGGTTGTGA |
| 121 | 9.5 | a9.5-b9.5-a8.6*-b8.5* | CCCGTGTTGAC-TGCATAGTAT-GAGACGCTCG-AGCGTGATATA |
| 122 | 9.6 | a9.6-b9.6-a8.7*-b8.6* | CCGCTAGATCC-TCCTTGTGCT-GGAGCGTCAG-AAAGACAACAA |
| 123 | 9.7 | a9.7-b9.7-a8.8*-b8.7* | CGCAGGCTAGC-TTACGTTAGT-GTTAAATGTG-ATAGGTCCAGA |
| 124 | 9.8 | a9.8-b9.8-a8.9*-b8.8* | CTCCGGTCAAC-TAGTTAGTAT-GCGTATGTTG-AGGATAAGTTA |
| 125 | 9.9 | a9.9-b9.9-a8.10*-b8.9* | CGGTCTTTAAC-TGGGATTACT-GGAAGTATTG-ACTGGCTCGAA |
| 126 | 9.10 | a9.10-b9.10-a8.11*-b8.10* | CAGTTCGTCAC-TGGCTACCTT-GGGCTGGAAG-AGATAGGTGTA |
| 127 | 9.11 | a9.11-b9.11-a8.12*-b8.11* | CATACTGTCTC-TAACTGCAAT-GTGGATAGGG-ATCCGCTTTAA |
| 128 | 9.12 | a9.12-b9.12-a8.13*-b8.12* | CTTGGCTTTAC-TTATCGGCGT-GGGCTTGGAG-AGTCGAACTAA |
| 129 | 9.13 | a9.13-b9.13-a8.14*-b8.13* | CGTAAGGGCAC-TATCGTTTAT-GATCCGTAGG-ATGTTTCGTGA |
| 130 | 9.14 | a9.14-b9.14-a8.15*-b8.14* | CTCGCTTTAGC-TGGAGACCGT-GCGTTGCTGG-AATGTGCATCA |
| 131 | 10.1 | 10T-b10.1-a9.1*-10T | TTTTTTTTTT-TAGTGCAGAAT-GTCCGGTAAGG-TTTTTTTTTT |
| 132 | 10.2 | a10.2-b10.2-a9.2*-b9.1* | CATACCTCTC-TTAGGTCAATT-GCCGCGGTAAG-ATTACGGAAA |
| 133 | 10.3 | a10.3-b10.3-a9.3*-b9.2* | CACACCACAC-TCAGTAGGTTT-GTTCGATCAAG-ATGAGCACTA |
| 134 | 10.4 | a10.4-b10.4-a9.4*-b9.3* | CCACGCAGTC-TGGTCATCACT-GATCAAACCAG-AATATGACAA |
| 135 | 10.5 | a10.5-b10.5-a9.5*-b9.4* | CAACGCAAGC-TTTCTGATTAT-GTCAACACGGG-ATTGGTACGA |
| 136 | 10.6 | a10.6-b10.6-a9.6*-b9.5* | CGTAGTGGCC-TTACTAGGGTT-GGATCTAGCGG-ATACTATGCA |
| 137 | 10.7 | a10.7-b10.7-a9.7*-b9.6* | CTCGTGGAAC-TCAGGGCTCGT-GCTAGCCTGCG-AGCACAAGGA |
| 138 | 10.8 | a10.8-b10.8-a9.8*-b9.7* | CACCGCCCTC-TTACGCCCACT-GTTGACCGGAG-ACTAACGTAA |
| 139 | 10.9 | a10.9-b10.9-a9.9*-b9.8* | CGAATTAAAC-TAGACGAGTAT-GTTAAAGACCG-ATACTAACTA |
| 140 | 10.10 | a10.10-b10.10-a9.10*-b9.9* | CATAAGCGAC-TTTGATCGGCT-GTGACGAACTG-AGTAATCCCA |
| 141 | 10.11 | a10.11-b10.11-a9.11*-b9.10* | CATGCAACCC-TGTAAGCAAAT-GAGACAGTATG-AAGGTAGCCA |
| 142 | 10.12 | a10.12-b10.12-a9.12*-b9.11* | CACTACTGGC-TTGTAAGCGCT-GTAAAGCCAAG-ATTGCAGTTA |

TABLE 1-continued

Single Stranded Oligonucleotides

| SEQ ID NO. | strand name | segment composition | segment sequences |
|---|---|---|---|
| 143 | 10.13 | a10.13-b10.13-a9.13*-b9.12* | CTGTAAGGTC-TCGAGATGTGT-GTGCCCTTACG-ACGCCGATAA |
| 144 | 10.14 | a10.14-b10.14-a9.14*-b9.13* | CCGTCTAACC-TATAATATTGT-GCTAAAGCGAG-ATAAACGATA |
| 145 | 10.15 | a10.15-11T-11T-b9.14* | CGGCAACGTC-TTTTTTTTTTT-TTTTTTTTTTT-ACGGTCTCCA |
| 146 | 11.1 | a11.1-b11.1-a10.2*-b10.1* | CCTTTGCTTCC-TTGACCAAGT-GAGAGGTATG-ATTCTGCACTA |
| 147 | 11.2 | a11.2-b11.2-a10.3*-b10.2* | CGTGGAGGCGC-TCACCCTCCT-GTGTGGTGTG-AATTGACCTAA |
| 148 | 11.3 | a11.3-b11.3-a10.4*-b10.3* | CTCGCCAACCC-TTGTCCAGGT-GACTGCGTGG-AAACCTACTGA |
| 149 | 11.4 | a11.4-b11.4-a10.5*-b10.4* | CGCTTCTTCAC-TGCATGCGAT-GCTTGCGTTG-AGTGATGACCA |
| 150 | 11.5 | a11.5-b11.5-a10.6*-b10.5* | CAGATATAGCC-TAGCCCTCGT-GGCCACTACG-ATAATCAGAAA |
| 151 | 11.6 | a11.6-b11.6-a10.7*-b10.6* | CATCCGCAGCC-TTACACTAAT-GTTCCACGAG-AACCCTAGTAA |
| 152 | 11.7 | a11.7-b11.7-a10.8*-b10.7* | CGATGCAGATC-TTCTGCCTTT-GAGGGCGGTG-ACGAGCCCTGA |
| 153 | 11.8 | a11.8-b11.8-a10.9*-b10.8* | CAATAGCCATC-TCACTTGATT-GTTTAATTCG-AGTGGGCGTAA |
| 154 | 11.9 | a11.9-b11.9-a10.10*-b10.9* | CGTCCTTGGAC-TCAACGTCCT-GTCGCTTATG-ATACTCGTCTA |
| 155 | 11.10 | a11.10-b11.10-a10.11*-b10.10* | CTGCGAAGGCC-TACAGGCACT-GGGTTGCATG-AGCCGATCAAA |
| 156 | 11.11 | a11.11-b11.11-a10.12*-b10.11* | CTTCTTCGAAC-TGGACATCTT-GCCAGTAGTG-ATTTGCTTACA |
| 157 | 11.12 | a11.12-b11.12-a10.13*-b10.12* | CAGTCGTGTCC-TTATGACTAT-GACCTTACAG-AGCGCTTACAA |
| 158 | 11.13 | a11.13-b11.13-a10.14*-b10.13* | CATTACATGGC-TAATGCTGAT-GGTTAGACGG-ACACATCTCGA |
| 159 | 11.14 | a11.14-b11.14-a10.15*-b10.14* | CCAGCATCCAC-TGCGGTAACT-GACGTTGCCG-ACAATATTATA |
| 160 | 12.1 | 10T-b12.1-a11.1*-10T | TTTTTTTTTT-TCTGTGCATAT-GGAAGCAAAGG-TTTTTTTTTT |
| 161 | 12.2 | a12.2-b12.2-a11.2*-b11.1* | CTGGCGACGC-TCTGACCGTGT-GCGCCTCCACG-ACTTGGTCAA |
| 162 | 12.3 | a12.3-b12.3-a11.3*-b11.2* | CTTGGTCTAC-TGTTTATAGAT-GGGTTGGCGAG-AGGAGGGTGA |
| 163 | 12.4 | a12.4-b12.4-a11.4*-b11.3* | CGCGCGCCAC-TCATTAGGAGT-GTGAAGAAGCG-ACCTGGACAA |
| 164 | 12.5 | a12.5-b12.5-a11.5*-b11.4* | CCAGATTTAC-TTGTACCCAGT-GGCTATATCTG-ATCGCATGCA |
| 165 | 12.6 | a12.6-b12.6-a11.6*-b11.5* | CGGCGCGCTC-TGCTAGCTGGT-GGCTGCGGATG-ACGAGGGCTA |
| 166 | 12.7 | a12.7-b12.7-a11.7*-b11.6* | CGCGCTCCGC-TCACTCGGAAT-GATCTGCATCG-ATTAGTGTAA |
| 167 | 12.8 | a12.8-b12.8-a11.8*-b11.7* | CATCGGTACC-TTTGGGCGGGT-GATGGCTATTG-AAAGGCAGAA |
| 168 | 12.9 | a12.9-b12.9-a11.9*-b11.8* | CAAATTGATC-TTATAACTACT-GTCCAAGGACG-AATCAAGTGA |
| 169 | 12.10 | a12.10-b12.10-a11.10*-b11.9* | CTTCACGGAC-TCCGGATTCAT-GGCCTTCGCAG-AGGACGTTGA |
| 170 | 12.11 | a12.11-b12.11-a11.11*-b11.10* | CGCGCCTGAC-TCTGGCTGTAT-GTTCGAAGAAG-AGTGCCTGTA |
| 171 | 12.12 | a12.12-b12.12-a11.12*-b11.11* | CTCAAACCTC-TCGTCGAGTGT-GGACACGACTG-AAGATGTCCA |
| 172 | 12.13 | a12.13-b12.13-a11.13*-b11.12* | CATACATCAC-TCGAGAATCGT-GCCATGTAATG-ATAGTCATAA |
| 173 | 12.14 | a12.14-b12.14-a11.14*-b11.13* | CCACGGGTGC-TGATCGTCCGT-GTGGATGCTGG-ATCAGCATTA |
| 174 | 12.15 | a12.15-11T-11T-b11.14* | CCACCTCCTC-TTTTTTTTTTT-TTTTTTTTTTT-AGTTACCGCA |
| 175 | 13.1 | a13.1-b13.1-a12.2*-b12.1* | CCCGAAGTACC-TCTGCAGGAT-GCGTCGCCAG-ATATGCACAGA |
| 176 | 13.2 | a13.2-b13.2-a12.3*-b12.2* | CGTTACCAGGC-TACGATGAGT-GTAGACCAAG-ACACGGTCAGA |
| 177 | 13.3 | a13.3-b13.3-a12.4*-b12.3* | CTGTCCCACTC-TCCTTCAAAT-GTGGCGCGCG-ATCTATAAACA |
| 178 | 13.4 | a13.4-b13.4-a12.5*-b12.4* | CATTATATTGC-TCCTGAGGGT-GTAAATCTGG-ACTCCTAATGA |
| 179 | 13.5 | a13.5-b13.5-a12.6*-b12.5* | CGTGCATGCCC-TCCCAAACTT-GAGCGCGCCG-ACTGGGTACAA |
| 180 | 13.6 | a13.6-b13.6-a12.7*-b12.6* | CATTGCACTGC-TCTACCCTTT-GCGGAGCGCG-ACCAGCTAGCA |

TABLE 1-continued

Single Stranded Oligonucleotides

| SEQ ID NO. | strand name | segment composition | segment sequences |
|---|---|---|---|
| 181 | 13.7 | a13.7-b13.7-a12.8*-b12.7* | CTTCATCGACC-TGTTTAGGTT-GGTACCGATG-ATTCCGAGTGA |
| 182 | 13.8 | a13.8-b13.8-a12.9*-b12.8* | CTACCGGCGTC-TGGACACCAT-GATCAATTTG-ACCCGCCCAAA |
| 183 | 13.9 | a13.9-b13.9-a12.10*-b12.9* | CCGCGGTGTGC-TGCATTCGCT-GTCCGTGAAG-AGTAGTTATAA |
| 184 | 13.10 | a13.10-b13.10-a12.11*-b12.10* | CCCGAGGTTCC-TGATCTCCAT-GTCAGGCGCG-ATGAATCCGGA |
| 185 | 13.11 | a13.11-b13.11-a12.12*-b12.11* | CATGAGCGTGC-TACCCGTTAT-GAGGTTTGAG-ATACAGCCAGA |
| 186 | 13.12 | a13.12-b13.12-a12.13*-b12.12* | CTCTGGAATAC-TAAGAATGTT-GTGATGTATG-ACACTCGACGA |
| 187 | 13.13 | a13.13-b13.13-a12.14*-b12.13* | CTATTCGTTGC-TCTGTCCTGT-GCACCCGTGG-ACGATTCTCGA |
| 188 | 13.14 | a13.14-b13.14-a12.15*-b12.14* | CCCTCGCAGAC-TCCCGACAGT-GAGGAGGTGG-ACGGACGATCA |
| 189 | 14.1 | 10T-b14.1-a13.1*-10T | TTTTTTTTTT-TGTTACTTGAT-GGTACTTCGGG-TTTTTTTTTT |
| 190 | 14.2 | a14.2-b14.2-a13.2*-b13.1* | CCGATGCGAC-TTGATATGTCT-GCCTGGTAACG-ATCCTGCAGA |
| 191 | 14.3 | a14.3-b14.3-a13.3*-b13.2* | CGCTGCCAGC-TTCAGGGCCTT-GAGTGGGACAG-ACTCATCGTA |
| 192 | 14.4 | a14.4-b14.4-a13.4*-b13.3* | CAGAAGGGTC-TGTGTAACTGT-GCAATATAATG-ATTTGAAGGA |
| 193 | 14.5 | a14.5-b14.5-a13.5*-b13.4* | CGAGCGCCGC-TGCGGCTATTT-GGGCATGCACG-ACCCTCAGGA |
| 194 | 14.6 | a14.6-b14.6-a13.6*-b13.5* | CAGGAGGCTC-TCCAACCGCTT-GCAGTGCAATG-AAGTTTGGGA |
| 195 | 14.7 | a14.7-b14.7-a13.7*-b13.6* | CTGGGACGAC-TGGCACGTCAT-GGTCGATGAAG-AAAGGGTAGA |
| 196 | 14.8 | a14.8-b14.8-a13.8*-b13.7* | CTGCACCAGC-TGCGTCGTTGT-GACGCCGGTAG-AACCTAAACA |
| 197 | 14.9 | a14.9-b14.9-a13.9*-b13.8* | CAAAGGAAAC-TAACAGTGTCT-GCACACCGCG-ATGGTGTCCA |
| 198 | 14.10 | a14.10-b14.10-a13.10*-b13.9* | CTCTGCTCTC-TTTACTGGTGT-GGAACCTCGGG-AGCGAATGCA |
| 199 | 14.11 | a14.11-b14.11-a13.11*-b13.10* | CATGTAAGAC-TACGAATCGCT-GCACGCTCATG-ATGGAGATCA |
| 200 | 14.12 | a14.12-b14.12-a13.12*-b13.11* | CTTTAGGAAC-TAATCTTTGTT-GTATTCCAGAG-ATAACGGGTA |
| 201 | 14.13 | a14.13-b14.13-a13.13*-b13.12* | CCCAGCGATC-TGTTGCATCGT-GCAACGAATAG-AACATTCTTA |
| 202 | 14.14 | a14.14-b14.14-a13.14*-b13.13* | CACGAACAGC-TAACCTTAACT-GTCTGCGAGGG-ACAGGACAGA |
| 203 | 14.15 | a14.15-11T-11T-b13.14* | CTATAGTAAC-TTTTTTTTTTT-TTTTTTTTTTT-ACTGTCGGGA |
| 204 | 15.1 | a15.1-b15.1-a14.2*-b14.1* | CTGGGCAAGCC-TTATTGCGAT-GTCGCATCGG-ATCAAGTAACA |
| 205 | 15.2 | a15.2-b15.2-a14.3*-b14.2* | CGTGCGGTCCC-TACGCGCAGT-GCTGGCAGCG-AGACATATCAA |
| 206 | 15.3 | a15.3-b15.3-a14.4*-b14.3* | CGCGGGCCGCC-TTTCAATTAT-GACCCTTCTG-AAGGCCCTGAA |
| 207 | 15.4 | a15.4-b15.4-a14.5*-b14.4* | CTATCTTGTAC-TGCACCGGTT-GCGGCGCTCG-ACAGTTACACA |
| 208 | 15.5 | a15.5-b15.5-a14.6*-b14.5* | CCAAACCGTCC-TCCTACGTTT-GAGCCTCCTG-AAATAGCCGCA |
| 209 | 15.6 | a15.6-b15.6-a14.7*-b14.6* | CATGTCCCAAC-TGGAGTCTTT-GTCGTCCCAG-AAGCGGTTGGA |
| 210 | 15.7 | a15.7-b15.7-a14.8*-b14.7* | CCAGCGCGTTC-TGTGTCTTAT-GCTGGTGCAG-ATGACGTGCCA |
| 211 | 15.8 | a15.8-b15.8-a14.9*-b14.8* | CTTGACCGCTC-TGGAGATTCT-GTTTCCTTTG-ACAACGACGCA |
| 212 | 15.9 | a15.9-b15.9-a14.10*-b14.9* | CTGCGGGCCAC-TCGCGCCATT-GAGAGCAGAG-AGACACTGTTA |
| 213 | 15.10 | a15.10-b15.10-a14.11*-b14.10* | CTACCTTAGTC-TAAAGTAATT-GTCTTACATG-ACACCAGTAAA |
| 214 | 15.11 | a15.11-b15.11-a14.12*-b14.11* | CTACTTGCTGC-TCGTTCCTCT-GTTCCTAAAG-AGCGATTCGTA |
| 215 | 15.12 | a15.12-b15.12-a14.13*-b14.12* | CAGTATCTGCC-TAATTTGCGT-GATCGCTGGG-AACAAAGATTA |
| 216 | 15.13 | a15.13-b15.13-a14.14*-b14.13* | CGCTTTGGCAC-TAGTAGCGGT-GCTGTTCGTG-ACGATGCAACA |
| 217 | 15.14 | a15.14-b15.14-a14.15*-b14.14* | CGGTGTTGCAC-TTAACAGCTT-GTTACTATAG-AGTTAAGGTTA |

TABLE 1-continued

Single Stranded Oligonucleotides

| SEQ ID NO. | strand name | segment composition | segment sequences |
|---|---|---|---|
| 218 | 16.1 | 10T-b16.1-a15.1*-10T | TTTTTTTTTT-TGGCCCATCAT-GGCTTGCCCAG-TTTTTTTTTT |
| 219 | 16.2 | a16.2-b16.2-a15.2*-b15.1* | CAAGACATAC-TATTCTGTATT-GGGACCGCACG-ATCGCAATAA |
| 220 | 16.3 | a16.3-b16.3-a15.3*-b15.2* | CTAGACCACC-TCTTTCTTTAT-GGCGGCCCGCG-ACTGCGCGTA |
| 221 | 16.4 | a16.4-b16.4-a15.4*-b15.3* | CCCTTGTGGC-TAAGGAGGTCT-GTACAAGATAG-ATAATTGAAA |
| 222 | 16.5 | a16.5-b16.5-a15.5*-b15.4* | CACCGAACCC-TTCCGCTCGCT-GGACGGTTTGG-AACCGGTGCA |
| 223 | 16.6 | a16.6-b16.6-a15.6*-b15.5* | CCTGAAGTTC-TTGATCCCGAT-GTTGGGACATG-AAACGTAGGA |
| 224 | 16.7 | a16.7-b16.7-a15.7*-b15.6* | CTGAGTGACC-TTCCATCCATT-GAACGCGCTGG-AAAGACTCCA |
| 225 | 16.8 | a16.8-b16.8-a15.8*-b15.7* | CCCTCAGCAC-TCACTTCTGGT-GAGCGGTCAAG-ATAAGACACA |
| 226 | 16.9 | a16.9-b16.9-a15.9*-b15.8* | CTGGTAGGAC-TCCATCCGTAT-GTGGCCCGCAG-AGAATCTCCA |
| 227 | 16.10 | a16.10-b16.10-a15.10*-b15.9* | CGTGCCCTGC-TAAACCGCGTT-GACTAAGGTAG-AATGGCGCGA |
| 228 | 16.11 | a16.11-b16.11-a15.11*-b15.10* | CCAACATTAC-TTCCGCGGGAT-GCAGCAAGTAG-AATTACTTTA |
| 229 | 16.12 | a16.12-b16.12-a15.12*-b15.11* | CGACAAACAC-TTGCATTACGT-GGCAGATACTG-AGAGGAACGA |
| 230 | 16.13 | a16.13-b16.13-a15.13*-b15.12* | CGCCCACCGC-TAAGTGCGTCT-GTGCCAAAGCG-ACGCAAATTA |
| 231 | 16.14 | a16.14-b16.14-a15.14*-b15.13* | CGGGACGAGC-TCAACGCTTGT-GTGCAACACCG-ACCGCTACTA |
| 232 | 16.15 | a16.15-11T-11T-b15.14* | CATTGTACTC-TTTTTTTTTTT-TTTTTTTTTTT-AAGCTGTTAA |
| 233 | 17.1 | a17.1-b17.1-a16.2*-b16.1* | CTTTGGGTACC-TAGACGGGT-GTATGTCTTG-ATGATGGGCCA |
| 234 | 17.2 | a17.2-b17.2-a16.3*-b16.2* | CGCATGTCCGC-TCCAGAAAGT-GGTGGTCTAG-AATACAGAATA |
| 235 | 17.3 | a17.3-b17.3-a16.4*-b16.3* | CTAAGGACGTC-TCCAATTCAT-GCCACAAGGG-ATAAAGAAAGA |
| 236 | 17.4 | a17.4-b17.4-a16.5*-b16.4* | CAAATGCATAC-TTTGTTTAGT-GGGTTCGGTG-AGACCTCCTTA |
| 237 | 17.5 | a17.5-b17.5-a16.6*-b16.5* | CACTTAGAGTC-TGGGCCCGGT-GAACTTCAGG-AGCGAGCGGAA |
| 238 | 17.6 | a17.6-b17.6-a16.7*-b16.6* | CTCTCATGTAC-TATGTTCAGT-GGTCACTCAG-ATCGGGATCAA |
| 239 | 17.7 | a17.7-b17.7-a16.8*-b16.7* | CCAGCTGTCAC-TGCGCCACCT-GTGCTGAGGG-AATGGATGGAA |
| 240 | 17.8 | a17.8-b17.8-a16.9*-b16.8* | CATCTGATATC-TCGGAACGAT-GTCCTACCAG-ACCAGAAGTGA |
| 241 | 17.9 | a17.9-b17.9-a16.10*-b16.9* | CTACTATTGCC-TGCTCGAGGT-GCAGGGCACG-ATACGGATGGA |
| 242 | 17.10 | a17.10-b17.10-a16.11*-b16.10* | CTGCAGAAACC-TGCTCCTCGT-GTAATGTTGG-AACGCGGTTTA |
| 243 | 17.11 | a17.11-b17.11-a16.12*-b16.11* | CTTGAGGGATC-TGTAAATTAT-GTGTTTGTCG-ATCCCGCGGAA |
| 244 | 17.12 | a17.12-b17.12-a16.13*-b16.12* | CAGGAGTCACC-TATGCTCATT-GCGGTGGGCG-ACGTAATGCAA |
| 245 | 17.13 | a17.13-b17.13-a16.14*-b16.13* | CAAACTACTAC-TCGCGTAAAT-GCTCGTCCCG-AGACGCACTTA |
| 246 | 17.14 | a17.14-b17.14-a16.15*-b16.14* | CGAATGGGCTC-TAGATGTCAT-GAGTACAATG-ACAAGCGTTGA |
| 247 | 18.1 | 10T-b18.1-a17.1*-10T | TTTTTTTTTT-TTCCAGACTAT-GGTACCCAAAG-TTTTTTTTTT |
| 248 | 18.2 | a18.2-b18.2-a17.2*-b17.1* | CGTTCGCTTC-TGCTGGGCCGT-GCGGACATGCG-AACCCGTCTA |
| 249 | 18.3 | a18.3-b18.3-a17.3*-b17.2* | CACCCTTACC-TTTCTGCCAAT-GACGTCCTTAG-ACTTTCTGGA |
| 250 | 18.4 | a18.4-b18.4-a17.4*-b17.3* | CGCCTCACAC-TGTCAGAGTTT-GTATGCATTTG-ATGAATTGGA |
| 251 | 18.5 | a18.5-b18.5-a17.5*-b17.4* | CTAACCTGCC-TGACCGATCGT-GACTCTAAGTG-ACTAAACAAA |
| 252 | 18.6 | a18.6-b18.6-a17.6*-b17.5* | CGACGATACC-TAAGGCGTGGT-GTACATGAGAG-ACCGGGCCCA |
| 253 | 18.7 | a18.7-b18.7-a17.7*-b17.6* | CTTCGCCTGC-TTACCATGTCT-GTGACAGCTGG-ACTGAACATA |
| 254 | 18.8 | a18.8-b18.8-a17.8*-b17.7* | CTATACGGCC-TGGTGGTAATT-GATATCAGATG-AGGTGGCGCA |
| 255 | 18.9 | a18.9-b18.9-a17.9*-b17.8* | CACGCACGCC-TATGCCTTGGT-GGCAATAGTAG-ATCGTTCCGA |

TABLE 1-continued

Single Stranded Oligonucleotides

| SEQ ID NO. | strand name | segment composition | segment sequences |
|---|---|---|---|
| 256 | 18.10 | a18.10-b18.10-a17.10*-b17.9* | CGACATGTGC-TAGTGTTCGCT-GGTTTCTGCAG-ACCTCGAGCA |
| 257 | 18.11 | a18.11-b18.11-a17.11*-b17.10* | CACTACGTTC-TCGCACAAAGT-GATCCCTCAAG-ACGAGGAGCA |
| 258 | 18.12 | a18.12-b18.12-a17.12*-b17.11* | CCACAGCAAC-TAAGTCCATAT-GGTGACTCCTG-ATAATTTACA |
| 259 | 18.13 | a18.13-b18.13-a17.13*-b17.12* | CTTCTGCGCC-TTGACTGTCAT-GTAGTAGTTTG-AATGAGCATA |
| 260 | 18.14 | a18.14-b18.14-a17.14*-b17.13* | CGATCACCGC-TCGTAAACTAT-GAGCCCATTCG-ATTTACGCGA |
| 261 | 18.15 | a18.15-11T-11T-b17.14* | CTAACCGCAC-TTTTTTTTTTT-TTTTTTTTTTT-ATGACATCTA |
| 262 | 19.1 | a19.1-b19.1-a18.2*-b18.1* | CTGAGATGATC-TCAAACGAAT-GAAGCGAACG-ATAGTCTGGAA |
| 263 | 19.2 | a19.2-b19.2-a18.3*-b18.2* | CCCTTCCCGCC-TTAGGCGGCT-GGTAAGGGTG-ACGGCCCAGCA |
| 264 | 19.3 | a19.3-b19.3-a18.4*-b18.3* | CCTGGCTAGTC-TATTGTTAAT-GTGTGAGGCG-ATTGGCAGAAA |
| 265 | 19.4 | a19.4-b19.4-a18.5*-b18.4* | CTACGTGGAGC-TATTAGGGAT-GGCAGGTTAG-AAACTCTGACA |
| 266 | 19.5 | a19.5-b19.5-a18.6*-b18.5* | CTGACATTACC-TCACAATCCT-GGTATCGTCG-ACGATCGGTCA |
| 267 | 19.6 | a19.6-b19.6-a18.7*-b18.6* | CTAGGCGTTTC-TTATGTCCTT-GCAGGCGAAG-ACCACGCCTTA |
| 268 | 19.7 | a19.7-b19.7-a18.8*-b18.7* | CTTAAGGTGCC-TATATAATTT-GGCCGTATAG-AGACATGGTAA |
| 269 | 19.8 | a19.8-b19.8-a18.9*-b18.8* | CAACACTGGAC-TAGAACAACT-GGCGTGCGTG-AATTACCACCA |
| 270 | 19.9 | a19.9-b19.9-a18.10*-b18.9* | CCCTCGTTTAC-TTCTTAGGCT-GCACATGTCG-ACCAAGGCATA |
| 271 | 19.10 | a19.10-b19.10-a18.11*-b18.10* | CGACAGTCGCC-TGTGGTTAGT-GAACGTAGTG-AGCGAACACTA |
| 272 | 19.11 | a19.11-b19.11-a18.12*-b18.11* | CCGTACATCTC-TAAAGCAGAT-GTTGCTGTGG-ACTTTGTGCGA |
| 273 | 19.12 | a19.12-b19.12-a18.13*-b18.12* | CGGACCAGGGC-TGGGCTCGAT-GGCGCAGAAG-ATATGGACTTA |
| 274 | 19.13 | a19.13-b19.13-a18.14*-b18.13* | CTCGGAAGCTC-TCCTACATAT-GCGGTGATCG-ATGACAGTCAA |
| 275 | 19.14 | a19.14-b19.14-a18.15*-b18.14* | CGCCCGGGAAC-TTCGGCCTAT-GTGCGGTTAG-ATAGTTTACGA |
| 276 | 20.1 | 10T-b20.1-a19.1*-10T | TTTTTTTTTT-TTACCTTGCTT-GATCATCTCAG-TTTTTTTTTT |
| 277 | 20.2 | a20.2-b20.2-a19.2*-b19.1* | CGCTTAAGTC-TTGGCGCTAAT-GGCGGGAAGGG-ATTCGTTTGA |
| 278 | 20.3 | a20.3-b20.3-a19.3*-b19.2* | CCCTAGGCCC-TAGCTGCATGT-GACTAGCCAGG-AGCCGCCTAA |
| 279 | 20.4 | a20.4-b20.4-a19.4*-b19.3* | CTAAGCCTTC-TGTTAATTCTT-GCTCCACGTAG-ATTAACAATA |
| 280 | 20.5 | a20.5-b20.5-a19.5*-b19.4* | CGGGCTCCAC-TGTAAGTGCTT-GGTAATGTCAG-ATCCCTAATA |
| 281 | 20.6 | a20.6-b20.6-a19.6*-b19.5* | CTCTGTTATC-TGGTAGTAGGT-GAAACGCCTAG-AGGATTGTGA |
| 282 | 20.7 | a20.7-b20.7-a19.7*-b19.6* | CCCGTGCGAC-TACAATTAGAT-GGCACCTTAAG-AAGGACATAA |
| 283 | 20.8 | a20.8-b20.8-a19.8*-b19.7* | CACCAACGGC-TAGGCACGGCT-GTCCAGTGTTG-AAATTATATA |
| 284 | 20.9 | a20.9-b20.9-a19.9*-b19.8* | CTGGGCAGTC-TACGAACTCTT-GTAAACGAGGG-AGTTGTTCTA |
| 285 | 20.10 | a20.10-b20.10-a19.10*-b19.9* | CGAGCGATAC-TCACCCATTGT-GGCGACTGTCG-AGCCTAAGAA |
| 286 | 20.11 | a20.11-b20.11-a19.11*-b19.10* | CGTTATGCCC-TTCAAGATTAT-GAGATGTACGG-ACTAACCACA |
| 287 | 20.12 | a20.12-b20.12-a19.12*-b19.11* | CTGAAGGTCC-TCCAGAGTGCT-GCCCTGGTCCG-ATCTGCTTTA |
| 288 | 20.13 | a20.13-b20.13-a19.13*-b19.12* | CGGGCTTTGC-TGAGCTGTGTT-GAGCTTCCGAG-ATCGAGCCCA |
| 289 | 20.14 | a20.14-b20.14-a19.14*-b19.13* | CGGCTACTTC-TGATCTTGGGT-GTTCCCGGGCA-ATATGTAGGA |
| 290 | 20.15 | a20.15-11T-11T-b19.14* | CGTCATATCC-TTTTTTTTTTT-TTTTTTTTTTT-ATAGGCCGAA |
| 291 | 21.1 | a21.1-b21.1-a20.2*-b20.1* | CTTGCTTTGCC-TCCTAACGAT-GACTTAAGCG-AAGCAAGGTAA |
| 292 | 21.2 | a21.2-b21.2-a20.3*-b20.2* | CAATACACCGC-TGCAAGACCT-GGGCCTAGGG-ATTAGCGCCAA |

TABLE 1-continued

Single Stranded Oligonucleotides

| SEQ ID NO. | strand name | segment composition | segment sequences |
|---|---|---|---|
| 293 | 21.3 | a21.3-b21.3-a20.4*-b20.3* | CTTGGGACGGC-TTTGGAAATT-GAAGGCTTAG-ACATGCAGCTA |
| 294 | 21.4 | a21.4-b21.4-a20.5*-b20.4* | CCAATTAGGAC-TAATTTAGAT-GTGGAGCCCG-AAGAATTAACA |
| 295 | 21.5 | a21.5-b21.5-a20.6*-b20.5* | CTTTGGCCATC-TTATCCAAAT-GATAACAGAG-AAGCACTTACA |
| 296 | 21.6 | a21.6-b21.6-a20.7*-b20.6* | CCCTGGTTATC-TCCTATCCTT-GTCGCACGGG-ACCTACTACCA |
| 297 | 21.7 | a21.7-b21.7-a20.8*-b20.7* | CTATTGTCCTC-TAAGGGTCCT-GCCGTTGGTG-ATCTAATTGTA |
| 298 | 21.8 | a21.8-b21.8-a20.9*-b20.8* | CTTTGCAATAC-TACCGGAACT-GACTGCCCAG-AGCCGTGCCTA |
| 299 | 21.9 | a21.9-b21.9-a20.10*-b20.9* | CCTACAGCGTC-TATGGCAAAT-GTATCGCTCG-AAGAGTTCGTA |
| 300 | 21.10 | a21.10-b21.10-a20.11*-b20.10* | CGGATCACCTC-TCACAGGCCT-GGGCATAACG-ACAATGGGTGA |
| 301 | 21.11 | a21.11-b21.11-a20.12*-b20.11* | CCTAGCATCTC-TCTGGTGTTT-GGACCTTCAG-ATAATCTTGAA |
| 302 | 21.12 | a21.12-b21.12-a20.13*-b20.12* | CATAGCGGAAC-TTTAACAAGT-GCAAAGCCCG-AGCACTCTGGA |
| 303 | 21.13 | a21.13-b21.13-a20.14*-b20.13* | CGACCGCCATC-TATCTCAGGT-GAAGTAGCCG-AACACAGCTCA |
| 304 | 21.14 | a21.14-b21.14-a20.15*-b20.14* | CTGTGATGGAC-TACGGAACAT-GGATATGACG-ACCCAAGATCA |
| 305 | 22.1 | 10T-b22.1-a21.1*-10T | TTTTTTTTTT-TGTTGTTTGTT-GGCAAAGCAAG-TTTTTTTTTT |
| 306 | 22.2 | a22.2-b22.2-a21.2*-b21.1* | CTCTGACGGC-TACATTGAGGT-GCGGTGTATTG-ATCGTTAGGA |
| 307 | 22.3 | a22.3-b22.3-a21.3*-b21.2* | CGGAAGTGCC-TCCATGATTGT-GCCGTCCCAAG-AGGTCTTGCA |
| 308 | 22.4 | a22.4-b22.4-a21.4*-b21.3* | CTACCATGGC-TGCTCACGAGT-GTCCTAATTGG-AATTTCCAAA |
| 309 | 22.5 | a22.5-b22.5-a21.5*-b21.4* | CTTAGTCGGC-TGCCGATAGTT-GATGGCCAAAG-ATCTAAATTA |
| 310 | 22.6 | a22.6-b22.6-a21.6*-b21.5* | CGCAAGCGCC-TGTATCAGGTT-GATAACCAGGG-ATTTGGATAA |
| 311 | 22.7 | a22.7-b22.7-a21.7*-b21.6* | CTGGTGACGC-TTCTAATTCGT-GAGGACAATAG-AAGGATAGGA |
| 312 | 22.8 | a22.8-b22.8-a21.8*-b21.7* | CAGGAGAACC-TCTTCAACAAT-GTATTGCAAAG-AGGACCCTTA |
| 313 | 22.9 | a22.9-b22.9-a21.9*-b21.8* | CCCTCTACAC-TTCGGTGCTAT-GACGCTGTAGG-AGTTCCGGTA |
| 314 | 22.10 | a22.10-b22.10-a21.10*-b21.9* | CGGACTTAAC-TCGAGCTCCGT-GAGGTGATCCG-ATTTGCCATA |
| 315 | 22.11 | a22.11-b22.11-a21.11*-b21.10* | CCTGGCGATC-TCACAAAGCGT-GAGATGCTAGG-AGGCCTGTGA |
| 316 | 22.12 | a22.12-b22.12-a21.12*-b21.11* | CGTGAGTCGC-TAAAGGGCGCT-GTTCCGCTATG-AAACACCAGA |
| 317 | 22.13 | a22.13-b22.13-a21.13*-b21.12* | CCCTCCCTAC-TGTATGCCACT-GATGGCGGTCG-ACTTGTTAAA |
| 318 | 22.14 | a22.14-b22.14-a21.14*-b21.13* | CTAGAATTGC-TGCCTCTCATT-GTCCATCACAG-ACCTGAGATA |
| 319 | 22.15 | a22.15-11T-11T-b21.14* | CGGCTGGGAC-TTTTTTTTTTT-TTTTTTTTTTT-ATGTTCCGTA |
| 320 | 23.1 | a23.1-b23.1-a22.2*-b22.1* | CATGCCTGCCC-TTGCTAACTT-GCCGTCAGAG-AACAAACAACA |
| 321 | 23.2 | a23.2-b23.2-a22.3*-b22.2* | CAAGACTATAC-TCAGGACGCT-GGCACTTCCG-ACCTCAATGTA |
| 322 | 23.3 | a23.3-b23.3-a22.4*-b22.3* | CACGCGCATCC-TCCGTTTATT-GCCATGGTAG-ACAATCATGGA |
| 323 | 23.4 | a23.4-b23.4-a22.5*-b22.4* | CGTAAAGCTGC-TATGGTCTAT-GCCGACTAAG-ACTCGTGAGCA |
| 324 | 23.5 | a23.5-b23.5-a22.6*-b22.5* | CGTGAATGCAC-TCGGTAGACT-GGCGCTTGCG-AACTATCGGCA |
| 325 | 23.6 | a23.6-b23.6-a22.7*-b22.6* | CTCGGTAATAC-TTTATGCTAT-GCGTCACCAG-AACCTGATACA |
| 326 | 23.7 | a23.7-b23.7-a22.8*-b22.7* | CAAGAGTCTCC-TTTAGACAGT-GGTTCTCCTG-ACGAATTAGAA |
| 327 | 23.8 | a23.8-b23.8-a22.9*-b22.8* | CCGGCTGGCCC-TGGGCTGCGT-GTGTAGAGGG-ATTGTTGAAGA |
| 328 | 23.9 | a23.9-b23.9-a22.10*-b22.9* | CCTATGGACAC-TACGCACGTT-GTTAAGTCCG-ATAGCACCGAA |
| 329 | 23.10 | a23.10-b23.10-a22.11*-b22.10* | CAGAGATGAAC-TTGACTCGTT-GATCGCCAGG-ACGGAGCTCGA |
| 330 | 23.11 | a23.11-b23.11-a22.12*-b22.11* | CACCCTAGCGC-TGGGCACTTT-GCGACTCACG-ACGCTTTGTGA |

TABLE 1-continued

Single Stranded Oligonucleotides

| SEQ ID NO. | strand name | segment composition | segment sequences |
|---|---|---|---|
| 331 | 23.12 | a23.12-b23.12-a22.13*-b22.12* | CCTGCCCGTAC-TATACATAGT-GTAGGGAGGG-AGCGCCCTTTA |
| 332 | 23.13 | a23.13-b23.13-a22.14*-b22.13* | CGAAGAGACCC-TTGATTTGGT-GCAATTCTAG-AGTGGCATACA |
| 333 | 23.14 | a23.14-b23.14-a22.15*-b22.14* | CCTTTGCCGGC-TTCTATACTT-GTCCCAGCCG-AATGAGAGGCA |
| 334 | 24.1 | 10T-b24.1-a23.1*-10T | TTTTTTTTTT-TCAGTATGTAT-GGGCAGGCATG-TTTTTTTTTT |
| 335 | 24.2 | a24.2-b24.2-a23.2*-b23.1* | CTGTATCGGC-TTTAGTATAAT-GTATAGTCTTG-AAGTTAGCAA |
| 336 | 24.3 | a24.3-b24.3-a23.3*-b23.2* | CATCTGGGTC-TACAAGACCCT-GGATGCGCGTG-AGCGTCCTGA |
| 337 | 24.4 | a24.4-b24.4-a23.4*-b23.3* | CACAGATGTC-TATTTGCGAGT-GCAGCTTTACG-AATAAACGGA |
| 338 | 24.5 | a24.5-b24.5-a23.5*-b23.4* | CAGCGTGGAC-TCGTAACAATT-GTGCATTCACG-ATAGACCATA |
| 339 | 24.6 | a24.6-b24.6-a23.6*-b23.5* | CCGGCTCGCC-TCTGGGTAGCT-GTATTACCGAG-AGTCTACCGA |
| 340 | 24.7 | a24.7-b24.7-a23.7*-b23.6* | CGCCTAGCTC-TAGCAAACTGT-GGAGACTCTTG-ATAGCATAAA |
| 341 | 24.8 | a24.8-b24.8-a23.8*-b23.7* | CCCGGCTATC-TAGTGCGACGT-GGGCCAGCCGG-ACTGTCTAAA |
| 342 | 24.9 | a24.9-b24.9-a23.9*-b23.8* | CCAGAATGAC-TCGACCTCGGT-GTGTCCATAGG-ACGCAGCCCA |
| 343 | 24.10 | a24.10-b24.10-a23.10*-b23.9* | CAAAGACGAC-TCTATTCCGTT-GTTCATCTCTG-AACGTGCGTA |
| 344 | 24.11 | a24.11-b24.11-a23.11*-b23.10* | CTGGGCCAAC-TACGGGCCTCT-GCGCTAGGGTG-AACGAGTCAA |
| 345 | 24.12 | a24.12-b24.12-a23.12*-b23.11* | CGTGTGTGAC-TGTTCGGACCT-GTACGGGCAGG-AAAGTGCCCA |
| 346 | 24.13 | a24.13-b24.13-a23.13*-b23.12* | CACCGTTTCC-TAAGTAGTCAT-GGGTCTCTTCG-ACTATGTATA |
| 347 | 24.14 | a24.14-b24.14-a23.14*-b23.13* | CCCAGGCTTC-TGTAAGAGTAT-GCCGGCAAAGG-ACCAAATCAA |
| 348 | 24.15 | a24.15-11T-11T-b23.14* | CTTGGAAGAC-TTTTTTTTTTT-TTTTTTTTTTT-AAGTATAGAA |
| 349 | 25.1 | a24.2*-b24.1* | GCCGATACAGA-TACATACTGA |
| 350 | 25.2 | a24.3*-b24.2* | GACCCAGATGA-TTATACTAAA |
| 351 | 25.3 | a24.4*-b24.3* | GACATCTGTGA-GGGTCTTGTA |
| 352 | 25.4 | a24.5*-b24.4* | GTCCACGCTGA-CTCGCAAATA |
| 353 | 25.5 | a24.6*-b24.5* | GGCGAGCCGGA-ATTGTTACGA |
| 354 | 25.6 | a24.7*-b24.6* | GAGCTAGGCGA-GCTACCCAGA |
| 355 | 25.7 | a24.8*-b24.7* | GATAGCCGGGA-CAGTTTGCTA |
| 356 | 25.8 | a24.9*-b24.8* | GTCATTCTGGA-CGTCGCACTA |
| 357 | 25.9 | a24.10*-b24.9* | GTCGTCTTTGA-CCGAGGTCGA |
| 358 | 25.10 | a24.11*-b24.10* | GTTGGCCCAGA-ACGGAATAGA |
| 359 | 25.11 | a24.12*-b24.11* | GTCACACACGA-GAGGCCCGTA |
| 360 | 25.12 | a24.13*-b24.12* | GGAAACGGTGA-GGTCCGAACA |
| 361 | 25.13 | a24.14*-b24.13* | GAAGCCTGGGA-TGACTACTTA |
| 362 | 25.14 | a24.15*-b24.14* | GTCTTCCAAGA-TACTCTTACA |

REFERENCES

1. Seeman, N. Nature 2003, 421, 427-431.
2. Feldkamp, U.; Niemeyer, C. Angewandte Chemie International Edition 2006, 45, 1856-1876.
3. Bath, J.; Turberfield, A. Nature Nanotechnology 2007, 2, 275-284.
4. Yan, H.; Park, S. H.; Finkelstein, G.; Reif, J. H.; LaBean, T. H. Science 2003, 301(5641), 1882-1884.
5. Le, J. D.; Pinto, Y.; Seeman, N. C.; Musier-Forsyth, K.; Taton, T. A.; Kiehl, R. A. Nano Lett. 2004, 4, 2343-2347.
6. Sharma, J.; Ke, Y.; Lin, C.; Chhabra, R.; Wang, Q.; Nangreave, J.; Liu, Y.; Yan, H. Angew. Chem. Int. Ed. 2008, 47, 5157-5159.

7. Chen, Y.; Liu, H. P.; Ye, T.; Kim, J.; Mao, C. D. J. Am. Chem. Soc. 2007, 129.
8. Douglas, S. M.; Chou, J. J.; Shih, W. M. Proc. Natl Acad. Sci. USA 2007, 104, 6644-6648.
9. Fu, T. J.; Seeman, N. C. Biochemistry 1993, 32, 3211-3220.
10. Winfree, E.; Liu, F.; Wenzler, L.; Seeman, N. Nature 1998, 394, 539-544.
11. Rothemund, P. Nature 2006, 440, 297-302.
12. Douglas, S.; Dietz, H.; Liedl, T.; Hogberg, B.; Graf, F.; Shih, W. Nature 2009, 459, 414-418.
13. Dietz, H.; Douglas, S.; Shih, W. Science 2009, 325, 725-730.
14. Mitchell, J. C.; Harris, J. R.; Malo, J.; Bath, J.; Turberfield, A. J. J. Am. Chem. Soc. 2004, 126, 16342-16343.
15. Liu, D.; Park, S.; Reif, J.; LaBean, T. Proceedings of the National Academy of Sciences of the United States of America 2004, 101, 717-722.
16. Rothemund, P. W. K.; Ekani-Nkodo, A.; Papadakis, N.; Kumar, A.; Fygenson, D. K.; Winfree, E. J. Am. Chem. Soc. 2004, 126, 16344-16353.
17. Rothemund, P.; Papadakis, N.; Winfree, E. PLoS Biology 2004, 2, 2041-2053.
18. Mathieu, F.; Liao, S.; Kopatscht, J.; Wang, T.; Mao, C.; Seeman, N. C. Nano Lett. 2005, 5, 661-665.
19. Park, S. H.; Barish, R.; Li, H. Y.; Reif, J. H.; Finkelstein, G.; Yan, H.; LaBean, T. H. Nano Lett. 2005, 5, 693-696.
20. Liu, H.; Chen, Y.; He, Y.; Ribbe, A.; Mao, C. Angew. Chem. Int. Ed. 2006, 45, 1942-1945.
21. Kuzuya, A.; Wang, R. S.; Sha, R. J.; Seeman, N. C. Nano Lett. 2007, 7, 1757-1763.
22. Schulman, R.; Winfree, E. Proc. Natl Acad. Sci. USA (in press) 2007, 104, 15236-15241.
23. Lin, C.; Yan, L.; Rinker, S.; Yan, H. ChemBioChem (in press) 2006.
24. Yin, P.; Hariadi, R.; Sahu, S.; Choi, H. M. T.; Park, S. H.; LaBean, T. H.; J. H. Reif, Science 2008, 321, 824-826.
25. Yin, P.; Choi, H. M. T.; Calvert, C. R.; Pierce, N. A. Nature 2008, 451, 318-322.
26. Yurke, B.; Turberfield, A.; Mills, Jr., A.; Simmel, F.; Neumann, J. Nature 2000, 406, 605-608.
27. Pieles, U.; Englisch, U. Nucleic Acids Research 1989, 17, 285-299.
28. Killops, K.; Campus, L.; Hawker, C. Journal of the American Chemical Society 2008, 130, 5062-5064.
29. Winfree, E. On the computational power of DNA annealing and ligation. In DNA Based Computers; Lipton, R.; Baum, E., Eds.; American Mathematical Society: Providence, R.I., 1996.
30. Winfree, E. Algorithmic Self-Assembly of DNA, Ph.D. thesis, California Institute of Technology, 1998.
31. Rothemund, P. W. K.; Winfree, E. The program-size complexity of self-assembled squares (extended abstract). In Proceedings of the thirty-second annual ACM symposium on Theory of computing; ACM Press: 2000.
32. Barish, R. D.; Schulman, R.; Rothemund, P. W. K.; Winfree, E. Proceedings of the National Academy of Sciences 2009, 106, 6054.
33. Chen, H. L.; Cheng, Q.; Goel, A.; Huang, M. D.; Espanes, P. M. d. Invadable self-assembly: Combining robustness with efficiency. In Proceedings of the 15th annual ACM-SIAM Symposium on Discrete Algorithms (SODA); 2004.
35. Sharma, J.; Chhabra, R.; Cheng, A.; Brownell, J.; Liu, Y.; Yan, H. Science 2009, 112-116.
36. Li, H.; LaBean, T. H.; Kenan, D. J. Organic and Biomolecular Chemistry 2006, 3420-3426.
38. Yin, P.; Yan, H.; Daniell, X.; Turberfield, A. J.; Reif, J. Angewandte Chemie International Edition 2004, 43, 4906-4911.
39. Yin, P.; Turberfield, A. J.; Reif, J. H. Designs of Autonomous Unidirectional Walking DNA Devices. In Proc. 10th International Meeting on DNA Computing; 2004.
40. Reif, J. H.; Sahu, S.; Yin, P. Compact Error-Resilient Computational DNA Tiling Assemblies. In Proc. 10th International Meeting on DNA Computing; 2004.
41. Reif, J. H.; Sahu, S.; Yin, P. Complexity of Graph Self-assembly in Accretive Systems and Self-Destructible Systems. In Proc. 11th International Meeting on DNA Computing; 2005.
42. Sahu, S.; Yin, P.; Reif, J. H. A Self-Assembly Model of Time-Dependent Glue Strength. In Proc. $11^{th}$ International Meeting on DNA Computing; 2005.
43. Park, S. H.; Yin, P.; Liu, Y.; Reif, J. H.; LaBean, T. H.; Yan, H. Nano Letters 2005, 5, 729-733.
44. Yin, P.; Hartemink, A. J. Bioinformatics 2005, 21, 869-879.
45. Sekulic, A.; Hudson, C. C.; Homme, J. L.; Yin, P.; Otterness, D. M.; Karnitz, L. M.; Abraham, R. T. Cancer Research 2000, 60, 3504-3513.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A nucleic acid structure comprising a plurality of oligonucleotides, wherein at least one oligonucleotide of the plurality comprises at least four domains, wherein each of the four domains is annealed to a complementary domain of another oligonucleotide of the plurality to form at least two parallel double helices within the nucleic acid structure, wherein oligonucleotides having single-stranded poly(T), poly(A) or poly(C) domains that each have a length of 4-22 nucleotides are present at borders around the nucleic acid structure.

2. The nucleic acid structure of claim 1, wherein at least one double helix within the nucleic acid structure comprises 2 or more unique domains.

3. The nucleic acid structure of claim 1, wherein at least 50% of the double helices within the nucleic acid structure comprise one or more unique domains.

4. The nucleic acid structure of claim 1, wherein the nucleic acid structure comprises at least 5, at least 10, or at least 20 parallel double helices.

5. The nucleic acid structure of claim 1, wherein a first subset of oligonucleotides of the plurality comprises 2 domains and a second subset of oligonucleotides of the plurality comprises 4 domains.

6. The nucleic acid structure of claim 1, wherein the oligonucleotides are 21-104 nucleotides in length.

7. The nucleic acid structure of claim 1, wherein the oligonucleotides are DNA oligonucleotides.

8. The nucleic acid structure of claim 1, wherein the oligonucleotides are L-DNA oligonucleotides.

9. The nucleic acid structure of claim 1, wherein at least one of the double helices within the nucleic acid structure is unique.

10. The nucleic acid structure of claim 9, wherein the nucleic acid structure comprises 2 or more unique double helices.

11. The nucleic acid structure of claim 9, wherein at least 50% of the double helices are unique.

12. The nucleic acid structure of claim 9, wherein at least 50% of the double helices comprise one or more unique domains.

13. The nucleic acid structure of claim 9, wherein the nucleic acid structure comprises at least 5, at least 10, or at least 20 parallel double helices.

14. The nucleic acid structure of claim 9, wherein a first subset of oligonucleotides of the plurality comprises 2 domains and a second subset of oligonucleotides of the plurality comprises 4 domains.

15. The nucleic acid structure of claim 1, wherein at least one oligonucleotide in the nucleic acid structure is unique.

16. A composition comprising a plurality of nucleic acid structures of claim 1, wherein at least 50% of the nucleic acid structures of the plurality are identical.

17. A composite nucleic acid structure comprising at least two nucleic acid structures of claim 1, conjugated to each other through a spacer-linker.

18. The nucleic acid structure of claim 1, wherein the nucleic acid structure has an internal void pattern.

19. The nucleic acid structure of claim 1, wherein the nucleic acid structure further comprises oligonucleotides having a handle domain.

20. The nucleic acid structure of claim 19, wherein the oligonucleotides having a handle domain are present at borders of the nucleic acid structure.

21. The nucleic acid structure of claim 19, wherein the handle domain is bound to an oligonucleotide conjugated to a moiety of interest.

22. The nucleic acid structure of claim 1, wherein the single-stranded poly(T), poly(A) or poly(C) domains have a length of 10 nucleotides.

23. The nucleic acid structure of claim 1, wherein the single-stranded poly(T), poly(A) or poly(C) domains have a length of 11 nucleotides.

* * * * *